United States Patent
Predick et al.

(10) Patent No.: US 12,138,179 B2
(45) Date of Patent: Nov. 12, 2024

(54) EXPANDABLE IMPLANT ASSEMBLY WITH COMPRESSION FEATURES

(71) Applicant: Life Spine, Inc., Huntley, IL (US)

(72) Inventors: Daniel Predick, West Lafayette, IN (US); Madeline Wolters, St. Charles, IL (US); Michael S. Butler, St. Charles, IL (US)

(73) Assignee: Life Spine, Inc., Huntley, IL (US)

( * ) Notice: Subject to any disclaimer, the term of this patent is extended or adjusted under 35 U.S.C. 154(b) by 0 days.

(21) Appl. No.: 17/836,170

(22) Filed: Jun. 9, 2022

(65) Prior Publication Data
US 2022/0296385 A1     Sep. 22, 2022

Related U.S. Application Data

(63) Continuation of application No. 16/896,894, filed on Jun. 9, 2020, now Pat. No. 11,382,764.
(Continued)

(51) Int. Cl.
*A61F 2/44*      (2006.01)
*A61F 2/30*      (2006.01)

(52) U.S. Cl.
CPC .... *A61F 2/447* (2013.01); *A61F 2002/30387* (2013.01); *A61F 2002/30556* (2013.01);
(Continued)

(58) Field of Classification Search
CPC .......... A61F 2/44; A61F 2/447; A61F 2/4461; A61F 2002/30387; A61F 2002/30556;
(Continued)

(56) References Cited

U.S. PATENT DOCUMENTS 904,434 A    11/1908   Huff
1,925,385 A    9/1933   Humes
(Continued)

FOREIGN PATENT DOCUMENTS

CN     102427769 A    4/2012
CN     205866898 U    1/2017
(Continued)

OTHER PUBLICATIONS

Bacfuse® Spinous Process Fusion Plate Surgical Technique, 2011, Pioneer Surgical, 12 pages.
(Continued)

*Primary Examiner* — Jessica Weiss
(74) *Attorney, Agent, or Firm* — Foley & Lardner LLP

(57) ABSTRACT

An expandable implant includes a base member, an adjustable member adjustably coupled to the base member and movable between a first, collapsed position, and a second, expanded position, a control assembly including a control shaft, wherein manipulation of the control shaft causes relative movement of the adjustable member relative to the base member, wherein the base member and the adjustable member are coupled together at least in part via the control assembly such that the control shaft is rotationally fixed relative to the base member and the adjustable member, and the adjustable member is resiliently compressible relative to the base member.

19 Claims, 38 Drawing Sheets

Related U.S. Application Data

(60) Provisional application No. 62/859,347, filed on Jun. 10, 2019.

(52) U.S. Cl.
CPC ............ *A61F 2002/30579* (2013.01); *A61F 2002/30594* (2013.01); *A61F 2002/30828* (2013.01); *A61F 2002/30879* (2013.01)

(58) Field of Classification Search
CPC .. A61F 2002/30579; A61F 2002/30594; A61F 2002/30828; A61F 2002/30879
USPC ............................................ 623/17.11–17.16
See application file for complete search history.

(56) References Cited

U.S. PATENT DOCUMENTS

| | | | |
|---|---|---|---|
| 3,846,846 A | 11/1974 | Fischer | |
| 4,466,426 A | 8/1984 | Blackman | |
| 4,636,217 A | 1/1987 | Ogilvie et al. | |
| 4,743,256 A | 5/1988 | Brantigan | |
| 4,863,476 A | 9/1989 | Shepperd | |
| 5,098,435 A | 3/1992 | Stednitz et al. | |
| 5,192,327 A | 3/1993 | Brantigan | |
| 5,236,460 A | 8/1993 | Barber | |
| 5,390,683 A | 2/1995 | Pisharodi | |
| 5,522,899 A * | 6/1996 | Michelson ............ A61F 2/4455 |
| | | | 606/279 |
| 5,609,635 A | 3/1997 | Michelson | |
| 5,645,599 A | 7/1997 | Samani | |
| 5,658,335 A | 8/1997 | Allen | |
| 5,658,337 A | 8/1997 | Kohrs et al. | |
| 5,776,199 A | 7/1998 | Michelson | |
| 5,836,948 A | 11/1998 | Zucherman et al. | |
| 5,860,977 A | 1/1999 | Zucherman et al. | |
| 5,876,404 A | 3/1999 | Zucherman et al. | |
| 6,045,579 A | 4/2000 | Hochshuler et al. | |
| 6,048,342 A | 4/2000 | Zucherman et al. | |
| 6,068,630 A | 5/2000 | Zucherman et al. | |
| 6,074,390 A | 6/2000 | Zucherman et al. | |
| 6,080,193 A | 6/2000 | Hochshuler et al. | |
| 6,113,638 A | 9/2000 | Williams et al. | |
| 6,126,689 A | 10/2000 | Brett | |
| 6,129,763 A | 10/2000 | Chauvin et al. | |
| 6,176,882 B1 | 1/2001 | Biedermann et al. | |
| 6,183,471 B1 | 2/2001 | Zucherman et al. | |
| 6,190,387 B1 | 2/2001 | Zucherman et al. | |
| 6,235,030 B1 | 5/2001 | Zucherman et al. | |
| 6,290,724 B1 | 9/2001 | Marino | |
| 6,302,914 B1 | 10/2001 | Michelson | |
| 6,375,682 B1 | 4/2002 | Fleischmann et al. | |
| 6,409,766 B1 | 6/2002 | Brett | |
| 6,443,989 B1 | 9/2002 | Jackson | |
| 6,443,990 B1 | 9/2002 | Aebi et al. | |
| 6,447,544 B1 | 9/2002 | Michelson | |
| 6,451,019 B1 | 9/2002 | Zucherman et al. | |
| 6,491,724 B1 | 12/2002 | Ferree | |
| 6,494,883 B1 | 12/2002 | Ferree | |
| 6,537,320 B1 | 3/2003 | Michelson | |
| 6,576,016 B1 | 6/2003 | Hochshuler et al. | |
| 6,613,091 B1 | 9/2003 | Zdeblick et al. | |
| 6,641,614 B1 | 11/2003 | Wagner et al. | |
| 6,648,917 B2 | 11/2003 | Gerbec et al. | |
| 6,685,742 B1 | 2/2004 | Jackson | |
| 6,695,842 B2 | 2/2004 | Zucherman et al. | |
| 6,699,246 B2 | 3/2004 | Zucherman et al. | |
| 6,699,247 B2 | 3/2004 | Zucherman et al. | |
| 6,706,070 B1 | 3/2004 | Wagner et al. | |
| 6,752,832 B2 | 6/2004 | Neumann | |
| 6,773,460 B2 | 8/2004 | Jackson | |
| 6,796,983 B1 | 9/2004 | Zucherman et al. | |
| 6,800,092 B1 | 10/2004 | Williams et al. | |
| 6,849,093 B2 | 2/2005 | Michelson | |
| 7,001,385 B2 | 2/2006 | Bonutti | |
| 7,048,736 B2 | 5/2006 | Robinson et al. | |
| 7,087,055 B2 | 8/2006 | Lim et al. | |
| 7,101,375 B2 | 9/2006 | Zucherman et al. | |
| 7,214,243 B2 | 5/2007 | Taylor | |
| 7,217,291 B2 | 5/2007 | Zucherman et al. | |
| 7,220,280 B2 | 5/2007 | Kast et al. | |
| 7,250,055 B1 | 7/2007 | Vanderwalle | |
| 7,473,276 B2 | 1/2009 | Aebi et al. | |
| 7,503,933 B2 | 3/2009 | Michelson | |
| 7,621,950 B1 | 11/2009 | Globerman et al. | |
| 7,695,513 B2 | 4/2010 | Zucherman et al. | |
| 7,722,674 B1 | 5/2010 | Grotz | |
| 7,727,280 B2 | 6/2010 | McLuen | |
| 7,731,751 B2 | 6/2010 | Butler et al. | |
| 7,789,914 B2 | 9/2010 | Michelson | |
| D626,233 S | 10/2010 | Cipoletti et al. | |
| 7,824,427 B2 | 11/2010 | Perez-Cruet et al. | |
| 7,828,849 B2 | 11/2010 | Lim | |
| 7,837,734 B2 | 11/2010 | Zucherman et al. | |
| 7,846,188 B2 | 12/2010 | Moskowitz et al. | |
| 7,850,733 B2 | 12/2010 | Baynham et al. | |
| 7,854,766 B2 | 12/2010 | Moskowitz et al. | |
| 7,867,277 B1 | 1/2011 | Tohmeh | |
| 7,879,098 B1 | 2/2011 | Simmons, Jr. | |
| 7,942,903 B2 | 5/2011 | Moskowitz et al. | |
| 7,959,675 B2 | 6/2011 | Gately | |
| 7,972,363 B2 | 7/2011 | Moskowitz et al. | |
| 8,016,861 B2 | 9/2011 | Mitchell et al. | |
| 8,021,430 B2 | 9/2011 | Michelson | |
| 8,048,117 B2 | 11/2011 | Zucherman et al. | |
| 8,062,375 B2 | 11/2011 | Glerum et al. | |
| 8,070,817 B2 | 12/2011 | Gradl et al. | |
| 8,071,007 B1 | 12/2011 | Teoh et al. | |
| 8,105,382 B2 | 1/2012 | Olmos et al. | |
| 8,187,332 B2 | 5/2012 | Mcluen | |
| 8,231,656 B2 | 7/2012 | Lee et al. | |
| 8,241,330 B2 | 8/2012 | Lamborne et al. | |
| 8,241,364 B2 | 8/2012 | Hansell et al. | |
| 8,252,060 B2 | 8/2012 | Hansell et al. | |
| 8,257,370 B2 | 9/2012 | Moskowitz et al. | |
| 8,267,939 B2 | 9/2012 | Cipoletti et al. | |
| 8,303,663 B2 | 11/2012 | Jimenez et al. | |
| 8,308,804 B2 | 11/2012 | Krueger | |
| 8,343,190 B1 | 1/2013 | Mueller et al. | |
| 8,353,913 B2 | 1/2013 | Moskowitz et al. | |
| 8,353,963 B2 | 1/2013 | Glerum | |
| 8,366,777 B2 | 2/2013 | Matthis et al. | |
| 8,382,801 B2 | 2/2013 | Lamborne et al. | |
| 8,382,842 B2 | 2/2013 | Greenhalgh et al. | |
| 8,388,686 B2 | 3/2013 | Aebi et al. | |
| 8,394,129 B2 | 3/2013 | Lopez et al. | |
| 8,398,713 B2 | 3/2013 | Weiman | |
| 8,425,607 B2 | 4/2013 | Waugh et al. | |
| 8,435,298 B2 | 5/2013 | Weiman | |
| 8,444,696 B2 | 5/2013 | Michelson | |
| 8,454,706 B2 | 6/2013 | De Beaubien | |
| 8,491,659 B2 | 7/2013 | Weiman | |
| 8,506,629 B2 | 8/2013 | Weiland | |
| 8,518,120 B2 | 8/2013 | Glerum et al. | |
| 8,523,944 B2 * | 9/2013 | Jimenez ................. F16M 11/38 |
| | | | 623/17.15 |
| 8,529,628 B2 | 9/2013 | Marino et al. | |
| 8,535,380 B2 | 9/2013 | Greenhalgh et al. | |
| 8,551,173 B2 | 10/2013 | Lechmann et al. | |
| 8,556,979 B2 | 10/2013 | Glerum et al. | |
| 8,568,481 B2 | 10/2013 | Olmos et al. | |
| 8,597,360 B2 | 12/2013 | McLuen et al. | |
| 8,628,578 B2 | 1/2014 | Miller et al. | |
| 8,632,595 B2 | 1/2014 | Weiman | |
| 8,641,764 B2 | 2/2014 | Gately | |
| 8,641,766 B2 | 2/2014 | Donner et al. | |
| 8,663,332 B1 | 3/2014 | To et al. | |
| 8,679,183 B2 | 3/2014 | Glerum et al. | |
| 8,685,098 B2 | 4/2014 | Glerum et al. | |
| 8,690,883 B2 | 4/2014 | Collins et al. | |
| 8,702,798 B2 | 4/2014 | Matthis et al. | |
| 8,709,086 B2 | 4/2014 | Glerum | |
| 8,734,516 B2 | 5/2014 | Moskowitz et al. | |
| 8,795,366 B2 | 8/2014 | Varela | |

(56) References Cited

U.S. PATENT DOCUMENTS

| | | |
|---|---|---|
| 8,821,506 B2 | 9/2014 | Mitchell |
| 8,845,728 B1 | 9/2014 | Abdou |
| 8,845,731 B2 | 9/2014 | Weiman |
| 8,845,732 B2 | 9/2014 | Weiman |
| 8,845,734 B2 | 9/2014 | Weiman |
| 8,852,279 B2 | 10/2014 | Weiman |
| 8,858,638 B2 | 10/2014 | Michelson |
| 8,864,833 B2 | 10/2014 | Glerum et al. |
| 8,888,853 B2 | 11/2014 | Glerum et al. |
| 8,888,854 B2 | 11/2014 | Glerum et al. |
| 8,894,711 B2 | 11/2014 | Varela |
| 8,894,712 B2 | 11/2014 | Varela |
| 8,906,095 B2 | 12/2014 | Christensen et al. |
| 8,926,704 B2 | 1/2015 | Glerum et al. |
| 8,936,641 B2 | 1/2015 | Cain |
| 8,940,052 B2 | 1/2015 | Lechmann et al. |
| 8,974,505 B2 | 3/2015 | Sawa et al. |
| 9,005,293 B2 | 4/2015 | Moskowitz et al. |
| 9,034,041 B2 | 5/2015 | Wolters et al. |
| 9,034,045 B2 | 5/2015 | Davenport et al. |
| 9,039,771 B2 | 5/2015 | Glerum et al. |
| 9,044,284 B2 | 6/2015 | Sweeney |
| 9,060,876 B1 | 6/2015 | To et al. |
| 9,101,487 B2 | 8/2015 | Petersheim |
| 9,119,730 B2 | 9/2015 | Glerum et al. |
| 9,125,757 B2 | 9/2015 | Weiman |
| 9,149,367 B2 | 10/2015 | Davenport et al. |
| 9,186,258 B2 | 11/2015 | Davenport et al. |
| 9,186,262 B2 | 11/2015 | McLuen et al. |
| 9,198,772 B2 | 12/2015 | Weiman |
| 9,204,922 B2 | 12/2015 | Hooven |
| 9,204,972 B2 | 12/2015 | Weiman et al. |
| 9,204,974 B2 | 12/2015 | Glerum et al. |
| 9,211,196 B2 | 12/2015 | Glerum et al. |
| 9,216,095 B2 | 12/2015 | Glerum et al. |
| 9,216,098 B2 | 12/2015 | Trudeau et al. |
| 9,226,836 B2 | 1/2016 | Glerum |
| 9,233,009 B2 | 1/2016 | Gray et al. |
| 9,278,008 B2 | 3/2016 | Perloff et al. |
| 9,295,562 B2 | 3/2016 | Lechmann et al. |
| 9,301,854 B2 | 4/2016 | Moskowitz et al. |
| 9,333,092 B2 | 5/2016 | To et al. |
| 9,358,123 B2 | 6/2016 | McLuen et al. |
| 9,358,126 B2 | 6/2016 | Glerum et al. |
| 9,358,128 B2 | 6/2016 | Glerum et al. |
| 9,358,129 B2 | 6/2016 | Weiman |
| 9,370,434 B2 | 6/2016 | Weiman |
| 9,402,733 B1 | 8/2016 | To et al. |
| 9,402,738 B2 | 8/2016 | Niemiec et al. |
| 9,402,739 B2 | 8/2016 | Weiman et al. |
| 9,408,708 B2 | 8/2016 | Greenhalgh |
| 9,414,932 B2 | 8/2016 | Errico et al. |
| 9,421,111 B2 | 8/2016 | Baynham |
| 9,433,510 B2 | 9/2016 | Lechmann et al. |
| 9,445,919 B2 | 9/2016 | Palmatier et al. |
| 9,452,063 B2 | 9/2016 | Glerum et al. |
| 9,456,903 B2 | 10/2016 | Glerum et al. |
| 9,456,906 B2 | 10/2016 | Gray et al. |
| 9,474,622 B2 | 10/2016 | McLaughlin et al. |
| 9,480,579 B2 | 11/2016 | Davenport et al. |
| 9,486,325 B2 | 11/2016 | Davenport et al. |
| 9,486,326 B2 | 11/2016 | Gahman et al. |
| 9,492,286 B2 | 11/2016 | Biedermann et al. |
| 9,492,287 B2 | 11/2016 | Glerum et al. |
| 9,492,289 B2 | 11/2016 | Davenport et al. |
| 9,510,954 B2 | 12/2016 | Glerum et al. |
| 9,517,144 B2 | 12/2016 | McAtamney et al. |
| 9,532,821 B2 | 1/2017 | Moskowitz et al. |
| 9,532,883 B2 | 1/2017 | McLuen et al. |
| 9,539,103 B2 | 1/2017 | McLaughlin et al. |
| 9,539,108 B2 | 1/2017 | Glerum et al. |
| 9,554,918 B2 | 1/2017 | Weiman |
| 9,561,116 B2 | 2/2017 | Weiman et al. |
| 9,561,117 B2 | 2/2017 | Lechmann et al. |
| 9,572,677 B2 | 2/2017 | Davenport et al. |
| 9,579,124 B2 | 2/2017 | Gordon et al. |
| 9,585,765 B2 | 3/2017 | Niemiec et al. |
| 9,597,197 B2 | 3/2017 | Lechmann et al. |
| 9,597,200 B2 | 3/2017 | Glerum et al. |
| 9,603,713 B2 | 3/2017 | Moskowitz et al. |
| 9,610,174 B2 | 4/2017 | Wang et al. |
| 9,622,875 B2 | 4/2017 | Moskowitz et al. |
| 9,622,879 B2 | 4/2017 | Taylor et al. |
| 9,655,737 B2 | 5/2017 | Perloff et al. |
| 9,655,747 B2 | 5/2017 | Glerum et al. |
| 9,662,223 B2 | 5/2017 | Matthis et al. |
| 9,662,224 B2 | 5/2017 | Weiman et al. |
| 9,707,092 B2 | 7/2017 | Davenport et al. |
| 9,770,343 B2 | 9/2017 | Weiman |
| 9,782,265 B2 | 10/2017 | Weiman et al. |
| 9,801,733 B2 | 10/2017 | Wolters et al. |
| 9,814,601 B2 | 11/2017 | Moskowitz et al. |
| 9,833,336 B2 | 12/2017 | Davenport et al. |
| 9,839,528 B2 | 12/2017 | Weiman et al. |
| 9,848,993 B2 | 12/2017 | Moskowitz et al. |
| 9,848,997 B2 | 12/2017 | Glerum et al. |
| 9,848,998 B2 | 12/2017 | Moskowitz et al. |
| 9,855,151 B2 | 1/2018 | Weiman |
| 9,867,719 B2 | 1/2018 | Moskowitz et al. |
| 9,889,022 B2 | 2/2018 | Moskowitz et al. |
| 9,895,238 B2 | 2/2018 | Moskowitz et al. |
| 9,907,673 B2 | 3/2018 | Weiman et al. |
| 9,907,674 B2 | 3/2018 | Moskowitz et al. |
| 9,931,226 B2 | 4/2018 | Kurtaliaj et al. |
| 9,943,418 B2 | 4/2018 | Davenport et al. |
| 9,956,087 B2 | 5/2018 | Seifert et al. |
| 9,962,272 B1 | 5/2018 | Daffinson et al. |
| 9,968,462 B2 | 5/2018 | Weiman |
| 9,974,665 B2 | 5/2018 | McLuen et al. |
| 9,980,822 B2 | 5/2018 | Perloff et al. |
| 9,980,823 B2 | 5/2018 | Matthis et al. |
| 9,987,143 B2 | 6/2018 | Robinson et al. |
| 10,004,607 B2 | 6/2018 | Weiman et al. |
| 10,016,283 B2 | 7/2018 | McLuen et al. |
| 10,028,740 B2 | 7/2018 | Moskowitz et al. |
| 10,028,842 B2 | 7/2018 | Gray et al. |
| 10,034,772 B2 | 7/2018 | Glerum et al. |
| 10,034,773 B2 | 7/2018 | McLaughlin et al. |
| 10,052,213 B2 | 8/2018 | Glerum et al. |
| 10,058,433 B2 | 8/2018 | Lechmann et al. |
| 10,064,742 B2 | 9/2018 | Taylor et al. |
| 10,076,367 B2 | 9/2018 | Moskowitz et al. |
| 10,076,423 B2 | 9/2018 | Miller et al. |
| 10,080,669 B2 | 9/2018 | Davenport et al. |
| 10,085,844 B2 | 10/2018 | Perloff et al. |
| 10,085,849 B2 | 10/2018 | Weiman et al. |
| 10,092,417 B2 | 10/2018 | Weiman et al. |
| 10,092,422 B2 | 10/2018 | McLuen et al. |
| 10,098,757 B2 | 10/2018 | Logan et al. |
| 10,098,758 B2 | 10/2018 | Matthews et al. |
| 10,098,759 B2 | 10/2018 | Weiman |
| 10,105,239 B2 | 10/2018 | Niemiec et al. |
| 10,111,760 B2 | 10/2018 | Knapp et al. |
| 10,117,754 B2 | 11/2018 | Davenport et al. |
| 10,137,001 B2 | 11/2018 | Weiman |
| 10,137,007 B2 | 11/2018 | Dewey et al. |
| 10,143,500 B2 | 12/2018 | Niemiec et al. |
| 10,143,569 B2 | 12/2018 | Weiman et al. |
| 10,154,911 B2 | 12/2018 | Predick et al. |
| 10,159,583 B2 | 12/2018 | Dietzel et al. |
| 10,195,050 B2 * | 2/2019 | Palmatier .............. A61F 2/4425 |
| 10,213,321 B2 | 2/2019 | Knapp et al. |
| 10,219,913 B2 | 3/2019 | Matthews et al. |
| 10,226,359 B2 | 3/2019 | Glerum et al. |
| 10,251,643 B2 | 4/2019 | Moskowitz et al. |
| 10,285,819 B2 | 5/2019 | Greenhalgh |
| 10,285,820 B2 | 5/2019 | Greenhalgh |
| 10,292,828 B2 | 5/2019 | Greenhalgh |
| 10,292,830 B2 | 5/2019 | McLuen et al. |
| 10,299,934 B2 | 5/2019 | Seifert et al. |
| 10,307,268 B2 | 6/2019 | Moskowitz et al. |
| 10,350,085 B2 | 7/2019 | Glerum et al. |
| 10,376,386 B2 | 8/2019 | Moskowitz et al. |
| 10,383,741 B2 | 8/2019 | Butler et al. |

(56) References Cited

U.S. PATENT DOCUMENTS

| | | |
|---|---|---|
| 10,420,654 B2 | 9/2019 | Logan et al. |
| 10,426,632 B2 | 10/2019 | Butler et al. |
| 10,426,633 B2 | 10/2019 | Moskowitz et al. |
| 10,433,977 B2 | 10/2019 | Lechmann et al. |
| 10,449,058 B2 | 10/2019 | Lechmann et al. |
| 10,470,894 B2 | 11/2019 | Foley et al. |
| 10,478,319 B2 | 11/2019 | Moskowitz et al. |
| 10,512,550 B2 | 12/2019 | Bechtel et al. |
| 10,531,895 B2 | 1/2020 | Weiman et al. |
| 10,575,966 B2 | 3/2020 | Logan et al. |
| 10,617,533 B2 | 4/2020 | Glerum et al. |
| 10,624,761 B2 | 4/2020 | Davenport et al. |
| 10,639,166 B2 | 5/2020 | Weiman et al. |
| 10,682,240 B2 | 6/2020 | McLuen et al. |
| 10,702,393 B2 | 7/2020 | Davenport et al. |
| 10,709,569 B2 | 7/2020 | McLaughlin et al. |
| 10,709,571 B2 | 7/2020 | Iott et al. |
| 10,709,573 B2 | 7/2020 | Weiman et al. |
| 10,709,574 B2 | 7/2020 | McLuen et al. |
| 10,722,379 B2 | 7/2020 | McLaughlin et al. |
| 10,729,560 B2 | 8/2020 | Baker et al. |
| 10,729,562 B2 | 8/2020 | Knapp et al. |
| 10,736,754 B2 | 8/2020 | McLuen et al. |
| 10,758,367 B2 | 9/2020 | Weiman et al. |
| 10,765,528 B2 | 9/2020 | Weiman et al. |
| 10,772,737 B2 | 9/2020 | Gray et al. |
| 10,779,957 B2 | 9/2020 | Weiman et al. |
| 10,786,364 B2 | 9/2020 | Davenport et al. |
| 10,799,368 B2 | 10/2020 | Glerum et al. |
| 10,835,387 B2 | 11/2020 | Weiman et al. |
| 10,842,644 B2 | 11/2020 | Weiman et al. |
| 10,869,768 B2 | 12/2020 | Weiman et al. |
| 10,874,522 B2 | 12/2020 | Weiman |
| 10,874,523 B2 | 12/2020 | Weiman et al. |
| 10,925,752 B2 | 2/2021 | Weiman |
| 10,940,014 B2 | 3/2021 | Greenhalgh |
| 10,973,649 B2 | 4/2021 | Weiman et al. |
| 11,020,239 B2 | 6/2021 | Miller et al. |
| 11,051,951 B2 | 7/2021 | Robinson et al. |
| 11,065,128 B2 | 7/2021 | Zappacosta et al. |
| 11,083,584 B2* | 8/2021 | Lauf .................. A61F 2/4455 |
| 11,304,817 B2* | 4/2022 | Altarac ............... A61F 2/4455 |
| 11,304,818 B2* | 4/2022 | Butler ................ A61F 2/30771 |
| 2002/0010472 A1 | 1/2002 | Kuslich et al. |
| 2002/0029084 A1 | 3/2002 | Paul et al. |
| 2002/0091447 A1* | 7/2002 | Shimp .................. A61F 2/4455 623/17.16 |
| 2002/0128716 A1 | 9/2002 | Cohen et al. |
| 2002/0143343 A1 | 10/2002 | Castro |
| 2002/0143399 A1 | 10/2002 | Sutcliffe |
| 2002/0147461 A1 | 10/2002 | Aldrich et al. |
| 2002/0177897 A1 | 11/2002 | Michelson |
| 2003/0004576 A1 | 1/2003 | Thalgott |
| 2003/0040746 A1 | 2/2003 | Mitchell et al. |
| 2003/0040802 A1* | 2/2003 | Errico ..................... A61F 2/442 623/17.14 |
| 2003/0176926 A1 | 9/2003 | Boehm et al. |
| 2003/0236520 A1 | 12/2003 | Lim et al. |
| 2004/0073213 A1 | 4/2004 | Serhan et al. |
| 2004/0153156 A1 | 8/2004 | Cohen et al. |
| 2004/0167625 A1 | 8/2004 | Beyar et al. |
| 2004/0204747 A1 | 10/2004 | Kemeny et al. |
| 2004/0225292 A1 | 11/2004 | Sasso et al. |
| 2004/0230309 A1 | 11/2004 | DiMauro et al. |
| 2004/0254643 A1 | 12/2004 | Jackson |
| 2005/0027362 A1 | 2/2005 | Williams et al. |
| 2005/0033437 A1 | 2/2005 | Bao et al. |
| 2005/0070911 A1 | 3/2005 | Carrison et al. |
| 2005/0107800 A1 | 5/2005 | Frankel et al. |
| 2005/0119747 A1 | 6/2005 | Fabris Monterumici |
| 2005/0131536 A1 | 6/2005 | Eisermann et al. |
| 2005/0143827 A1 | 6/2005 | Globerman et al. |
| 2005/0177235 A1 | 8/2005 | Baynham et al. |
| 2005/0177236 A1 | 8/2005 | Mathieu et al. |
| 2005/0222681 A1 | 10/2005 | Richley et al. |
| 2005/0228391 A1 | 10/2005 | Levy et al. |
| 2005/0261769 A1 | 11/2005 | Moskowitz et al. |
| 2005/0278036 A1 | 12/2005 | Leonard et al. |
| 2006/0030943 A1 | 2/2006 | Peterman |
| 2006/0036258 A1 | 2/2006 | Zucherman et al. |
| 2006/0084988 A1 | 4/2006 | Kim |
| 2006/0089715 A1 | 4/2006 | Truckai et al. |
| 2006/0089718 A1 | 4/2006 | Zucherman et al. |
| 2006/0095136 A1 | 5/2006 | McLuen |
| 2006/0122701 A1 | 6/2006 | Kiester |
| 2006/0189999 A1 | 8/2006 | Zwirkoski |
| 2006/0241601 A1 | 10/2006 | Trautwein et al. |
| 2006/0241621 A1 | 10/2006 | Moskowitz et al. |
| 2006/0253201 A1 | 11/2006 | McLuen |
| 2006/0264938 A1 | 11/2006 | Zucherman et al. |
| 2006/0265077 A1* | 11/2006 | Zwirkoski ............ A61F 2/4611 623/17.14 |
| 2007/0072475 A1 | 3/2007 | Justin et al. |
| 2007/0142915 A1 | 6/2007 | Altarac et al. |
| 2007/0213739 A1 | 9/2007 | Michelson |
| 2007/0244485 A1 | 10/2007 | Greenhalgh et al. |
| 2007/0270968 A1 | 11/2007 | Baynham et al. |
| 2008/0114367 A1 | 5/2008 | Meyer |
| 2008/0114453 A1* | 5/2008 | Francis ................. A61F 2/4425 623/17.14 |
| 2008/0114456 A1 | 5/2008 | Dewey et al. |
| 2008/0119853 A1 | 5/2008 | Felt et al. |
| 2008/0119945 A1 | 5/2008 | Frigg |
| 2008/0140085 A1 | 6/2008 | Gately et al. |
| 2008/0140207 A1 | 6/2008 | Olmos et al. |
| 2008/0147193 A1 | 6/2008 | Matthis et al. |
| 2008/0161818 A1 | 7/2008 | Kloss et al. |
| 2008/0177391 A1 | 7/2008 | Mitchell et al. |
| 2008/0183211 A1 | 7/2008 | Lamborne et al. |
| 2008/0243251 A1 | 10/2008 | Stad et al. |
| 2008/0288077 A1* | 11/2008 | Reo ..................... A61F 2/442 623/17.11 |
| 2008/0312741 A1 | 12/2008 | Lee et al. |
| 2009/0005872 A1* | 1/2009 | Moumene ............ A61F 2/4425 623/17.15 |
| 2009/0062833 A1 | 3/2009 | Song |
| 2009/0062915 A1 | 3/2009 | Kohm et al. |
| 2009/0105832 A1 | 4/2009 | Allain et al. |
| 2009/0192553 A1 | 7/2009 | Maguire et al. |
| 2009/0198338 A1 | 8/2009 | Phan |
| 2009/0198339 A1 | 8/2009 | Kleiner et al. |
| 2009/0222099 A1 | 9/2009 | Liu et al. |
| 2009/0222100 A1* | 9/2009 | Cipoletti ................ A61F 2/447 606/90 |
| 2009/0228109 A1* | 9/2009 | Pointillant ............. A61F 2/442 623/17.16 |
| 2009/0312837 A1 | 12/2009 | Eisermann et al. |
| 2010/0082109 A1 | 4/2010 | Greenhalgh et al. |
| 2010/0103344 A1 | 4/2010 | Wang et al. |
| 2010/0179655 A1 | 7/2010 | Hansell et al. |
| 2010/0185291 A1* | 7/2010 | Jimenez ................ F16F 1/025 623/17.16 |
| 2010/0191336 A1 | 7/2010 | Greenhalgh |
| 2010/0204795 A1 | 8/2010 | Greenhalgh |
| 2010/0211176 A1 | 8/2010 | Greenhalgh |
| 2010/0234889 A1 | 9/2010 | Hess |
| 2010/0241167 A1 | 9/2010 | Taber et al. |
| 2010/0249937 A1 | 9/2010 | Blain et al. |
| 2010/0286777 A1 | 11/2010 | Errico et al. |
| 2011/0022090 A1 | 1/2011 | Gordon et al. |
| 2011/0029085 A1* | 2/2011 | Hynes ................... A61F 2/447 623/17.16 |
| 2011/0046682 A1 | 2/2011 | Stephan et al. |
| 2011/0054538 A1 | 3/2011 | Zehavi et al. |
| 2011/0066186 A1 | 3/2011 | Boyer et al. |
| 2011/0071635 A1 | 3/2011 | Zhang et al. |
| 2011/0077738 A1 | 3/2011 | Ciupik et al. |
| 2011/0144692 A1 | 6/2011 | Saladin et al. |
| 2011/0144753 A1 | 6/2011 | Marchek et al. |
| 2011/0144755 A1 | 6/2011 | Baynham et al. |
| 2011/0166654 A1 | 7/2011 | Gately |
| 2011/0172709 A1 | 7/2011 | Lyons et al. |
| 2011/0172716 A1 | 7/2011 | Glerum |

(56) References Cited

U.S. PATENT DOCUMENTS

| | | |
|---|---|---|
| 2011/0172774 A1 | 7/2011 | Varela |
| 2011/0178599 A1 | 7/2011 | Brett |
| 2011/0184468 A1 | 7/2011 | Metcalf et al. |
| 2011/0190817 A1 | 8/2011 | Thommen et al. |
| 2011/0196494 A1 | 8/2011 | Yedlicka et al. |
| 2011/0224731 A1 | 9/2011 | Smisson et al. |
| 2011/0282453 A1 | 11/2011 | Greenhalgh et al. |
| 2011/0301711 A1 | 12/2011 | Palmatier et al. |
| 2011/0319997 A1 | 12/2011 | Glerum et al. |
| 2012/0010717 A1 | 1/2012 | Spann |
| 2012/0016418 A1 | 1/2012 | Chin et al. |
| 2012/0022652 A1 | 1/2012 | Berger et al. |
| 2012/0035730 A1 | 2/2012 | Spann |
| 2012/0046748 A1 | 2/2012 | Weiman |
| 2012/0059472 A1 | 3/2012 | Weiman |
| 2012/0059474 A1 | 3/2012 | Weiman |
| 2012/0059475 A1 | 3/2012 | Weiman |
| 2012/0071978 A1 | 3/2012 | Suedkamp et al. |
| 2012/0109203 A1 | 5/2012 | Dryer et al. |
| 2012/0185049 A1 | 7/2012 | Varela |
| 2012/0203347 A1* | 8/2012 | Glerum ............ A61F 2/4611 623/17.16 |
| 2012/0221051 A1 | 8/2012 | Robinson |
| 2012/0226357 A1 | 9/2012 | Varela |
| 2012/0330422 A1 | 12/2012 | Weiman |
| 2013/0023993 A1 | 1/2013 | Weiman |
| 2013/0023994 A1 | 1/2013 | Glerum |
| 2013/0085572 A1 | 4/2013 | Glerum et al. |
| 2013/0103156 A1 | 4/2013 | Packer et al. |
| 2013/0116793 A1 | 5/2013 | Kloss |
| 2013/0144387 A1* | 6/2013 | Walker ............ A61F 2/4611 623/17.16 |
| 2013/0144391 A1 | 6/2013 | Siegal et al. |
| 2013/0158663 A1 | 6/2013 | Miller et al. |
| 2013/0158664 A1 | 6/2013 | Palmatier et al. |
| 2013/0158668 A1 | 6/2013 | Nichols et al. |
| 2013/0158669 A1 | 6/2013 | Sungarian et al. |
| 2013/0197647 A1 | 8/2013 | Wolters et al. |
| 2013/0211526 A1 | 8/2013 | Alheidt et al. |
| 2014/0067071 A1 | 3/2014 | Weiman et al. |
| 2014/0148904 A1 | 5/2014 | Robinson |
| 2014/0163683 A1 | 6/2014 | Seifert et al. |
| 2014/0188224 A1 | 7/2014 | Dmuschewsky |
| 2014/0236296 A1 | 8/2014 | Wagner et al. |
| 2014/0249629 A1 | 9/2014 | Moskowitz et al. |
| 2014/0277461 A1 | 9/2014 | Nebosky et al. |
| 2014/0277473 A1 | 9/2014 | Perrow |
| 2014/0277500 A1 | 9/2014 | Logan et al. |
| 2014/0288653 A1 | 9/2014 | Chen |
| 2014/0343678 A1 | 11/2014 | Suddaby et al. |
| 2015/0012097 A1 | 1/2015 | Ibarra et al. |
| 2015/0066145 A1 | 3/2015 | Rogers et al. |
| 2015/0100128 A1 | 4/2015 | Glerum et al. |
| 2015/0100130 A1 | 4/2015 | Perrow |
| 2015/0112438 A1 | 4/2015 | McLean |
| 2015/0173917 A1 | 6/2015 | Radcliffe et al. |
| 2015/0230931 A1 | 8/2015 | Greenhalgh |
| 2015/0351928 A1 | 12/2015 | Butler et al. |
| 2015/0374507 A1 | 12/2015 | Wolters et al. |
| 2016/0051377 A1 | 2/2016 | Weiman et al. |
| 2016/0089247 A1 | 3/2016 | Nichols et al. |
| 2016/0095718 A1 | 4/2016 | Weiman et al. |
| 2016/0113776 A1 | 4/2016 | Capote |
| 2016/0120660 A1 | 5/2016 | Melkent et al. |
| 2016/0242927 A1 | 8/2016 | Seifert et al. |
| 2016/0310291 A1 | 10/2016 | Greenhalgh |
| 2016/0361177 A1 | 12/2016 | Biedermann et al. |
| 2016/0367377 A1 | 12/2016 | Faulhaber |
| 2016/0374826 A1* | 12/2016 | Palmatier ............ A61F 2/4425 623/17.16 |
| 2017/0014244 A1 | 1/2017 | Seifert et al. |
| 2017/0056197 A1 | 3/2017 | Weiman et al. |
| 2017/0100255 A1* | 4/2017 | Hleihil ............ A61F 2/447 |
| 2017/0172756 A1 | 6/2017 | Faulhaber |
| 2017/0216036 A1 | 8/2017 | Cordaro |
| 2017/0224504 A1 | 8/2017 | Butler et al. |
| 2017/0224505 A1 | 8/2017 | Butler et al. |
| 2017/0246006 A1 | 8/2017 | Carnes et al. |
| 2017/0258605 A1 | 9/2017 | Blain et al. |
| 2017/0281432 A1 | 10/2017 | Glerum et al. |
| 2017/0296352 A1 | 10/2017 | Richerme et al. |
| 2017/0333198 A1 | 11/2017 | Robinson |
| 2017/0333199 A1 | 11/2017 | Sharifi-Mehr et al. |
| 2017/0333200 A1 | 11/2017 | Arnin |
| 2017/0348116 A1 | 12/2017 | Weiman |
| 2017/0367842 A1* | 12/2017 | Predick ............ A61F 2/447 |
| 2018/0000609 A1* | 1/2018 | Hessler ............ A61F 2/447 |
| 2018/0014947 A1 | 1/2018 | Baynham |
| 2018/0042732 A1 | 2/2018 | Seifert et al. |
| 2018/0049885 A1 | 2/2018 | Weiman et al. |
| 2018/0055652 A1 | 3/2018 | Davenport et al. |
| 2018/0185163 A1 | 7/2018 | Weiman et al. |
| 2018/0243107 A1 | 8/2018 | Foley et al. |
| 2018/0256359 A1 | 9/2018 | Greenhalgh |
| 2018/0296361 A1 | 10/2018 | Butler et al. |
| 2018/0303621 A1 | 10/2018 | Brotman et al. |
| 2018/0318101 A1 | 11/2018 | Engstrom |
| 2018/0325693 A1 | 11/2018 | Weiman et al. |
| 2018/0360616 A1 | 12/2018 | Luu |
| 2019/0021871 A1 | 1/2019 | Baynham |
| 2019/0133779 A1 | 5/2019 | McLaughlin et al. |
| 2019/0133784 A1 | 5/2019 | Gunn et al. |
| 2019/0201210 A1 | 7/2019 | Besaw et al. |
| 2019/0254836 A1 | 8/2019 | Cowan et al. |
| 2019/0254838 A1 | 8/2019 | Miller et al. |
| 2019/0298524 A1 | 10/2019 | Lauf et al. |
| 2019/0307577 A1 | 10/2019 | Predick et al. |
| 2019/0314168 A1 | 10/2019 | Faulhaber |
| 2019/0328540 A1 | 10/2019 | Seifert et al. |
| 2019/0374348 A1 | 12/2019 | Butler et al. |
| 2019/0388232 A1 | 12/2019 | Purcell et al. |
| 2019/0388238 A1 | 12/2019 | Lechmann et al. |
| 2020/0054461 A1 | 2/2020 | Marrocco et al. |
| 2020/0129307 A1 | 4/2020 | Hunziker et al. |
| 2020/0360153 A1 | 11/2020 | Weiman et al. |
| 2021/0015627 A1 | 1/2021 | Weiman et al. |
| 2021/0045891 A1 | 2/2021 | Rogers et al. |
| 2021/0045892 A1 | 2/2021 | Rogers et al. |
| 2021/0113349 A1 | 4/2021 | Weiman et al. |
| 2021/0137699 A1 | 5/2021 | Jang et al. |
| 2021/0259849 A1 | 8/2021 | Robinson et al. |
| 2021/0322181 A1 | 10/2021 | Predick |
| 2021/0353428 A1* | 11/2021 | Predick ............ A61F 2/447 |
| 2022/0133495 A1 | 5/2022 | Glerum et al. |
| 2022/0304823 A1 | 9/2022 | Melchor |
| 2022/0387184 A1 | 12/2022 | Josse et al. |

FOREIGN PATENT DOCUMENTS

| | | |
|---|---|---|
| DE | 94 07 806 U1 | 7/1994 |
| DE | 20314708 U1 | 11/2003 |
| DE | 10 2020 200 882 A1 | 7/2020 |
| EP | 0 880 950 A1 | 12/1998 |
| EP | 1 925 272 A1 | 5/2008 |
| EP | 2 777 633 A2 | 9/2014 |
| EP | 3 031 424 A1 | 6/2016 |
| EP | 3 245 982 | 11/2017 |
| EP | 3 366 263 A1 | 8/2018 |
| EP | 3 479 799 A1 | 5/2019 |
| EP | 3 769 725 A1 | 1/2021 |
| FR | 2717068 A1 | 4/1996 |
| FR | 2727003 B1 | 4/1997 |
| FR | 2894130 A1 | 6/2007 |
| GB | 0 284 462 A | 2/1928 |
| KR | 200290058 Y1 | 9/2002 |
| KR | 100905962 B1 | 7/2009 |
| WO | WO-95/31158 A1 | 11/1995 |
| WO | WO-99/26562 A1 | 6/1999 |
| WO | WO-00/44319 A1 | 8/2000 |
| WO | WO-02/44319 A1 | 6/2002 |
| WO | WO-2004/052245 | 6/2004 |
| WO | WO-2005/009299 A1 | 2/2005 |
| WO | WO-2006/102485 | 9/2006 |
| WO | WO-2006/105437 A2 | 10/2006 |

(56) References Cited

FOREIGN PATENT DOCUMENTS

| | | | |
|---|---|---|---|
| WO | WO-2009/124269 | A1 | 10/2009 |
| WO | WO-2010/148112 | | 12/2010 |
| WO | WO-2012/121726 | A1 | 9/2012 |
| WO | WO-2014/134590 | A1 | 9/2014 |
| WO | WO-2014/165319 | A1 | 10/2014 |
| WO | WO-2015/009793 | A1 | 1/2015 |
| WO | WO-2015/063721 | A1 | 5/2015 |
| WO | WO-2015/085111 | A1 | 6/2015 |
| WO | WO-2016/051095 | A1 | 4/2016 |
| WO | WO-2016/077610 | A1 | 5/2016 |
| WO | WO-2016/127139 | A1 | 8/2016 |
| WO | WO-2017/027277 | A1 | 2/2017 |
| WO | WO-2017/027873 | A1 | 2/2017 |
| WO | WO-2017/066463 | A1 | 4/2017 |
| WO | WO-2017/106614 | A1 | 6/2017 |
| WO | WO-2018/049227 | A1 | 3/2018 |
| WO | WO-2018/200507 | A1 | 11/2018 |
| WO | WO-2018/200530 | A1 | 11/2018 |
| WO | WO-2019/014139 | A1 | 1/2019 |
| WO | WO-2019/126213 | A1 | 6/2019 |
| WO | WO2019/0014139 | A1 | 7/2019 |
| WO | WO-2019/241687 | A1 | 12/2019 |
| WO | WO-2021/030645 | A1 | 2/2021 |

OTHER PUBLICATIONS

Extended European Search Report for European Application No. 14159101.6, dated Jun. 18, 2014, 6 pages.

Extended European Search Report for European Application No. 16169890.7, dated Oct. 21, 2016, 7 pages.

Folman, et al., "Posterior Lumbar Interbody Fusion for Degenerative Disc Disease Using a Minimally Invasive B-Twin Expandable Spinal Spacer." Journal of Spinal Disorders & Techniques. 2003, vol. 16, No. 5, pp. 455-460.

Foreign Action other than Search Report on PCT PCT/US2018/029149 Dtd Nov. 7, 2019.

Foreign Search Report on PCT PCT/US2019/037275 Dtd Sep. 24, 2019.

International Preliminary Report on Patentability for International Application No. PCT/US06/12060 mailing date Sep. 30, 2007, 3 pages.

International Search Report and Written Opinion for International Application No. PCT/US06/12060, mailing date Apr. 5, 2007, 3 pages.

International Search Report and Written Opinion for International Application No. PCT/US2006/012060, mail date Apr. 5, 2007, 4 pages.

International Search Report and Written Opinion for International Application No. PCT/US2012/057324, mail date Dec. 20, 2012, 10 pages.

International Search Report and Written Opinion in PCT PCT/US2021/030261 dated Aug. 31, 2021 (18 pages).

International Search Report and Written Opinion in PCT/US2021/031596 dated Sep. 28, 2021 (12 pages).

International Search Report and Written Opinion in PCT/US2021/033832 dated Sep. 17, 2021.

International Search Report and Written Opinion on PCT/US2020/036809 Dtd Sep. 14, 2020, 12 pages.

International Search Report and Written Opinion received for Life Spine, Inc., for PCT app. No. PCT/US2021026610 dated Jul. 20, 2021, 18 pages.

International Search Report for Application No. PCT/US06/12060, date of mailing Apr. 5, 2007, 1 page.

International Search Report for International Application No. PCT/US2018/029120, mail date Jun. 28, 2018, 17 pages.

International Search Report for International Application No. PCT/US2018/029149, mail date Jun. 25, 2018, 13 pages.

International Search Report on PCT/US2020/037020, Sep. 29, 2020, 20 pages.

Non-Final Office Action on U.S. Appl. No. 16/896,894 Dtd Oct. 14, 2021.

Schizas, C., "Spinal Fusion: Techniques Results and Limitations." European Cells and Materials. 2005, vol. 10, Suppl. 3, p. 1.

Search Report for International Application No. PCT/US2018/041306, mail date Sep. 28, 2018, 12 pages.

"MectaLIF Oblique & Posterior Intervertebral Body Fusion Device." Brochure. 2004, Medacta International, San Pietro, Switzerland.

"Webster's II New College Dictionary." Excerpts. 2005, Houghton Mifflin Co., p. 992.

"Wedge." Encyclopedia Brittanica. Aug. 14, 2008. britannica.com/print/article/638734.

International Search Report and Written Opinion in PCT/US2022/053230 dated May 3, 2023 (18 pages).

Kambin, P., et al., "Arthroscopic Discectomy of the Lumbar Spine." Clinical Orthopaedics and Related Research. Apr. 1997, No. 337, pp. 49-57.

Kim, D., et al. "Posterior Lumbar Interbody Fusion Using a Unilateral Single Cage and a Local Morselized Bone Graft in the Degenerative Lumbar Spine." Clinics in Orthopedic Surgery. 2009, vol. 1, No. 4, pp. 214-221.

Kim, Y, et al., "Clinical Applications of the Tubular Retractor on Spinal Disorders." Journal of Korean Neurosurgery, Nov. 2007, No. 42, pp. 244-250.

Moore, J., et al., "Mechanics Map—Wedges." Aug. 20, 2022, mechanicsmap.psu.edu/websites/7_friction/7-3_wedges/wedges.

Peltier, L. "Orthopedics: A History and Iconography" 1993, Norman Publishing, San Francisco, CA.

Sasso, R., et al., "Anterior Lumbar Interbody Fusion." Surgical Management of Low Back Pain. 2009, Chapter 10, pp. 87-95.

Tsuang, Y., et al., "Comparison of cage application modality in posterior lumbar interbody fusion with posterior instrumentation—A finite element study." Medical Engineering & Physics 31. 2009, pp. 565-570.

Virk, S., et al. "History of Spinal Fusion: Where We Came from and Where We Are Going." Current Concepts in Spinal Fusion. HSS Journal, 2020, No. 16, pp. 137-142.

Xiao, Y, et al., "Unilateral Transforaminal Lumbar Interbody Fusion: a Review of the Technique, Indications and Graft Materials." The Journal of International Medical Research. 2009, No. 37, pp. 908-917.

International Search Report and Written Opinion in PCT/US2023/021528 dated Aug. 24, 2023 (17 pages).

\* cited by examiner

EXPANDABLE IMPLANT ASSEMBLY WITH COMPRESSION FEATURES

CROSS-REFERENCE TO RELATED PATENT APPLICATIONS

This application is a continuation of U.S. application Ser. No. 16/896,894, filed Jun. 9, 2020, which claims the benefit of U.S. Provisional Application No. 62/859,347, filed Jun. 10, 2019, both of which are incorporated by reference herein in their entirety.

BACKGROUND

The present disclosure relates to expandable implants and devices, including spinal interbody and intravertebral body devices, and vertebral interbody and intravertebral devices that are expandable after spinal placement thereof.

Fusion cages, as well as other types of implants, bodies and/or devices, are frequently utilized in spinal surgery inside a vertebra (intravertebral) and/or between vertebrae of a patient (interbody), or adjacent other bone bodies. With interbody devices, one or more such spinal bodies are placed between vertebrae to provide support and promote fusion between adjacent vertebrae where such is necessary due to disease, injury, general deterioration or congenital problem. With intravertebral devices, one or more spinal bodies are placed within a vertebra. Spinal devices, such as fusion cages and/or the like, are inserted into a spinal space either anteriorly, posteriorly, laterally or posteriolaterally.

A problem with most spinal interbody and intravertebral devices is that they are static in size and difficult to position. This poses various problems with their use and/or implantation. Particularly, static sized spinal devices are fairly large in order to properly bridge the gap between adjacent vertebrae. This large size does not lend itself to microsurgery, arthroscopic surgery or the like. Furthermore, spinal devices that are difficult to position require more invasive surgery techniques, and longer surgery time to implant. This complicated positioning does not lend itself to minimally invasive surgery or even outpatient procedures.

Devices are now being made that are expandable and more easily positioned. Expandable interbody devices allow the device to be initially smaller than traditional non-expandable (static) interbody devices such that expandable interbody devices may be more easily inserted or implanted into the vertebral space. Moreover, expandable devices allow the surgeon to set the amount of expansion necessary for the particular patient rather than the static device dictating the spacing. Furthermore, expandable devices can include attachment points for manipulation tools. Expandable devices integrated with a manipulation tool allows the surgeon to more easily position and expand the implant rather than using several bulkier tools.

SUMMARY

One embodiment relates to an expandable implant, including a base member including a top surface, a first end, and a second end, and defining a central cavity positioned between the first end and the second end; an adjustable member including a top surface and at least one control channel, wherein the adjustable member is adjustably coupled to the base member and movable between a first, collapsed position, and a second, expanded position; a control shaft rotatably received by the base member, wherein rotation of the control shaft cause relative movement of the adjustable member relative to the base member; and at least one control member received on the control shaft and by the control channel, wherein rotation of the control shaft causes the control member to translate along the control shaft and along the control channel.

Another embodiment relates to an expandable implant, including a base member including a top surface, a first end, and a second end, and defining a central cavity positioned between the first end and the second end; an adjustable member including a top surface, a first control channel, and a second control channel; a control shaft rotatably received by the base member, wherein the control shaft defines a first acute angle with the first control channel and a second acute angle with the second control channel, and wherein rotation of the control shaft causes relative movement of the adjustable member relative to the base member; a first control member received on the control shaft and by the first control channel such that rotation of the control shaft causes translation of the first control member along the control shaft and along the first control channel; and a second control member received on the control shaft and by the second control channel such that rotation of the control shaft causes translation of the second control member along the control shaft and along the second control channel.

Another embodiment relates to an expandable implant, including a base member; an adjustable member movably coupled to the base member and defining a first control channel and a second control channel; a control shaft translationally fixed and rotatably movable relative to the base member, wherein rotation of the control shaft causes relative movement of the adjustable member relative to the base member, wherein the control shaft defines a first intersection angle with the first control channel and a second different intersection angle with the second control channel; a first control member received on the control shaft and in the first control channel such that rotation of the control shaft causes translation of the first control member along the control shaft and within the first control channel; and a second control member received on the control shaft and within the second control channel such that rotation of the control shaft causes translation of the first control member along the control shaft and within the first control channel.

This summary is illustrative only and is not intended to be in any way limiting. Other aspects, inventive features, and advantages of the devices or processes described herein will become apparent in the detailed description set forth herein, taken in conjunction with the accompanying figures, wherein like reference numerals refer to like elements.

Figure 1:
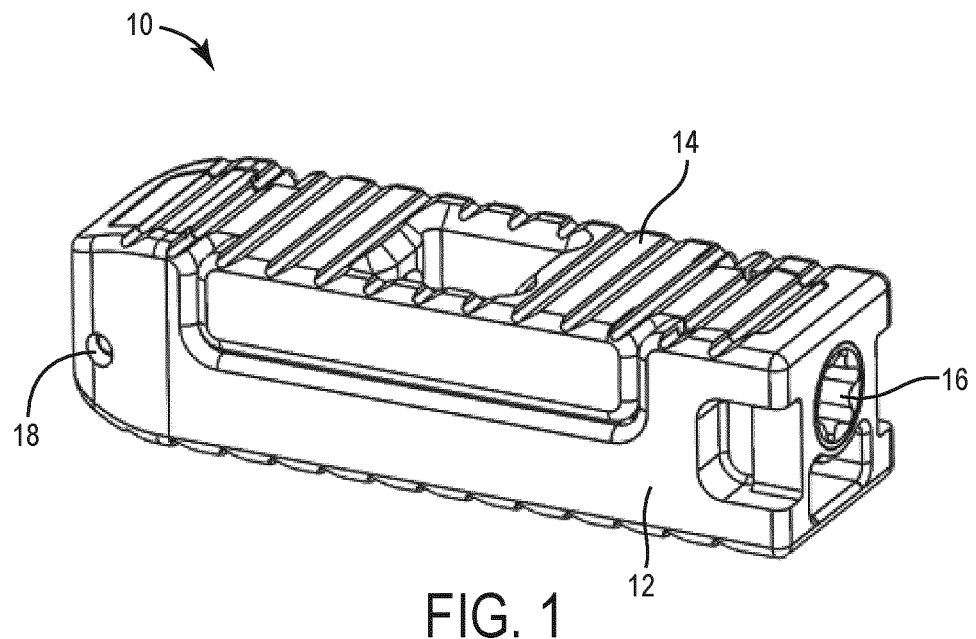
FIG. 1 is perspective view of an expandable implant in a collapsed position according to one embodiment.

Corresponding reference characters indicate corresponding parts throughout the several views. Although the drawings represent embodiments of the disclosure, the drawings are not necessarily to scale and certain features may be exaggerated in order to better illustrate and explain the principles of the present disclosure. The exemplifications set out herein illustrate several embodiments, but the exemplifications are not to be construed as limiting the scope of the disclosure in any manner.

DETAILED DESCRIPTION

The present disclosure relates to expandable and/or dynamic implants, including, but not limited to, interbody (between adjacent vertebrae), intravertebral-body (inside the vertebrae) and/or spinal stabilization devices that may or may not be used as interbody fusion cages or devices, interbody/intravertebral bodies/body stabilization devices and/or the like (e.g., spinal device(s)) for providing support, stabilization and/or promoting bone growth between or inside vertebrae or other portions of bone that have been destabilized or otherwise due to injury, illness and/or the like. Particularly, the present disclosure provides various versions of dynamic (expandable and/or expandable and retractable) interbody/intravertebral body devices that are usable in a spinal column or other areas of a human.

Various embodiments disclosed herein are directed to expandable implants that are implantable between adjacent bodies of bone. For example, the implant may be implanted or inserted into a human spine adjacent upper and lower vertebrae of the spine. According to various exemplary embodiments, the components of the implants disclosed herein may be made of any suitable material(s), including a variety of metals, plastics, composites, or other suitable bio-compatible materials. In some embodiments, one or more components of the implants disclosed herein may be made of the same material, while in other embodiments, different materials may be used for different components of the various implants.

Referring now to FIGS. 1-9C, an expandable implant 10 is shown according to an exemplary embodiment. Implant 10 is usable, for example, between and/or within vertebral bodies of the spine, and may share many of the features of the other inter/intra-body implants discussed elsewhere herein. It should be understood that implant 10 may in some embodiments be usable in other portions of the body in addition to the spine, and all such applications are to be understood to be within the scope of the present disclosure.

Figure 2:
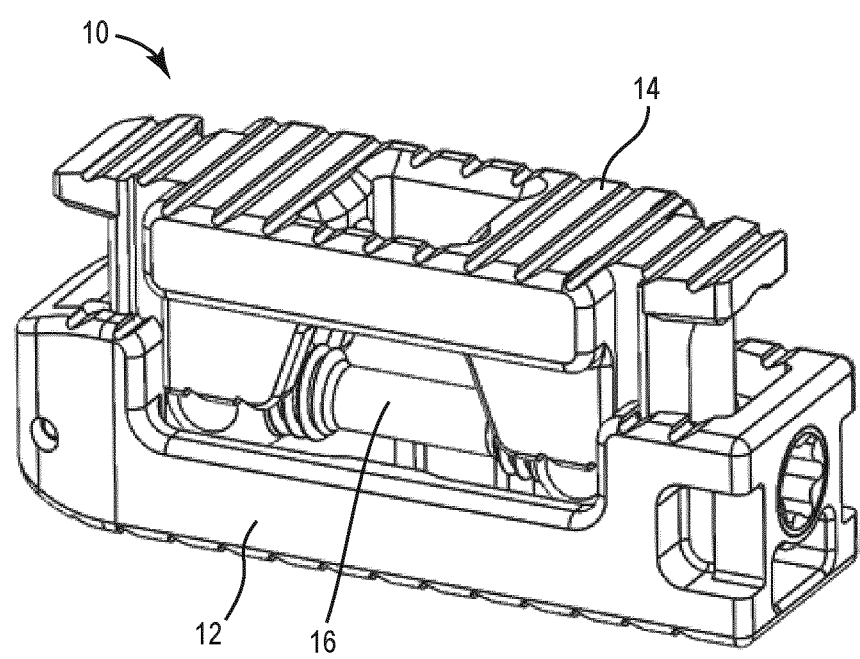
FIG. 2 is a perspective view of the implant of FIG. 1 in an expanded position according to one embodiment.
Figure 3:
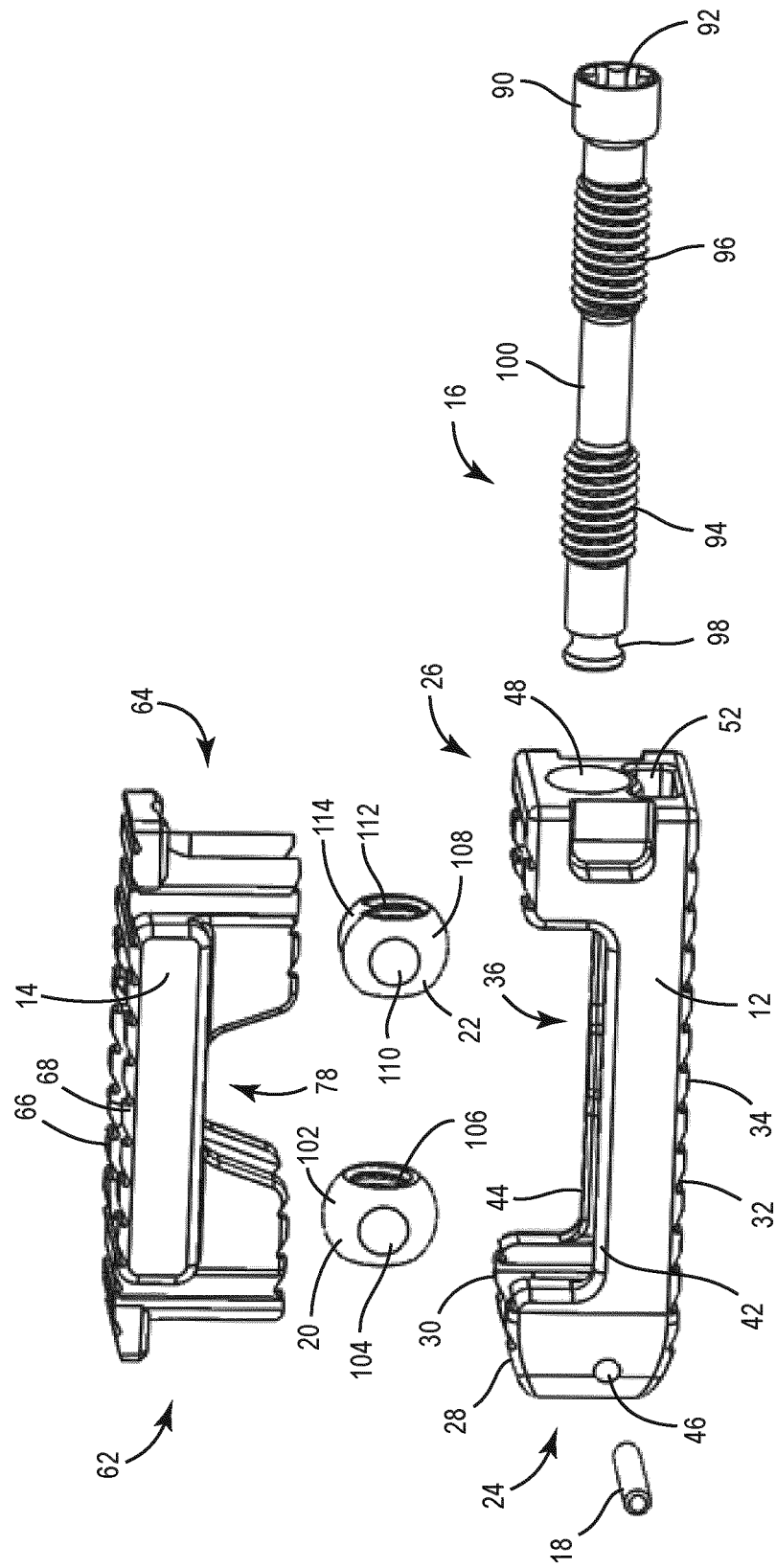
FIG. 3 is an exploded view of the implant of FIG. 1 according to one embodiment.

According to an exemplary embodiment, implant 10 includes a base member 12 and an adjustable member 14 adjustably coupled to the base member 12. A control shaft 16 is received by the base member 12 and is retained by a retention pin 18 passing through a portion of the base member 12. A first control member 20 and a second control member 22 are received on the control shaft 16 and are movable along the control shaft 16 to adjust a position of the adjustable member 14 between a collapsed position, as shown in FIG. 1, and an expanded position, as shown in FIG. 2.

Figure 6:
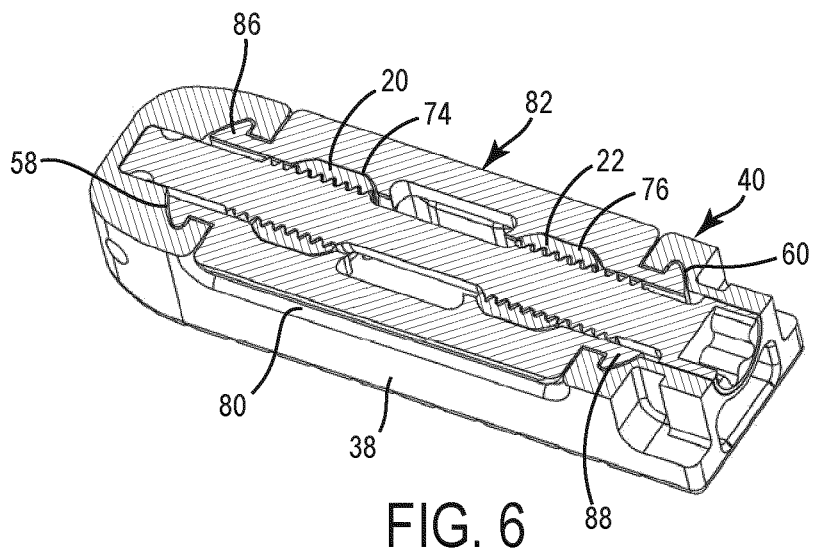
FIG. 6 is a top cross-sectional view of the implant of FIG. 1 according to one embodiment.
Figure 7:
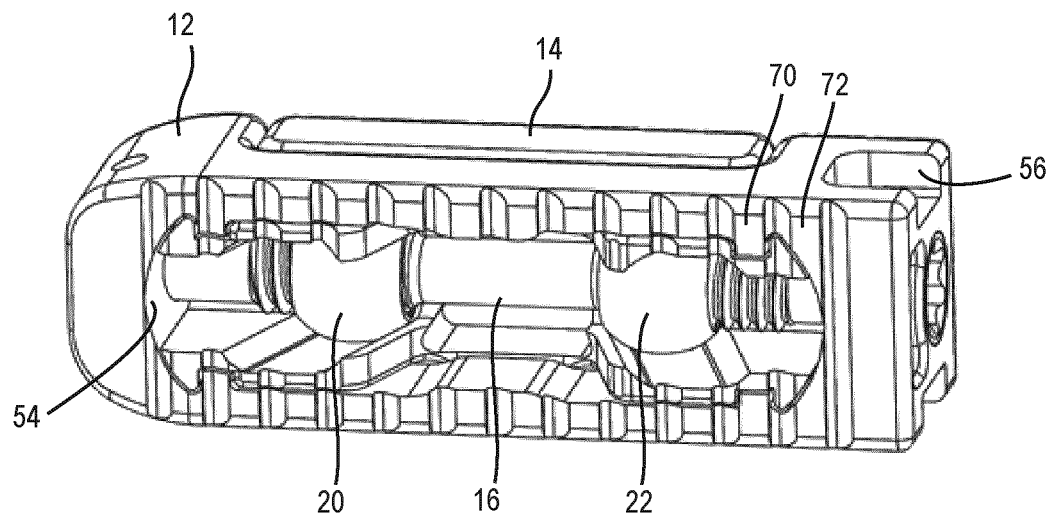
FIG. 7 is a bottom perspective view of the implant of FIG. 1 in a collapsed position according to one embodiment.
Figure 8:
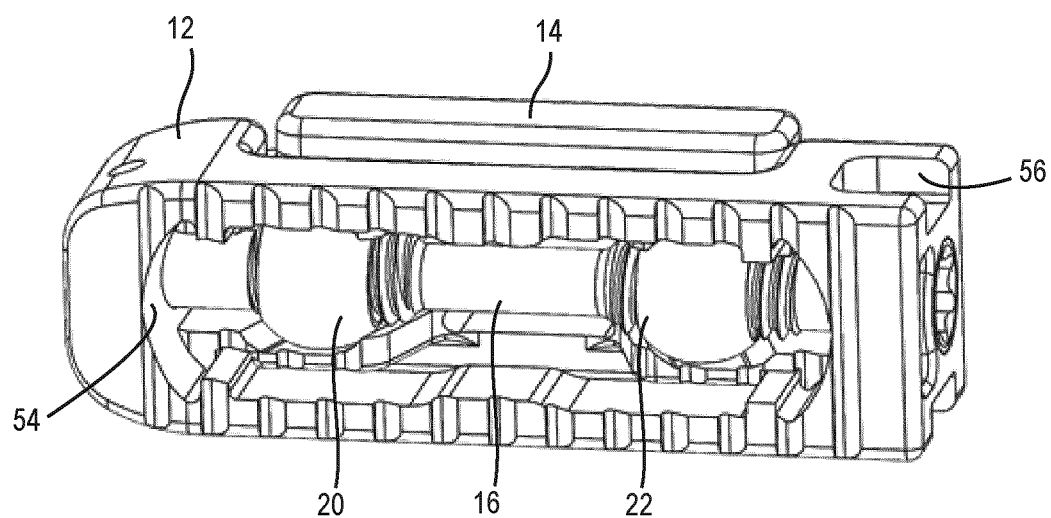
FIG. 8 is a bottom perspective view of the implant of FIG. 1 in an expanded position according to one embodiment.

In one embodiment, the base member 12 includes a front or first end 24, a rear or second end 26, and a central cavity 36 disposed between the first end 24 and the second end 26. The base member 12 further includes a top surface 28 having ridges or projections 30 formed by corresponding grooves, a bottom surface 32 opposite the top surface 28 and having ridges or projections 34 formed by corresponding grooves, a first side 38, and a second side 40. The projections 30, 34 are configured to engage adjacent portions of bone. The first side 38 defines a first side recess 42, and the second side 40 defines a second side recess 44. A pin aperture 46 extends through one or both of first side 38 and second side 40 and is configured to receive the retention pin 18 (e.g., in a press fit or other manner). The second end 26 of the base member 12 includes a control bore 48 configured to receive a first portion of the control shaft 16. The first end 24 of the base member 12 includes a control counterbore 50 (see FIG. 4) configured to receive a second portion of the control shaft 16. As shown in FIG. 6, in some embodiments, the first end 24 of the base member 12 further includes a dovetail recess 58, and the second end 26 of the base member 12 further includes a dovetail recess 60.

In one embodiment, the adjustable member 14 includes a front or first end 62, a rear or second end 64, and a central recess or cavity 78 positioned between the first end 62 and the second end 64. A top cavity 84 (see FIG. 5) in the adjustable member 14 extends to the central cavity 78. The adjustable member 14 further includes a top surface 66 having ridges or projections 68 formed by corresponding grooves, a bottom surface 70 including ridges or projections 72 (see FIG. 8) formed by corresponding grooves, a first side portion 80, and a second side portion 82. In some embodiments, the first and second side portions 80, 82 have shapes generally corresponding to the shapes of the first and second side recesses 42, 44 of base member 12. In other embodiments, the first and second side portions 80, 82 have shapes differing from the shapes of the first and second side recesses 42, 44 of the base member 12. The first end 62 of the adjustable member 14 further includes a dovetail projection 86, and the second end 64 of the adjustable member 14 further includes a dovetail projection 88.

Figure 4:
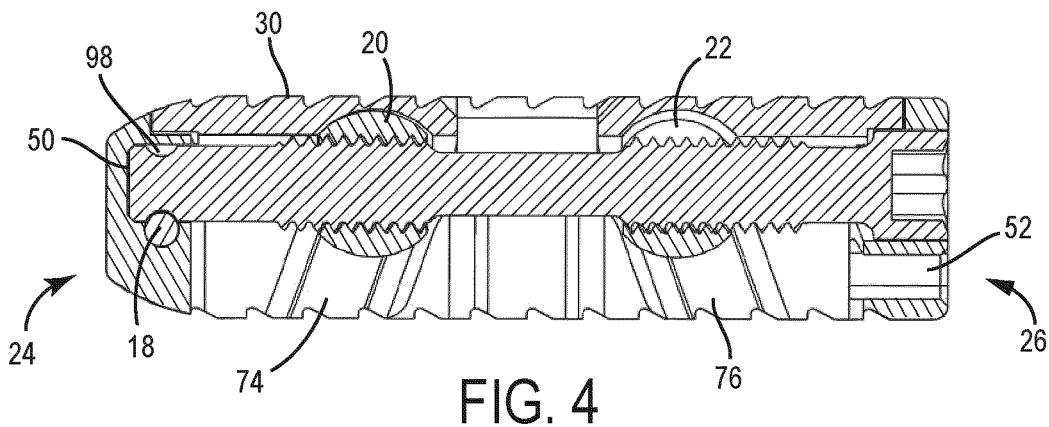
FIG. 4 is a side cross-sectional view of the implant of FIG. 1 in a collapsed position according to one embodiment.
Figure 5:
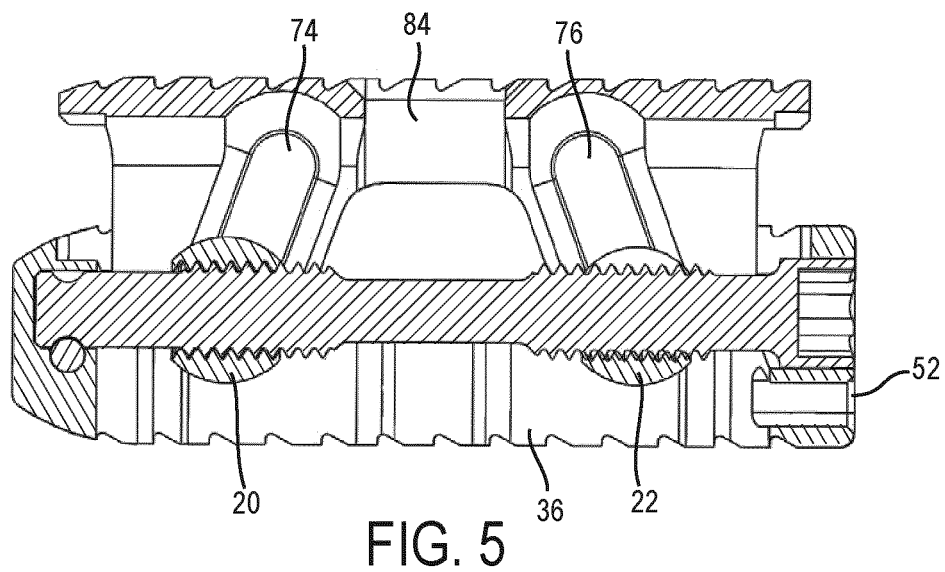
FIG. 5 is a side cross-sectional view of the implant of FIG. 1 in an expanded position according to one embodiment.

Referring to FIGS. 4-6, in one embodiment, the adjustable member 14 includes one or more control channels, such as a first control channel 74 and a second control channel 76. The first control channel 74 receives the first control member 20, and the second control channel 76 receives the second control member 22. In some embodiments, the control members 20, 22 are received in the control channels 74, 76 in a sliding manner such that the control members 20, 22 are able to translate within the control channels 74, 76. In further embodiments, each control channel has a shape such that the control channel surrounds the control member and at least partially corresponds in shape to the control member.

Referring back to FIG. 3, the control shaft 16 includes a head portion 90, a tool port 92 disposed within the head portion 90, and a retention groove 98 located at an end opposite the head portion 90. In some embodiments, the control shaft 16 further includes a first control thread 94 and a second control thread 96. A non-threaded portion 100 may be located between the first control thread 94 and the second control thread 96.

The first control member 20 includes a body 102, one or more flat portions 104, and a first internal thread 106. The second control member 22 includes a body 108, one or more flat portions 110, and a second internal thread 112. In some embodiments, the second control member 22 further includes a slotted portion 114 configured to enable passing the second control member 22 over a portion (e.g., non-threaded portion 100) of the control shaft 16. The first control member 20 and the second control member 22 move or translate both along the control shaft 16 and within or on the first control channel 74 and the second control channel 76.

Referring back to FIGS. 1 and 2, implant 10 is movable between a first, collapsed position, as shown in FIG. 1, to a second, expanded position, shown in FIG. 2. In the first position, the adjustable member 14 is received within the central cavity 36 of the base member 12. The dovetail projections 86, 88 on the adjustable member 14 are received within the dovetail recesses 58, 60 in the base member 12 (see FIG. 6). In some embodiments, the projections and recesses have a relatively close fit to enable proper alignment between the adjustable member 14 and the base member 12, while in other embodiments, the projections and recesses have a relatively loose fit to enable a desired angular offset between the adjustable member 14 and the base member 12.

Referring to FIGS. 3-6, the control shaft 16 is received by the base member 12 such that the retention groove 98 is positioned with the first end 24 of the base member 12 and the head portion 90 is positioned within the second end 26 of the base member 12. In one embodiment, the control shaft 16 is rotatable within the base member 12, and the retention pin 18 extends through the first end 24 and into the retention groove 98 of the control shaft 16 to enable rotation of the control shaft 16 while inhibiting translation of the control shaft 16 relative to the base member 12. The first control member 20 is received on the first control thread 94 of the control shaft 16, and the second control member 22 is received on the second control thread 96 of the control shaft 16. To facilitate assembly of implant 10, in some embodiments, the slot 114 enables passage of the second control member 22 over the non-threaded portion 100 of the control shaft 16 and subsequent threading of the second control member 22 onto the second control thread 96.

In one embodiment, the first control thread 94 and the second control thread 96 are threaded in opposite manners (e.g., left-handed and right-handed), such that upon rotation of the control shaft 16, the control members 20, 22 move in opposite directions along the control shaft 16. For example, the control shaft may be configured that rotation of the control shaft 16 in a first direction (e.g., clockwise) causes the first and second control members 20, 22 to move toward each other, and rotation of the control shaft 16 in a second direction (e.g., counter-clockwise) causes the first and second control member 20, 22 to move away from each other.

As shown in FIGS. 4 and 5, as the control members 20, 22 move along the control shaft 16, the control members 20, 22 further move within the control channels 74, 76, thereby causing relative movement of the adjustable member 14 and the base member 12. For example, FIGS. 4 and 5 show the control members 20, 22 moving away from each other along the control shaft 16. As the control members 20, 22 translate along the control shaft 16, the adjustable member 14 is moved upward or downward due to the angled shape of the first and second control channels 74, 76. The rate of movement of the control members 20, 22, and therefore the adjustable member 14, can be adjusted by modifying the slope of the control channels 74, 76 relative to the control shaft 16.

Figure 9A:
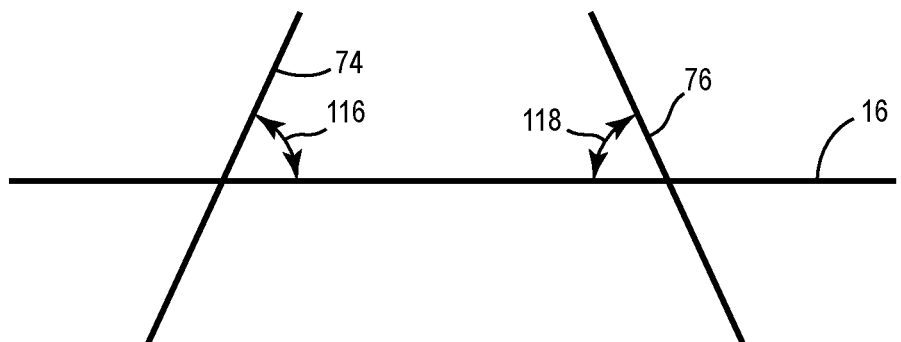
FIG. 9A is a schematic view of a control scheme usable with the implants disclosed herein according to one embodiment.
Figure 9B:
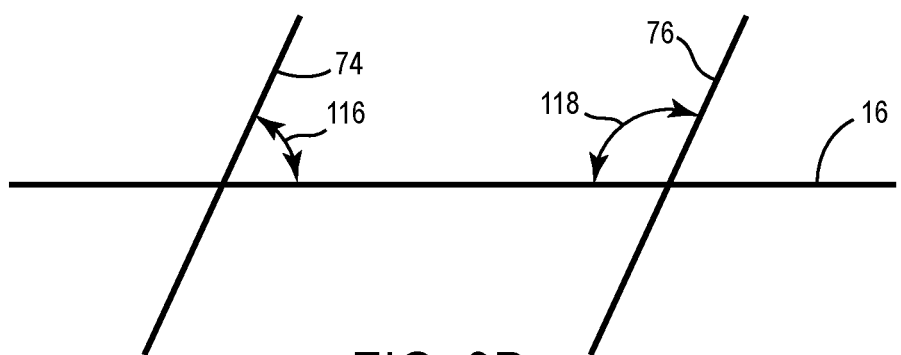
FIG. 9B is a schematic view of a control scheme usable with the implants disclosed herein according to another embodiment.
Figure 9C:
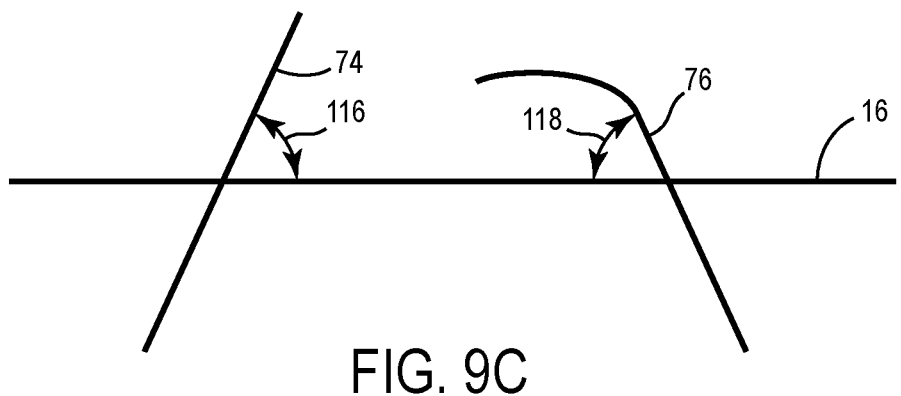
FIG. 9C is a schematic view of a control scheme usable with the implants disclosed herein according to another embodiment.

For example, referring to FIGS. 9A-9C, schematic representations of the control shaft 16, the first control channel 74, and the second control channel 76 are shown according to various alternative embodiments. The first control channel 74 extends at a first angle 116 relative to the control shaft 16, and the second control channel 76 extends at a second angle 118 relative to the control shaft 16. The first and second angles 116, 118 define the rate at which first control member 20 and second control member 22 cause corresponding movement (e.g., expansion) of the first and second ends 62, 64 of the adjustable member 14 relative to the base member 12. As shown in FIG. 9A, in some embodiments, the first angle 116 and second angle 118 are approximately the same, and the control channels 74, 76 define linear paths, such that the rates of movement of the first and second ends 62, 64 of the adjustable member 14 are substantially the same and constant (assuming a constant rate of rotation of the control shaft 16). As shown in FIG. 9B, in some embodiments, rather than being angled toward each other in an upward direction, the first and second control channels 74, 76 may extend in a parallel manner or be configured to extend upward at angles in the same general direction. In yet further embodiments, one or both of the control channels 74, 76 may define a non-linear channel. For example, as shown in FIG. 9C, the second control channel 76 defines a curved path, thereby providing a changing rate of movement of the second end 64 of adjustable member 14. In further alternative embodiments, angles 116, 118 may differ from each other to provide different amounts of movement and to suit a particular application.

Providing differing configurations for the first control channel 74 and the second control channel 76 enables customization of the characteristics of the implant 10 in the second, expanded position. For example, the control channels 74, 76 may be configured such that in a fully expanded position of implant 10, one of the first end 62 and the second end 64 of the adjustable member 14 is expanded to a greater degree than the opposing end. An example of such a configuration is reflected in FIG. 9C, and shown in greater detail with the embodiment of FIGS. 27-34. Other configurations of the first and second control channels 74, 76 are possible according to various alternative embodiments.

In use, implant 10 is positioned within a desired space (e.g., between adjacent portions of bone) while in the first, collapsed position, as shown in FIG. 1. To position implant 10, an appropriate tool may be used to engage tool recesses 56 and manipulate implant 10 into a desired position. Once in a desired position, a subsequent tool may be utilized to engage tool port 92 and rotate control shaft 16 to move adjustable member 14 to a desired degree of expansion. It should be noted that based on a particular application, the adjustable member 14 may be utilized in a fully collapsed position, a fully expanded position, or any intermediate position therebetween. Once implant 10 is properly positioned and expanded to a desired height, bone graft material may be delivered by way of, for example, access aperture 52 and placed into central cavity 36. The various apertures in and through the base member 12 and adjustable member 14 may in some embodiments facilitate the growth of bone material in and around implant 10 to further stabilize the device.

It should be noted that implant 10 may share various features with the other implants described herein, and be made of the same, similar, or different materials. For example, various components of implant 10 may be made of metal, plastic, composites, or other suitable bio-compatible materials. Further, implant 10 may be usable in connection with the spine or other parts of the body.

Referring now to FIGS. 10-19, an expandable implant 610 is shown according to an exemplary embodiment. Implant 610 may share many of the features of the other inter/intrabody implants discussed elsewhere herein. All such combinations of features are to be understood to be within the scope of the present disclosure. Implant 610 is generally similar to the other implants disclosed herein in structure and function except that implant 610 utilizes a single control member/control channel configuration, and further utilizes a pivot pin about which an adjustable member pivots relative to a base member.

Figure 10:
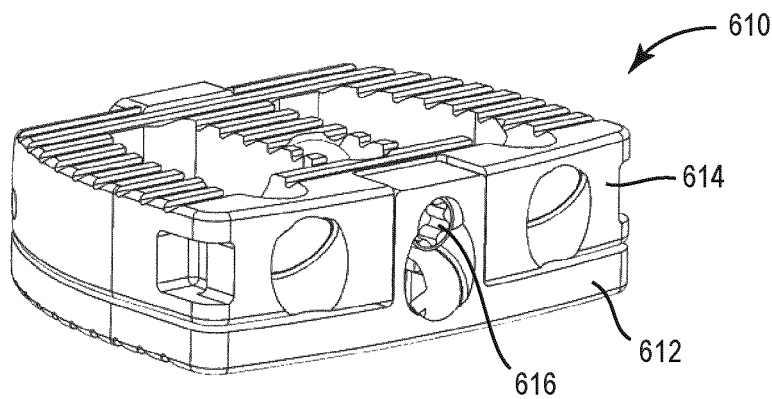
FIG. 10 is a side perspective view of an implant in a collapsed position according to another embodiment.
Figure 11:
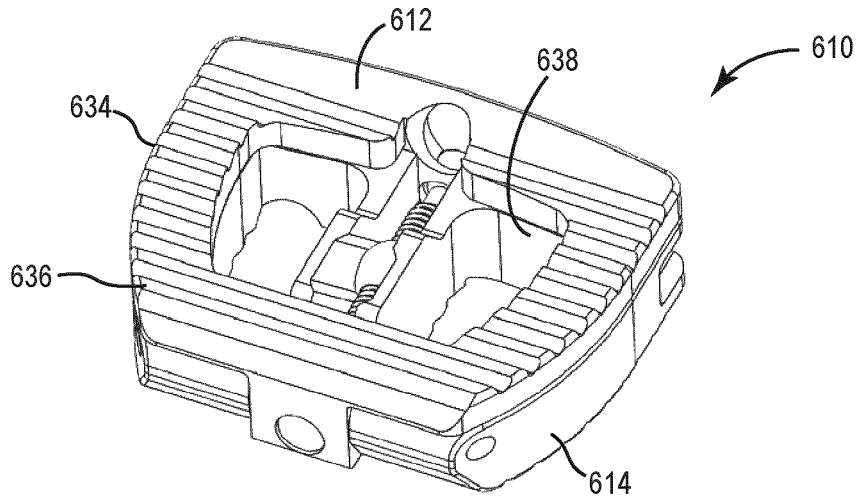
FIG. 11 is a bottom perspective view of the implant of FIG. 10 according to one embodiment.
Figure 12:
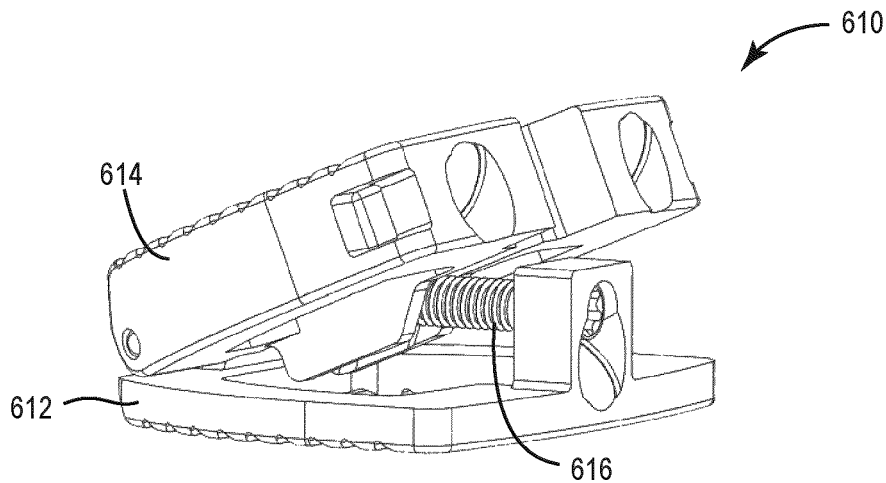
FIG. 12 is a perspective view of the implant of FIG. 35 in an expanded position according to one embodiment.
Figure 13:
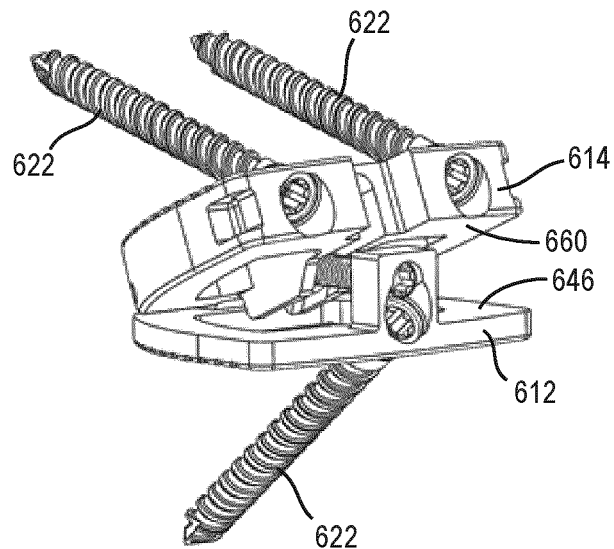
FIG. 13 is perspective view of the implant of FIG. 10 in an expanded position with bone screws according to one embodiment.

According to an exemplary embodiment, implant 610 includes a base member 612 and an adjustable member 614 adjustably coupled to the base member 612. A control shaft 616 is received by the base member 612 and is retained by a retention pin 618 (e.g., a pivot pin or member, retaining pin) passing through a portion of the base member 612 and/or the adjustable member 614. A control member 620 is received on the control shaft 616 and is movable along the control shaft 616 to adjust a position of the adjustable member 614 between a collapsed position, as shown in FIGS. 10 and 11, and an expanded position, as shown in FIGS. 12 and 13.

In one embodiment, the base member 612 includes a front or first end 624, a rear or second end 626, and a central cavity 638 disposed between the first end 624 and the second end 626. The base member 612 further includes a top surface 646 and a bottom surface 634 opposite the top surface 646 and having ridges or projections 636 formed by corresponding grooves. The projections 636 are configured to engage adjacent portions of bone. The base member 612 further includes a planar portion 628. A first extension 630 is positioned at the first end 624 and extends upward from the planar portion 628, and a second extension 632 is positioned at the second end 626 and extends upward from the planar portion 628. A pin aperture 640 extends through the first extension 630 and is configured to receive the retention pin 618 (e.g., in a press fit, sliding, or other manner). The second extension 632 includes a bone screw bore 650 configured to receive a bone screw 622. The first extension 630 includes a first control bore 642 and the second extension includes a second control bore 644. Control bores 642, 644 receive opposing ends of the control shaft 616.

Figure 43:
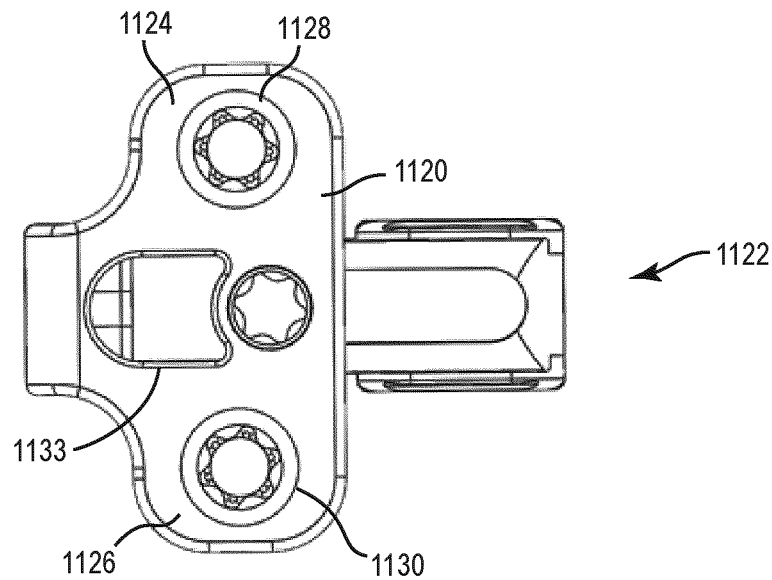
FIG. 43 is a front view of the implant of FIG. 41 in an expanded position according to one embodiment.
Figure 44:
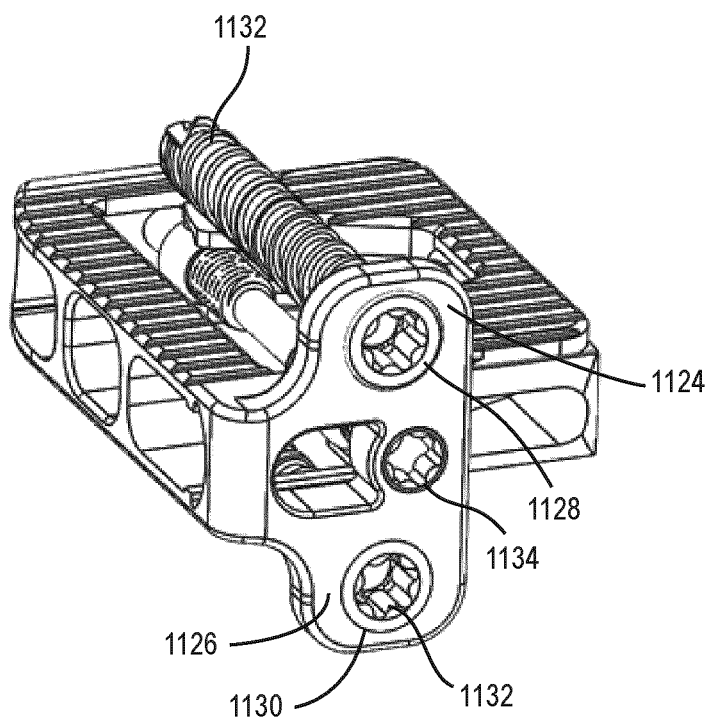
FIG. 44 is a perspective view of the implant of FIG. 41 in an expanded position with bone screws inserted according to one embodiment.

In one embodiment, the adjustable member 614 includes a front or first end 652, a rear or second end 654, and cavities 664 extending through the adjustable member 614 and positioned between the first end 652 and the second end 654. The adjustable member 614 further includes a top surface 656 having ridges or projections 658 formed by corresponding grooves, and a bottom surface 660. The adjustable member 614 further includes pin apertures 668 configured to receive the retention pin 618 to enable movement (e.g., pivoting) of the adjustable member 614 relative to the base member 612. Further, the adjustable member includes a first bone screw support portion 670 including a bone screw bore 674 and a second bone screw support portion 672 having a bone screw bore 676. As shown in FIG. 43, the first and second bone screw support portions 670, 672 of the adjustable member 614 and the second extension 632 of the base member 612 collectively form a front face of the implant 610, such that the control shaft 616 and the bone screws 622 are accessible via the front face of the implant 610 (e.g., when the implant 610 is in a collapsed position).

Figure 14:
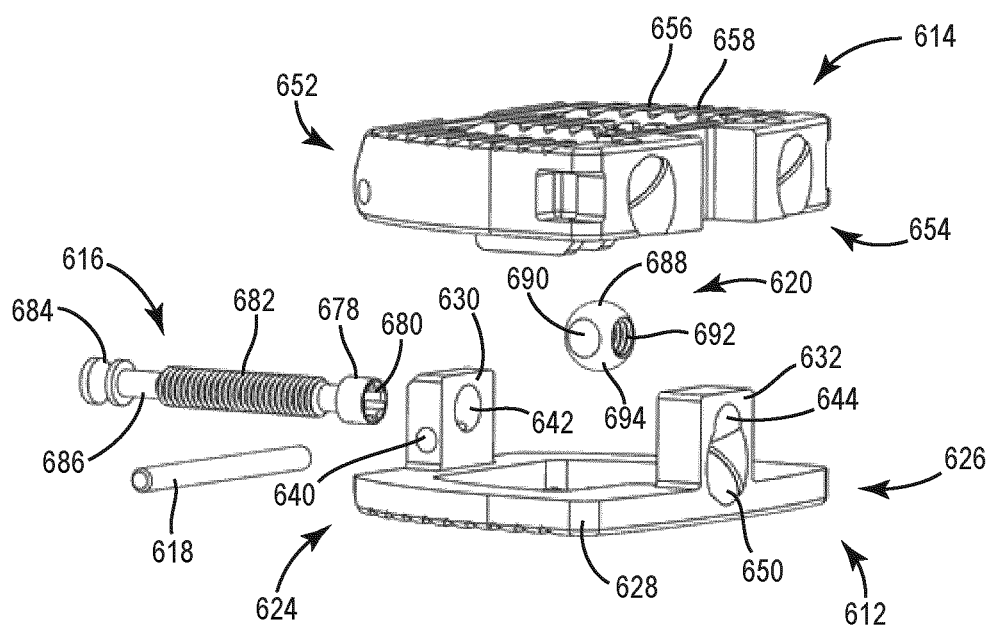
FIG. 14 is an exploded view of the implant of FIG. 10 according to one embodiment.
Figure 15:
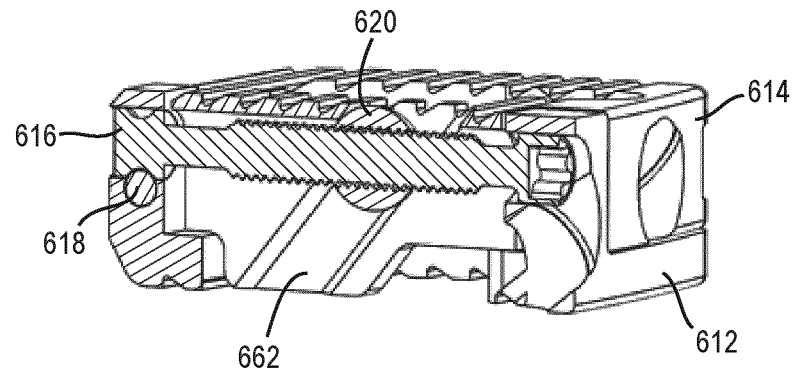
FIG. 15 is a cross-section view of the implant of FIG. 10 in a collapsed position according to one embodiment.
Figure 16:
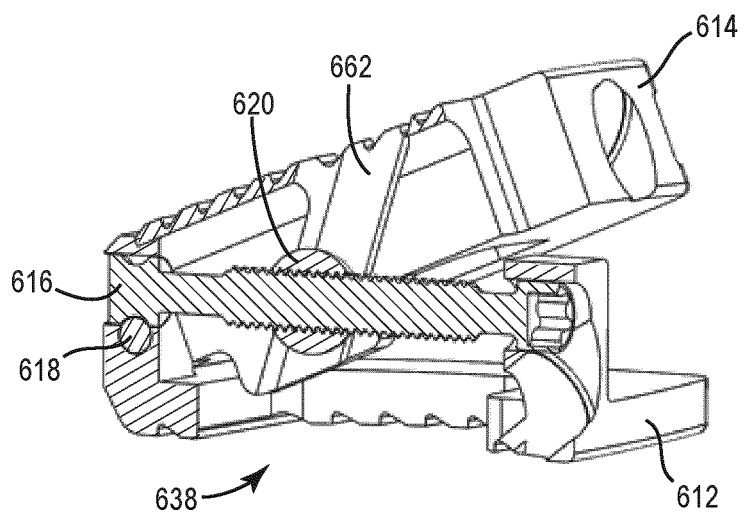
FIG. 16 is a cross-section view of the implant of FIG. 10 in an expanded position according to one embodiment.
Figure 17:
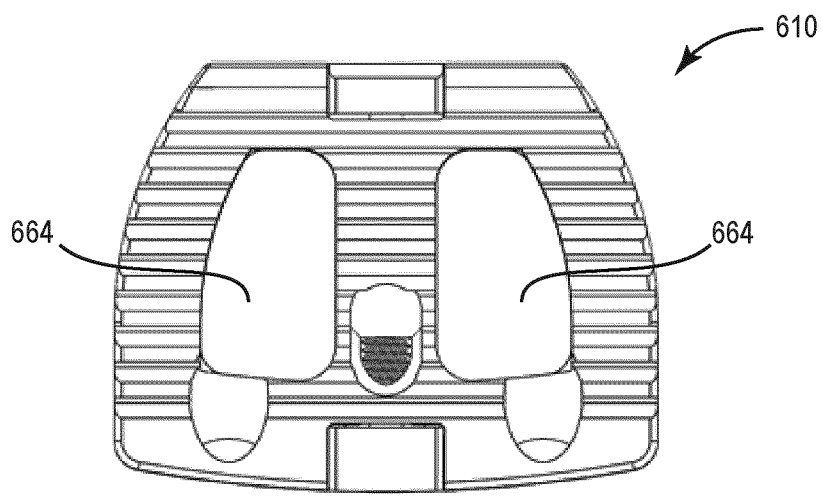
FIG. 17 is a top view of the implant of FIG. 10 according to one embodiment.
Figure 18:
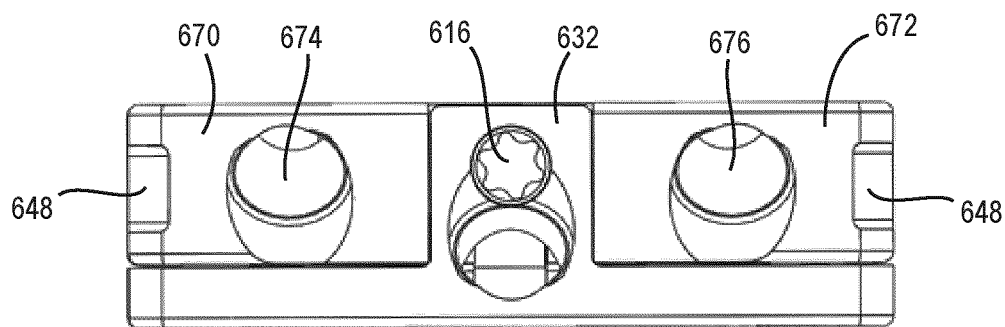
FIG. 18 is a front view of the implant of FIG. 10 according to one embodiment.
Figure 19:
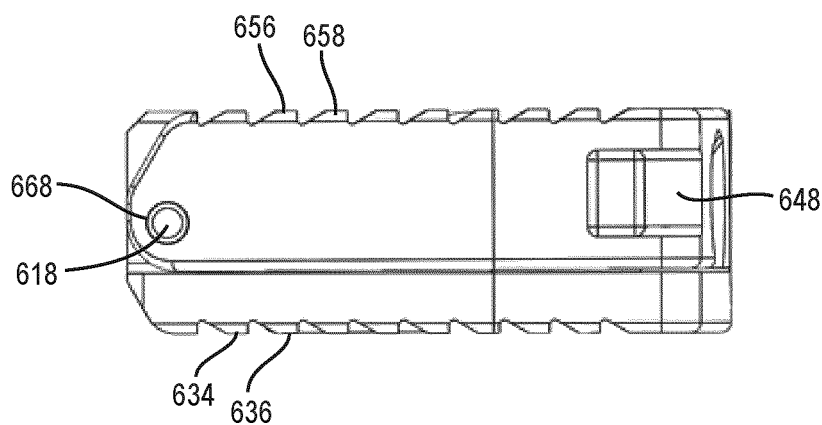
FIG. 19 is a side view of the implant of FIG. 10 according to one embodiment.

Referring to FIGS. 14-16, in one embodiment, the adjustable member 614 includes one or more control channels, such as control channel 662. The control channel 662 receives the control member 620. In some embodiments, the control member 620 is received in the control channel 662 in a sliding manner such that the control member 620 is able to translate within the control channel 662. In further embodiments, the control channel 662 has a shape such that the control channel 662 surrounds the control member 620 and at least partially corresponds in shape to the control member 620.

Referring to FIG. 14, the control shaft 616 includes a head portion 678, a tool port 680 disposed within the head portion 678, and a retention groove 684 located at an end opposite the head portion 678. In some embodiments, the control shaft 616 further includes a control thread 682. Non-threaded portions 686 may be located on one or both side of the control thread 682.

The control member 620 includes a body 688, one or more flat portions 690, and an internal thread 692. In some embodiments, the control member 620 further includes a slotted portion configured to enable passing the control member 620 over a portion (e.g., non-threaded portion 686) of the control shaft 616. The control member 620 moves or translates both along the control shaft 616 and within or on the control channel 662.

Referring to FIGS. 15 and 16, the control shaft 616 is received by the base member 612 such that the retention groove 684 is positioned with the first extension 630 of the base member 612 and the head portion 678 is positioned within the second extension 632 of the base member 612. In one embodiment, the control shaft 616 is rotatable within the base member 612, and the retention pin 618 extends through the first extension 630 and into the retention groove 684 of the control shaft 616 to enable rotation of the control shaft 616 while inhibiting translation of the control shaft 616 relative to the base member 612. The internal thread 692 of the control member 620 is received on the control thread 682 of the control shaft 616 such that as the control member 620 moves along the control shaft 616, the control member 620 further moves within the control channel 662, thereby causing relative movement (e.g., pivotal movement) of the adjustable member 614 relative to the base member 612 (e.g., about retention pin 618). For example, FIGS. 15 and 16 show the control member 620 moving along the control shaft 616. As the control member 620 translates along the control shaft 616, the adjustable member 614 pivots about the retention pin 618. The rate of movement of the control member 620, and therefore the adjustable member 614, can be adjusted by modifying the slope of the control channel 662 relative to the control shaft 616.

In use, implant 610 is positioned within a desired space (e.g., between adjacent portions of bone) while in the first, collapsed position, as shown in FIG. 10. To position implant 610, an appropriate tool may be used to engage tool recesses 648 and manipulate implant 610 into a desired position. Once in a desired position, a subsequent tool may be utilized to engage tool port 680 and rotate control shaft 616 to pivot adjustable member 614 to a desired degree of expansion. It should be noted that based on a particular application, the adjustable member 614 may be utilized in a fully collapsed position, a fully expanded position, or any intermediate position therebetween. One or more bone screws 622 may be screwed into adjacent portions of bone as shown in FIG. 13. Once implant 610 is properly positioned and expanded to a desired height, bone graft material may be delivered by way of, for example, apertures 664 or alternatively, by the space formed due to the expansion of adjustable member 614. The various apertures in and through the base member 612 and adjustable member 614 may in some embodiments facilitate the growth of bone material in and around implant 610 to further stabilize the device.

It should be noted that implant 610 may share various features with the other implants described herein, and be made of the same, similar, or different materials. For example, various components of implant 610 may be made of metal, plastic, composites, or other suitable bio-compatible materials. Further, implant 160 may be usable in connection with the spine or other parts of the body.

Referring now to FIGS. 20-29, an expandable implant 710 is shown according to an exemplary embodiment. Implant 710 may include any of the features shown and described with respect to the other expandable implants disclosed herein. For example, implant 710 is in many ways similar to implant 10, and may include any of the features of implant 10. Implant 710 is usable, for example, between and/or within vertebral bodies of the spine, and may share many of the features of the other inter/intra-body implants discussed elsewhere herein. It should be understood that implant 710 may in some embodiments be usable in other portions of the body in addition to the spine, and all such applications are to be understood to be within the scope of the present disclosure.

Figure 20:
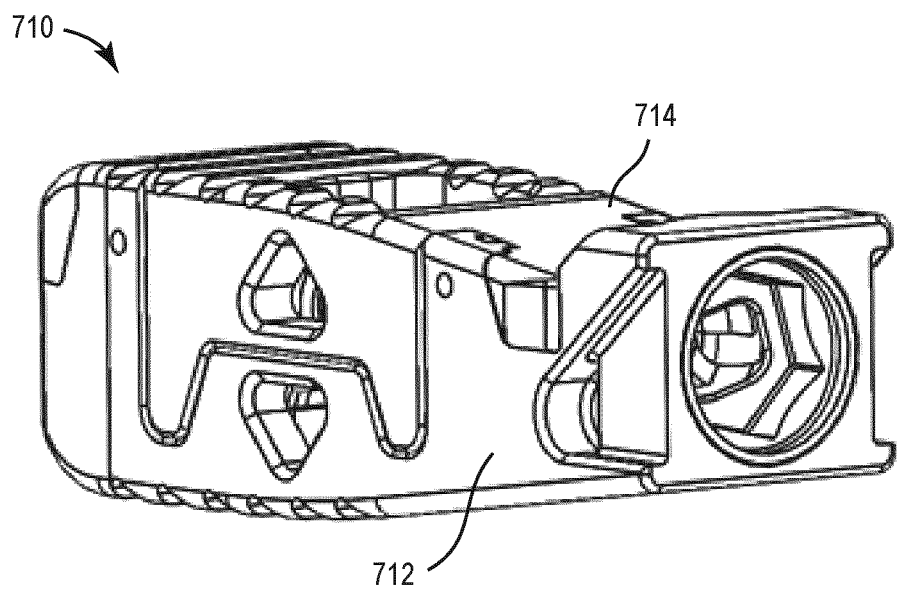
FIG. 20 is a perspective view of an implant in a collapsed position according to one embodiment.
Figure 21:
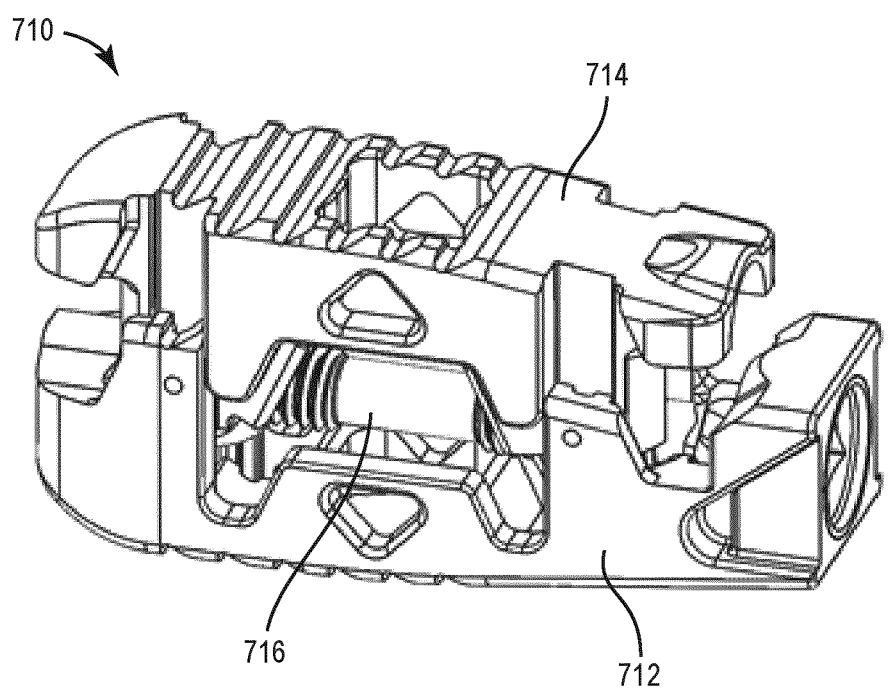
FIG. 21 is a perspective view of the implant of FIG. 20 in an expanded position according to one embodiment.
Figure 22:
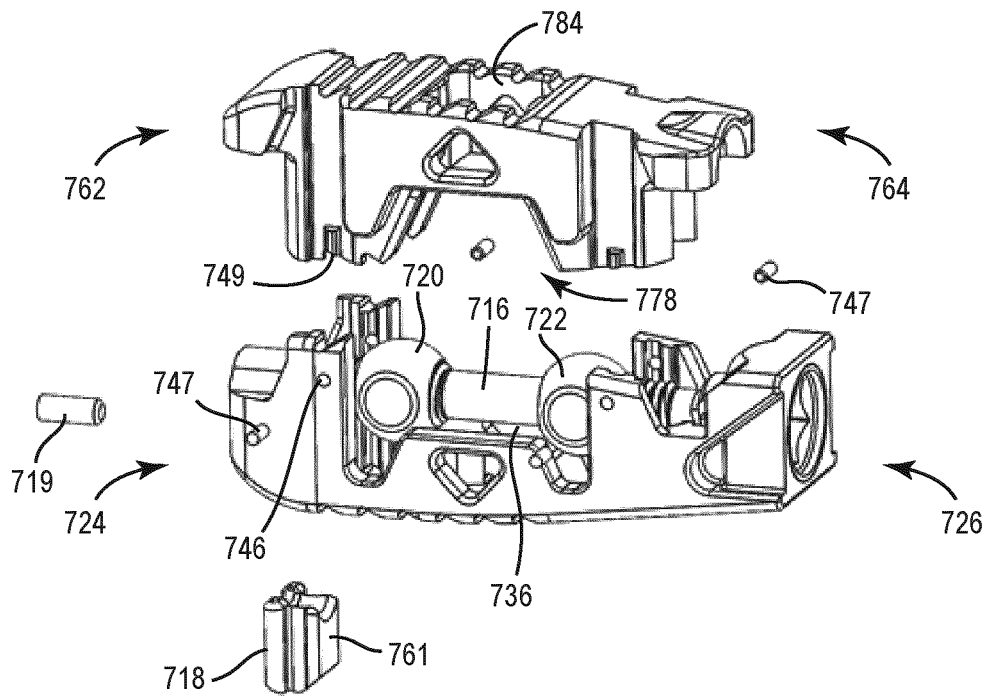
FIG. 22 is a partial exploded view of the implant of FIG. 20 according to one embodiment.
Figure 23:
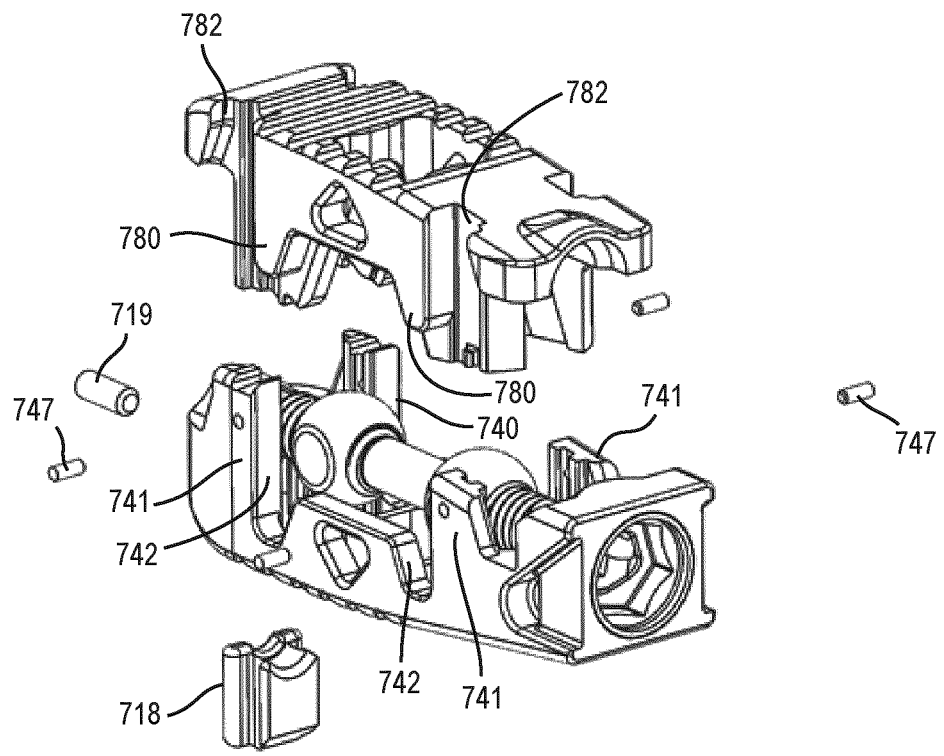
FIG. 23 is a partial exploded view of the implant of FIG. 20 according to one embodiment.
Figure 29:
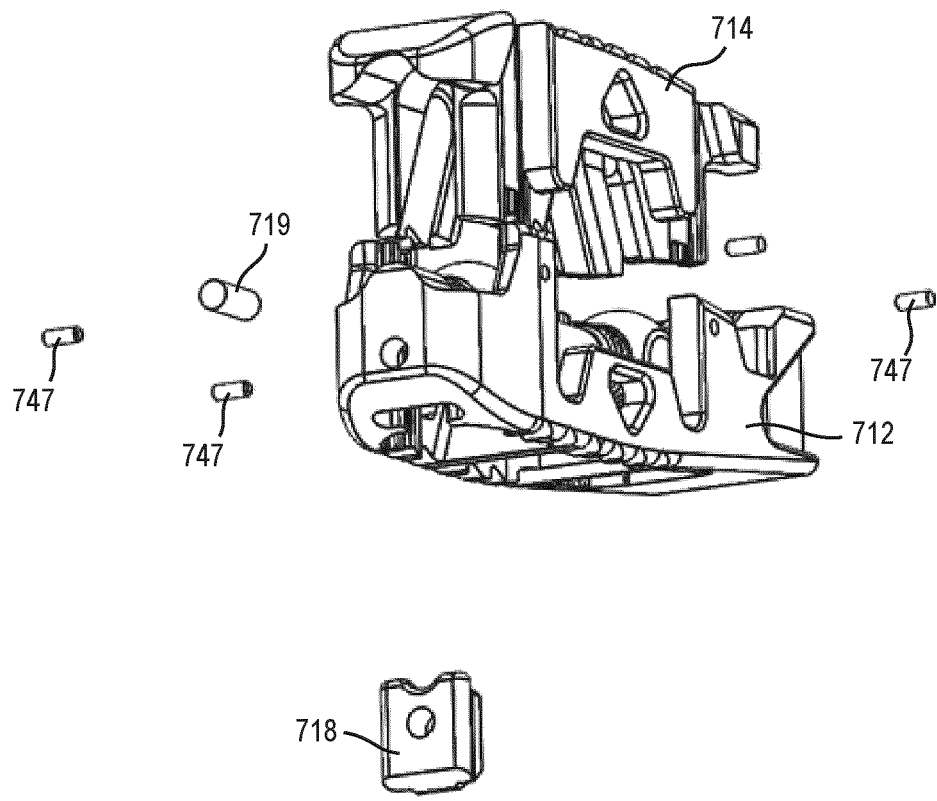
FIG. 29 is a partial exploded view of the implant of FIG. 20 according to one embodiment.

According to an exemplary embodiment, implant 710 includes a base member 712 and an adjustable member 714 adjustably coupled to the base member 712. A control shaft 716 is received by the base member 712 and is retained by a retention member 718 passing through a portion of the base member 712. Retention member 718 is in turn retained in place by a retention pin 719, which may further be welded, press-fit, or otherwise secured in place, as shown in FIG. 29. A first control member 720 and a second control member 722 are received on the control shaft 716 and are movable along the control shaft 716 to adjust a position of the adjustable member 714 between a collapsed position, as shown in FIG. 20, and an expanded position, as shown in FIG. 21.

In one embodiment, the base member 712 includes a front or first end 724, a rear or second end 726, and a central cavity 736 disposed between the first end 724 and the second end 726. The base member 712 further includes a top surface 728, a bottom surface 732 opposite the top surface 728 and having ridges or projections 734 formed by corresponding grooves, a first side 738, and a second side 740. The projections 734 are configured to engage adjacent portions of bone. The base member 712 further includes alignment guides 742 and alignment recesses 744, which engage corresponding guides and recesses on adjustable member 714. Limiting pin apertures 746 extends through one or both of first side 738 and second side 740 and are configured to receive limiting pins 747 (e.g., in a press fit or other manner). Limiting pins 747 engage corresponding projections 749 on adjustable member 714 to limit an amount of expansion of adjustable member 714 relative to base member 712. The second end 726 of the base member 712 includes a control bore 748 configured to receive a first portion of the control shaft 716. The first end 724 of the base member 712 includes a control counterbore 750 (see FIG. 25) configured to receive a second portion of the control shaft 716.

In one embodiment, the adjustable member 714 includes a front or first end 762, a rear or second end 764, and a central recess or cavity 778 positioned between the first end 762 and the second end 764. A top cavity 784 (see FIG. 5) in the adjustable member 714 extends to the central cavity 778. The adjustable member 714 further includes a top surface 766 having ridges or projections 768 formed by corresponding grooves, and a bottom surface 770 including ridges or projections 772 (see FIG. 27) formed by corresponding grooves. Alignment guides 780 and alignment recesses 782 are received by alignment recesses 742 and alignment guides 741 of base member 712 to maintain a desired alignment between the base member 712 and the adjustable member 714 (e.g., to provide linear relative movement, permit non-linear relative movement, etc.). In one embodiment, projections 749 are disposed within recesses 782 and are configured to engage limiting pins 747 to limit an amount of expansion of adjustable member 714 relative to base member 712.

Figure 25:
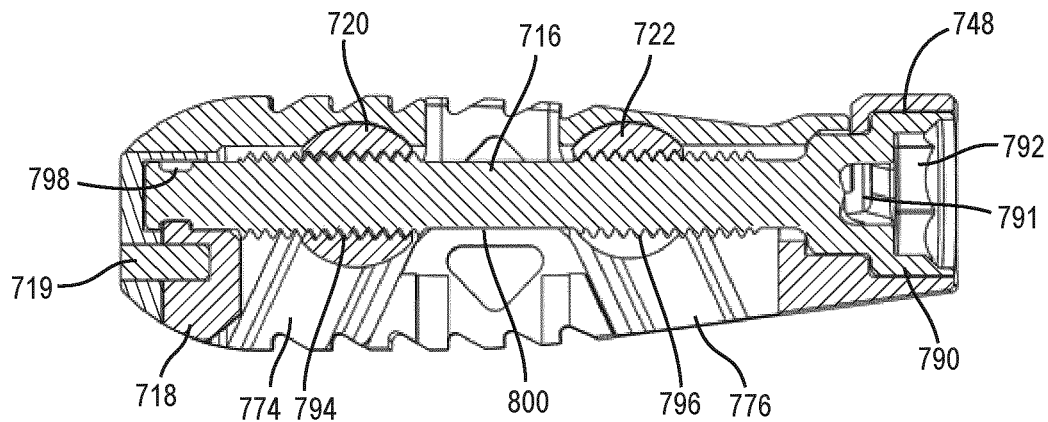
FIG. 25 is a cross-section view of the implant of FIG. 20 according to one embodiment.
Figure 26:
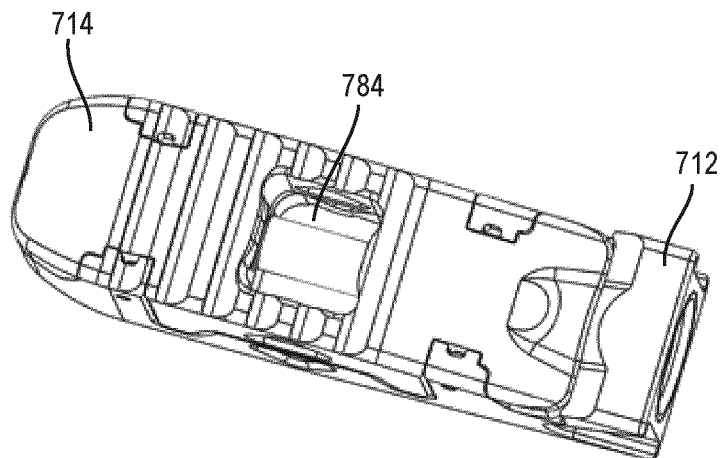
FIG. 26 is a top perspective view of the implant of FIG. 20 according to one embodiment.
Figure 27:
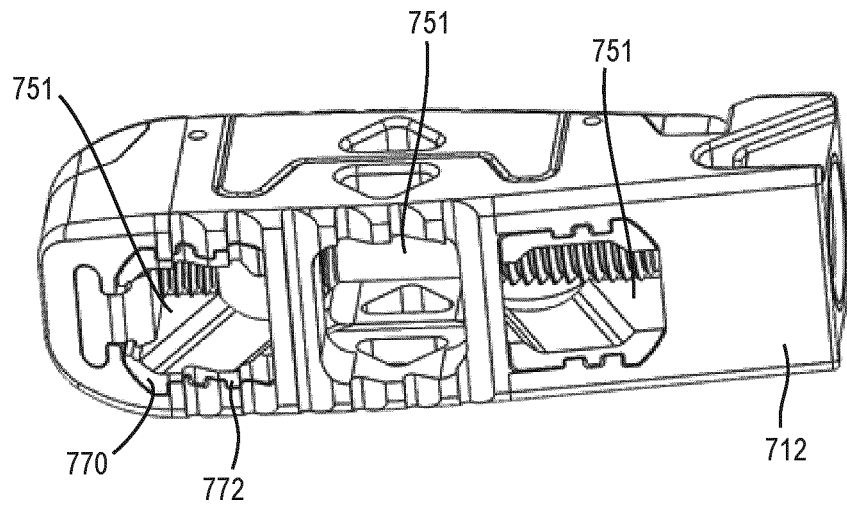
FIG. 27 is a bottom perspective view of the implant of FIG. 20 according to one embodiment.
Figure 28:
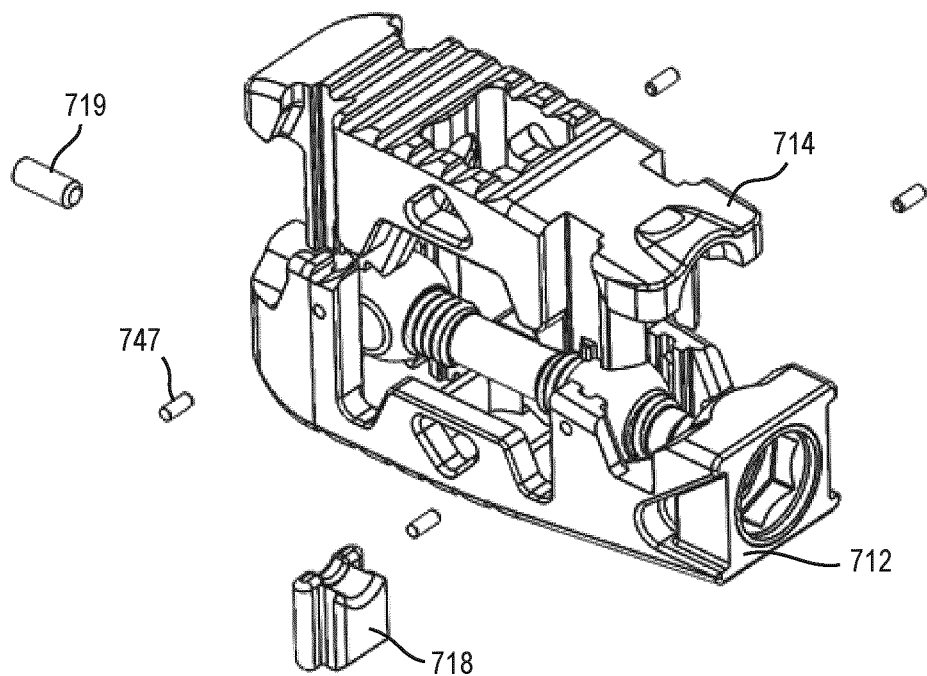
FIG. 28 is a partial exploded view of the implant of FIG. 20 according to one embodiment.

Referring to FIG. 25, in one embodiment, the adjustable member 714 includes one or more control channels, such as a first control channel 774 and a second control channel 776. The first control channel 774 receives the first control member 720, and the second control channel 776 receives the second control member 722. In some embodiments, the control members 720, 722 are received in the control channels 774, 776 in a sliding manner such that the control members 720, 722 are able to translate within the control channels 774, 776. In further embodiments, each control channel has a shape such that the control channel surrounds the control member and at least partially corresponds in shape to the control member. In some embodiments, retention member 718 includes a surface 761 (see FIG. 22) that acts as a limit surface for first control member 720, such that first control member 720 engages surface 761 at a maximum expansion position for adjustable member 714. As such, surface 761 acts to limit the maximum expansion of adjustable member 714 by limiting the degree of movement of first control member 720 (and therefore second control member 722) along control shaft 716.

Referring further to FIG. 25, the control shaft 716 includes a head portion 790, a tool port 792 disposed within the head portion 790, and a retention groove 798 located at an end opposite the head portion 790. In some embodiments, the control shaft 716 further includes a first control thread 794 and a second control thread 796. A non-threaded portion 800 may be located between the first control thread 794 and the second control thread 796.

Similar to control member 20 (see, e.g., FIGS. 1-8), the first control member 720 includes a body, one or more flat portions, and a first internal thread. Similar to control member 22 (see, e.g., FIGS. 1-8), the second control member 722 includes a body, one or more flat portions, and a second internal thread. In some embodiments, the second control member 722 further includes a slotted portion configured to enable passing the second control member 722 over a portion (e.g., non-threaded portion 800) of the control shaft 716. The first control member 720 and the second control member 722 move or translate both along the control shaft 716 and within or on the first control channel 774 and the second control channel 776.

Referring back to FIGS. 20 and 21, implant 710 is movable between a first, collapsed position, as shown in FIG. 20, to a second, expanded position, shown in FIG. 21.

In the first position, the adjustable member 714 is collapsed against the base member 712. The alignment guides 741 and alignment recesses 742 on base member 712 are received by alignment recesses 780 and alignment guides 782 on adjustable member 714. In some embodiments, the alignment guides and recesses have a relatively close fit to enable proper alignment between the adjustable member 714 and the base member 712, while in other embodiments, the alignment guides and recesses have a relatively loose fit to enable a desired angular offset between the adjustable member 714 and the base member 712.

Referring to FIG. 25, the control shaft 716 is received by the base member 712 such that the retention groove 798 is positioned with the first end 724 of the base member 712 and the head portion 790 is positioned within the second end 726 of the base member 712. In one embodiment, the control shaft 716 is rotatable within the base member 712, and the retention member 718 extends through the first end 724 and into the retention groove 798 of the control shaft 16 to enable rotation of the control shaft 716 while inhibiting translation of the control shaft 716 relative to the base member 712. The first control member 720 is received on the first control thread 794 of the control shaft 716, and the second control member 722 is received on the second control thread 796 of the control shaft 716. To facilitate assembly of implant 710, in some embodiments, a slot enables passage of the second control member 722 over the non-threaded portion 800 of the control shaft 716 and subsequent threading of the second control member 722 onto the second control thread 796 (as discussed with respect to, for example, control member 22 shown in FIGS. 1-8).

In one embodiment, the first control thread 794 and the second control thread 796 are threaded in opposite manners (e.g., left-handed and right-handed), such that upon rotation of the control shaft 716, the control members 720, 722 move in opposite directions along the control shaft 716. For example, the control shaft 716 may be configured such that rotation of the control shaft 716 in a first direction (e.g., clockwise) causes the first and second control members 720, 722 to move toward each other, and rotation of the control shaft 716 in a second direction (e.g., counter-clockwise) causes the first and second control member 720, 722 to move away from each other. In other embodiments, the first and second control members 720, 722 are configured to translate in a same direction upon rotation of control shaft 716.

As shown in FIG. 25, as the control members 720, 722 move along the control shaft 716, the control members 720, 722 further move within the control channels 774, 776, thereby causing relative movement of the adjustable member 714 and the base member 712. As the control members 720, 722 translate along the control shaft 716, the adjustable member 714 is moved upward or downward due to the angled shape of the first and second control channels 774, 776. The rate of movement of the control members 720, 722, and therefore the adjustable member 714, can be adjusted by modifying the slope of the control channels 774, 776 relative to the control shaft 716, as discussed in greater detail with respect to FIGS. 9A-9C.

Providing differing configurations for the first control channel 774 and the second control channel 776 enables customization of the characteristics of the implant 710 in the second, expanded position. For example, the control channels 774, 776 may be configured such that in a fully expanded position of implant 710, one of the first end 762 and the second end 764 of the adjustable member 714 is expanded to a greater degree than the opposing end. Other configurations of the first and second control channels 774, 776 are possible according to various alternative embodiments. All such modifications and features are to be understood to be within the scope of the present disclosure and may form part of any of the expandable implants disclosed herein.

In use, implant 710 is positioned within a desired space (e.g., between adjacent portions of bone) while in the first, collapsed position, as shown in FIG. 20. To position implant 710, an appropriate tool may be used to engage tool recesses 756 and manipulate implant 710 into a desired position. Once in a desired position, a subsequent tool may be utilized to engage tool port 792 and rotate control shaft 716 to move adjustable member 714 to a desired degree of expansion. It should be noted that based on a particular application, the adjustable member 714 may be utilized in a fully collapsed position, a fully expanded position, or any intermediate position therebetween.

Figure 24:
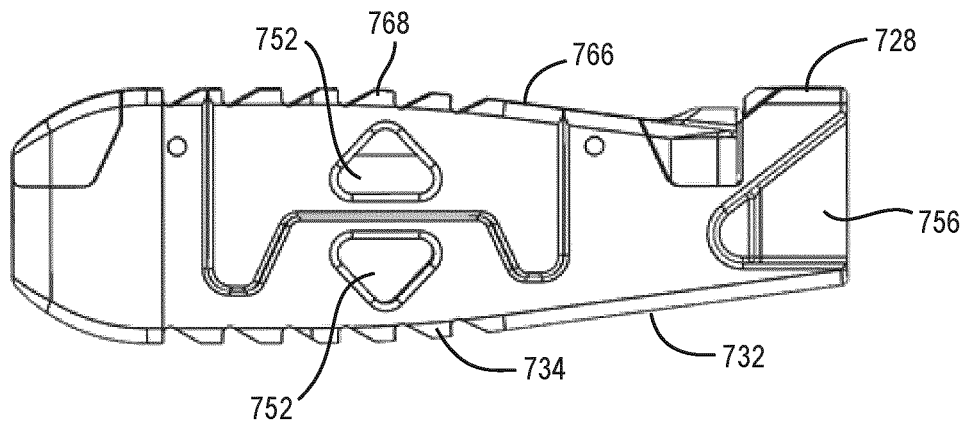
FIG. 24 is a side view of the implant of FIG. 20 according to one embodiment.

Once implant 710 is properly positioned and expanded to a desired height, bone graft material may be delivered by way of, for example, access aperture 752 (see FIG. 24) and placed into central cavity 736. The various apertures in and through the base member 712 and adjustable member 714 may in some embodiments facilitate the growth of bone material in and around implant 710 to further stabilize the device. As shown in FIG. 24, side apertures 752 may extend through one or both sides of the base member 712 and the adjustable member 714 and communicate with an interior of implant 710 to promote bone growth, etc. Similarly, aperture 784 in adjustable member 714 and apertures 751 in the base member 712 provide access to the interior of implant 710 via the top/bottom of implant 710. Further, control member 716 may include an access port 791 accessible by way of tool port 792 that is in fluid communication with the interior of implant 710 and enables delivery of bone graft or other material to the interior of implant 710 (e.g., by way of a tool, etc.).

It should be noted that implant 710 may share various features with the other implants described herein, and be made of the same, similar, or different materials. For example, various components of implant 710 may be made of metal, plastic, composites, or other suitable bio-compatible materials. Further, implant 710 may be usable in connection with the spine or other parts of the body.

Figure 30:
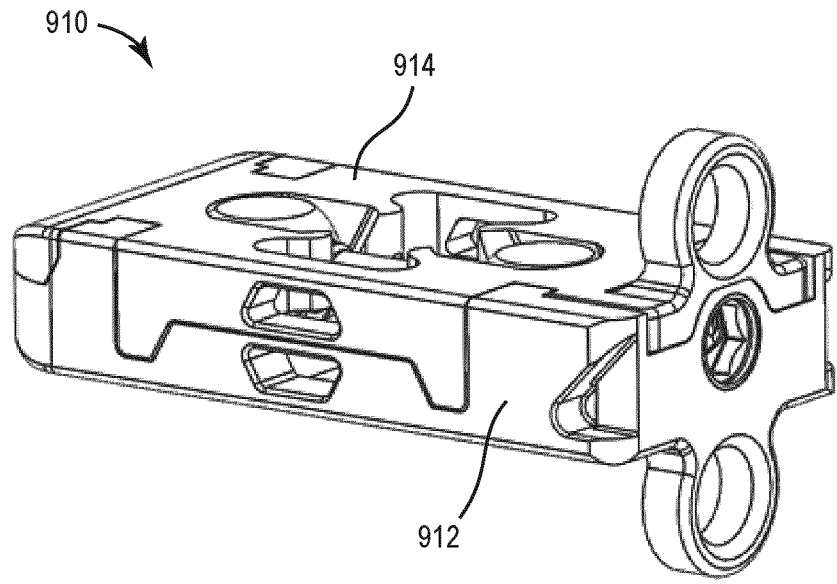
FIG. 30 is a perspective view of an expandable implant in a collapsed position according to another embodiment.
Figure 31:
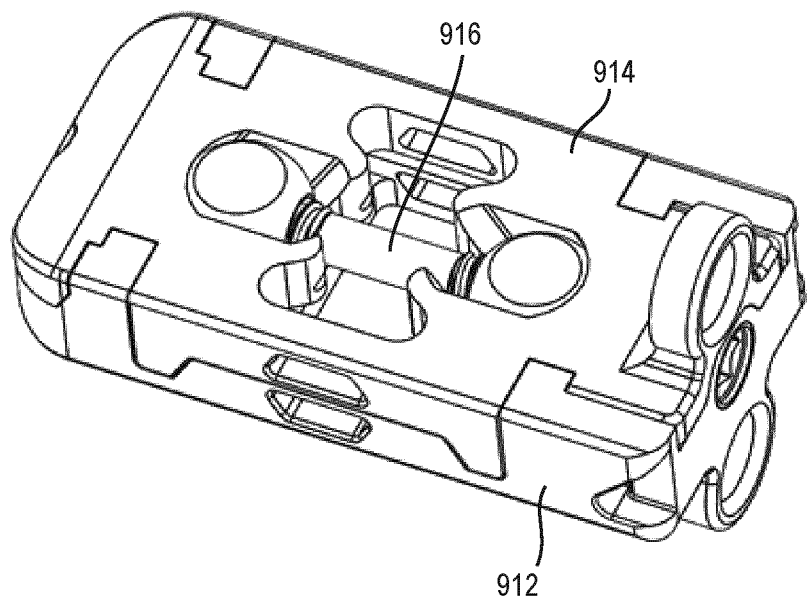
FIG. 31 is another perspective view of the implant of FIG. 30 in a collapsed position according to one embodiment.
Figure 32:
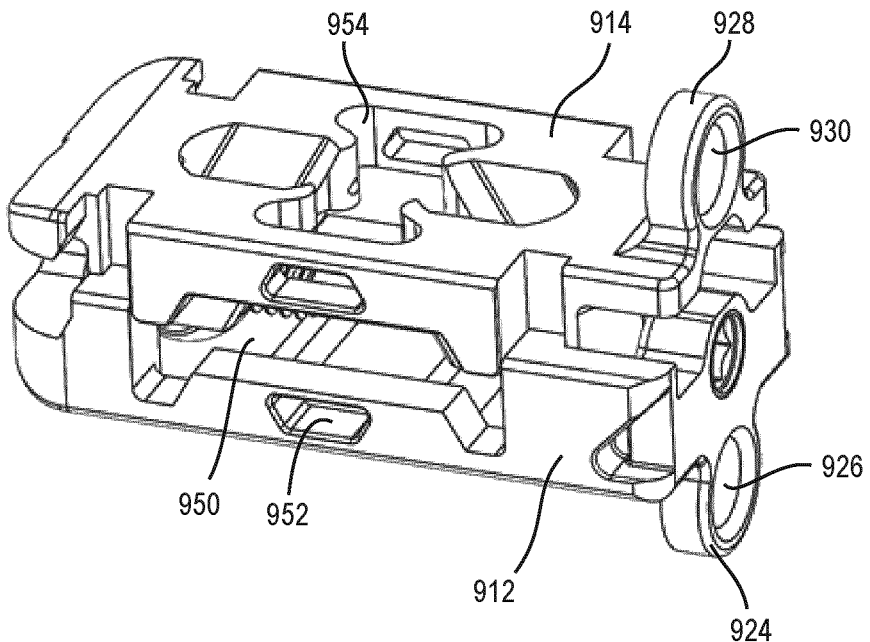
FIG. 32 is a perspective view of the implant of FIG. 30 in an expanded position according to one embodiment.
Figure 33:
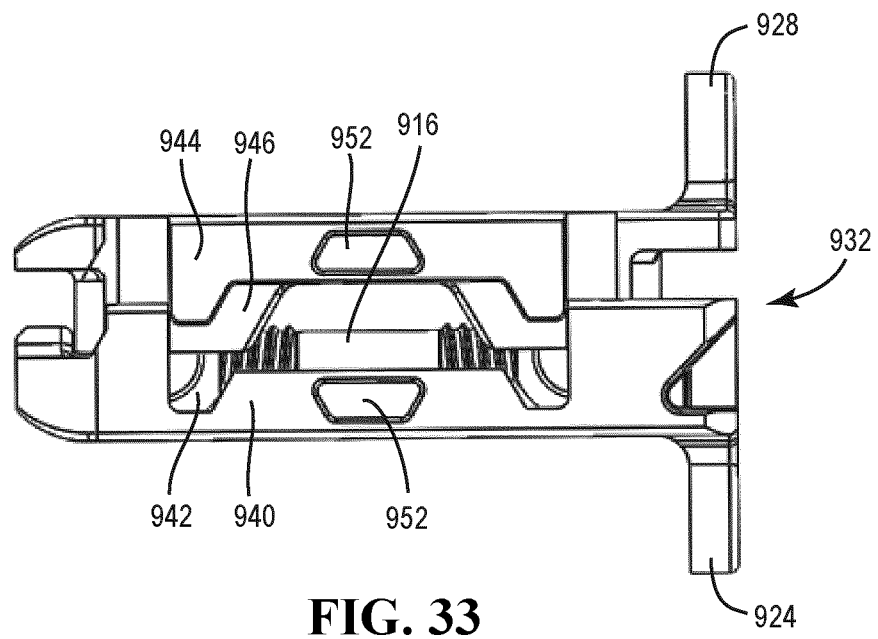
FIG. 33 is a side view of the implant of FIG. 30 in an expanded embodiment.
Figure 34:
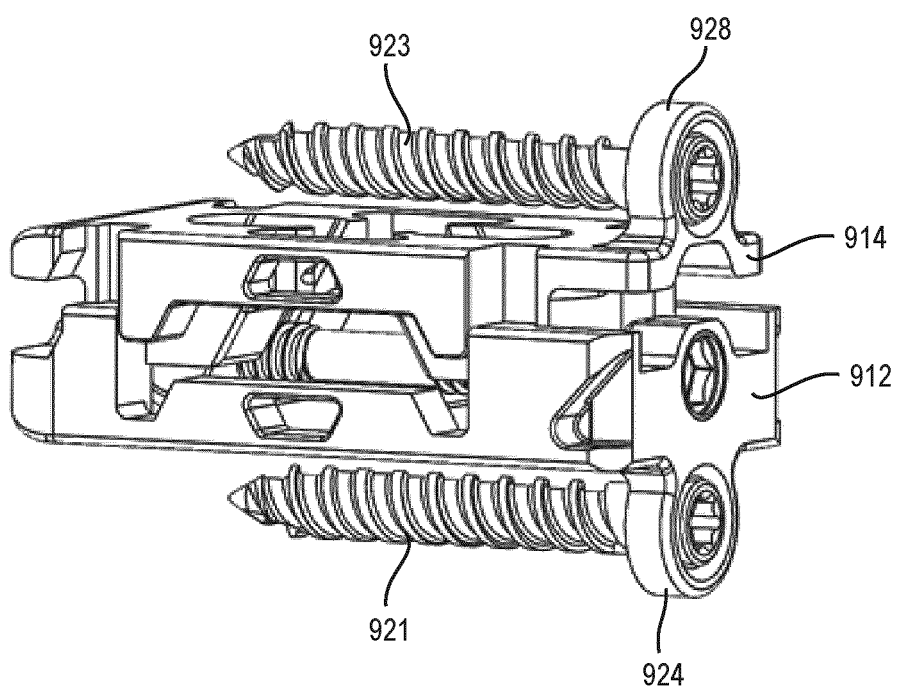
FIG. 34 is a perspective view of the implant of FIG. 30 with bone screws inserted according to one embodiment.

Referring now to FIGS. 30-34, in some embodiments, one or both of a base member or an adjustable member of an implant may be configured to receive a bone screw to further secure the implant to adjacent portions of bone. For example, as shown in FIGS. 30-34, an implant 910 includes a base member 912 and an adjustable member 914 is adjustably coupled to the base member 912. A control shaft 916 is received by the base member 912 and may be retained by a retention pin passing through a portion of the base member 912. A first control member 920 and a second control member 922 are received on the control shaft 916 and are movable along the control shaft 916 to adjust a position of the adjustable member 914 between a collapsed position, as shown in FIGS. 30-31, and an expanded position, as shown in FIGS. 32-34. Bone screws 921, 923 extend through base member 912 and adjustable member 914 (see FIG. 34).

Implant 910 may include any combination of the features disclosed herein with respect to the other implants, and all such combinations of features are to be understood to be within the scope of the present disclosure. In one embodiment, a substantial portion of implant 910 is generally rectangular in shape when in a first, collapsed position. As shown in FIGS. 32-34, in some embodiments, the base member 912 includes a first bone screw support portion or extension 924 having a first bone screw bore 926 configured to receive bone screw 921. Similarly, adjustable member 914 includes a second bone screw support portion or extension 928 having a second bone screw bore 930 configured to receive bone screw 923. The first extension 924 and the second extension 928 collectively form a proximal face 932 (see FIG. 33) for implant 910 with the corresponding end portions of base member 912 and adjustable member 914. As shown in FIG. 33, the first bone screw bore 926, the second bone screw bore 930, and the control shaft 916 are accessible by way of the proximal face 932 of the implant 910.

Referring further to FIG. 33, in some embodiments, extensions 924, 928 extend in generally opposite directions relative to the remaining portions of the base member 912 and the adjustable member 914 (e.g., in a perpendicular fashion, in an angled fashion, etc.). As such, extensions 924, 928 may act as to limit the insertion of implant 910 into a vertebral or other space by way of extensions 924, 928 interfacing with adjacent portions of bone. Furthermore, extensions 924, 928 and bone screw bores 926, 930 may be configured such that bone screws 921, 923 extend in a generally parallel manner to the longitudinal axis of implant 910 (see FIG. 34). This configuration may facilitate fastening screws 921, 923 into adjacent portions of bone due to the alignment of the screws with an incision and/or the implant.

In some embodiments and similar to various other implants disclosed herein, implant 910 may include lower alignment guides 940 and lower alignment recesses 942 provided on base member 912 that are configured to be received by corresponding upper alignment recesses 946 and upper alignment guides 944 provided on adjustable member 914 to maintain a desired alignment (e.g., linear, non-linear, etc.) between adjustable member 914 and base member 912. The alignment guides and recesses may be provide on both sides of implant 910, and any suitable number of guides and recesses may be utilized. Further, implant 910 includes a central cavity 950 that is accessible (e.g., to promote bone growth, to receive bone growth material, etc.) by way of side apertures 952, which may be provide on one or both sides of base member 912 and/or adjustable member 914. Implant may further include a top aperture 954 to provide access to the central cavity 950.

As shown in FIGS. 30-34, implant 910 may have a relatively flat profile, such that the width of the implant 910 is substantially greater than the height of the main portion or body of implant 910 excluding the extensions 924, 928. For example, in various embodiments the width of the main body of implant 910 may be two, three, four, or more times the height. A flatter profile may provide a more stable implant. Furthermore, in some embodiments, in the collapsed position, as shown in FIG. 31, the first and second control members 920, 922 may be flush with or adjacent the top and/or bottom surfaces of implant 910, and the corresponding control channels may open up to the top and/or bottom surfaces of implant 910.

It should be noted that the implant 910 may share various features with the other implants described herein, and be made of the same, similar, or different materials. For example, various components of the implant 910 may be made of metal, plastic, composites, or other suitable biocompatible materials. Further, the implant 910 may be usable in connection with the spine or other parts of the body.

Referring now to FIGS. 35-40, an expandable implant 1010 is shown according to an exemplary embodiment. Implant 1010 may include many of the features of the other inter/intra-body implants discussed elsewhere herein, particularly implant 610 shown and described with respect to FIGS. 10-19. All such combinations of features are to be understood to be within the scope of the present disclosure. Implant 1010 is generally similar to the other implants disclosed herein in structure and function except that implant 1010 utilizes a single control member/control channel configuration, and further utilizes a pivot pin about which an adjustable member pivots relative to a base member.

Figure 35:
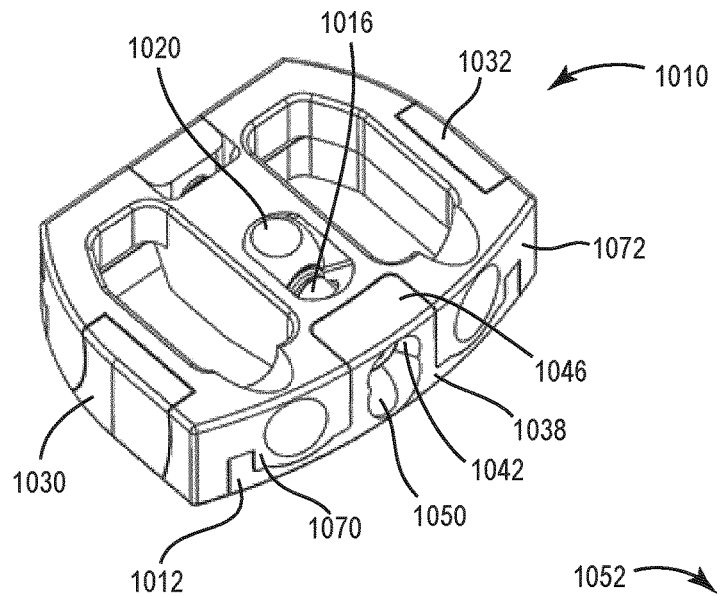
FIG. 35 is a perspective view of an expandable implant in a collapsed position according to another embodiment.

According to an exemplary embodiment, implant 1010 includes a base member 1012 and an adjustable member 1014 adjustably coupled to the base member 1012. A control shaft 1016 is received by the base member 1012 and is retained by a retention pin 1018 (e.g., a pivot pin or member, retaining pin) passing through a portion of the base member 1012 and/or the adjustable member 1014. A control member 1020 is received on the control shaft 1016 and is movable along the control shaft 1016 to adjust a position of the adjustable member 1014 between a collapsed position, as shown in FIG. 35, and an expanded position, as shown in FIG. 36.

In one embodiment, the base member 1012 includes a front or first end 1024, a rear or second end 1026, and a central cavity 1039 disposed between the first end 1024 and the second end 1026. The base member 1012 further includes a top surface 1046 and a bottom surface 1034 opposite the top surface 1046. The top and bottom surfaces 1046, 1034 may include ridges or projections formed by corresponding grooves, as similarly shown in FIGS. 10-19. The projections are configured to engage adjacent portions of bone. The base member 1012 further includes a bottom portion 1028. A first extension 1030 is positioned at a first side and extends upward from the bottom portion 1028, and a second extension 1032 is positioned at a second side and extends upward from the bottom portion 1028. Extensions 1030, 1032 include curved lateral surfaces 1033 (see FIG. 36) configured to engage corresponding curved surfaces 1035 (see FIG. 38) within recesses 1036 formed in adjustable member 1014 to maintain a desired pivotal alignment during movement of adjustable member 1014. A pin aperture 1068 extends through the bottom portion 1028 and is configured to receive the retention pin 1018 (e.g., in a press fit, sliding, or other manner). A front extension 1038 includes a bone screw bore 1050 configured to receive a bone screw 1022. The front extension 1038 includes a control bore 1042 configured to receive a head portion of the control shaft 1016.

Figure 36:
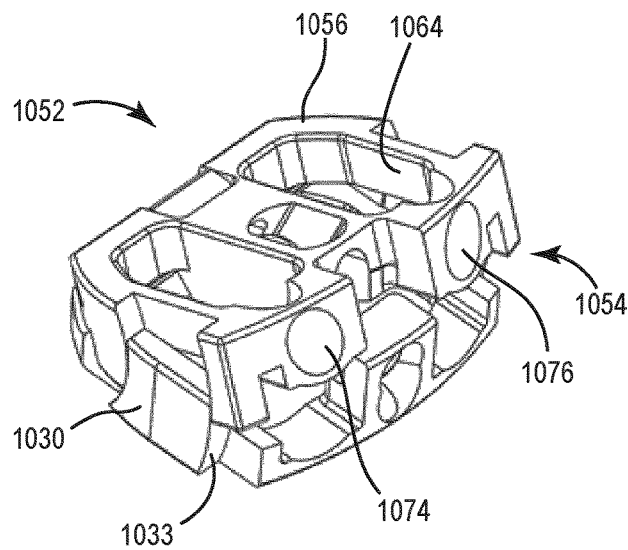
FIG. 36 is a perspective view of the implant of FIG. 35 in an expanded position according to one embodiment.

In one embodiment, the adjustable member 1014 includes a front or first end 1052, a rear or second end 1054, and cavities 1064 extending through the adjustable member 1014 and positioned between the first end 1052 and the second end 1054 (see FIG. 36). The adjustable member 1014 further includes a top surface 1056 that may include ridges or projections formed by corresponding grooves. The adjustable member 1014 further includes pin apertures 1068 (see FIG. 40) configured to receive the retention pin 1018 to enable movement (e.g., pivoting) of the adjustable member 1014 relative to the base member 1012. Further, the adjustable member includes a first bone screw support portion 1070 including a bone screw bore 1074 and a second bone screw support portion 1072 having a bone screw bore 1076. As shown in FIG. 35, the first and second bone screw support portions 1070, 1072 of the adjustable member 1014 and the front extension 1038 of the base member 1012 collectively form a front face of the implant 1010, such that the control shaft 1016 and the bone screws 1022 are accessible via the front face of the implant 1010 (e.g., when the implant 1010 is in a collapsed position). Furthermore, the first and second bone screw support portions 1070, 1072 and the front extension 1038 may be sized and spaced relative to each other so as to prevent undesired relative lateral movement between base member 1012 and adjustable member 1014.

In one embodiment, the adjustable member 1014 includes one or more control channels, such as control channel 1062. The control channel 1062 receives the control member 1020. In some embodiments, the control member 1020 is received in the control channel 1062 in a sliding manner such that the control member 1020 is able to translate within the control channel 1062. In further embodiments, the control channel 1062 has a shape such that the control channel 1062 surrounds the control member 1020 and at least partially corresponds in shape to the control member 1020.

The control shaft 1016 may include the features of control shaft 616 disclosed herein, and may include a head portion, a tool port disposed within the head portion, and a retention groove located at an end opposite the head portion. In some embodiments, the control shaft 1016 further includes a control thread 1082. Non-threaded portions may be located on one or both side of the control thread 1082. The control member 1020 may include the features of control member 620, and may include a body, one or more flat portions, and an internal thread. In some embodiments, the control member 1020 further includes a slotted portion configured to enable passing the control member 1020 over a portion (e.g., a non-threaded portion) of the control shaft 1016. The control member 1020 moves or translates both along the control shaft 1016 and within or on the control channel 1062.

Figure 37:
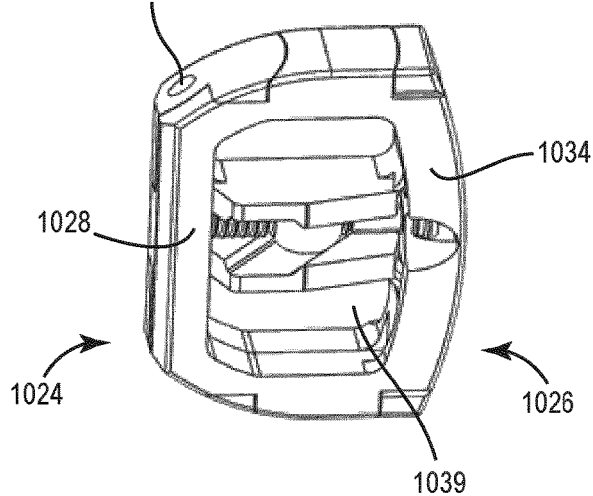
FIG. 37 is a bottom perspective view of the implant of FIG. 35 in an expanded position according to one embodiment.
Figure 38:
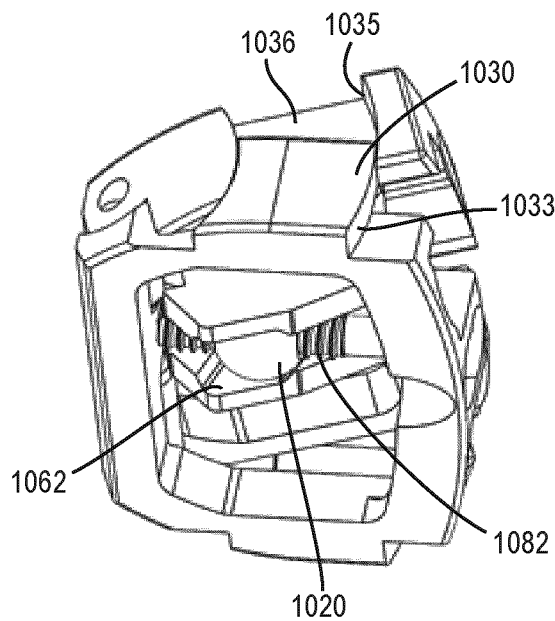
FIG. 38 is another bottom perspective view of the implant of FIG. 35 in an expanded position according to one embodiment.

Referring further to FIGS. 35-37, the control shaft 1016 is received by the base member 1012 such that the head portion of control shaft 1016 is positioned within the front extension 1038 of the base member 1012. In one embodiment, the control shaft 1016 is rotatable within the base member 1012, and a retention pin (e.g., retention pin 1018) extends into a retention groove of the control shaft 1016 to enable rotation of the control shaft 1016 while inhibiting translation of the control shaft 1016 relative to the base member 1012. The internal thread of the control member 1020 is received on the control thread 1082 of the control shaft 1016 such that as the control member 1020 moves along the control shaft 1016, the control member 1020 further moves within the control channel 1062, thereby causing relative movement (e.g., pivotal movement) of the adjustable member 1014 relative to the base member 1012 (e.g., about retention pin 1018). As the control member 1020 translates along the control shaft 1016, the adjustable member 1014 pivots about the retention pin 1018. The rate of movement of the control member 1020, and therefore the adjustable member 1014, can be adjusted by modifying the slope of the control channel 1062 relative to the control shaft 1016.

Figure 39:
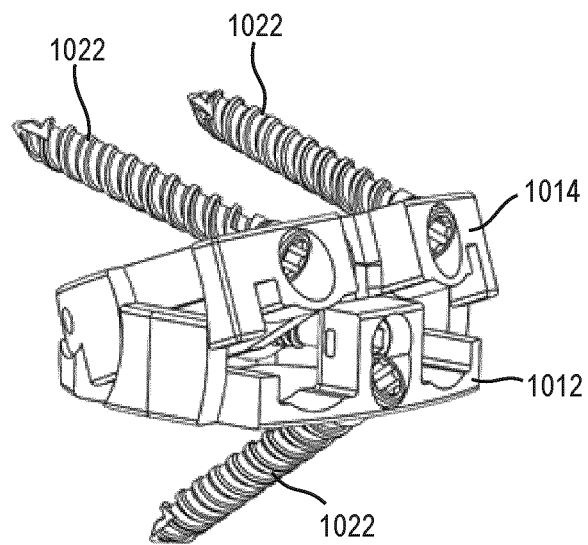
FIG. 39 is side perspective view of the implant of FIG. 35 in an expanded position with bone screws inserted according to one embodiment.
Figure 40:
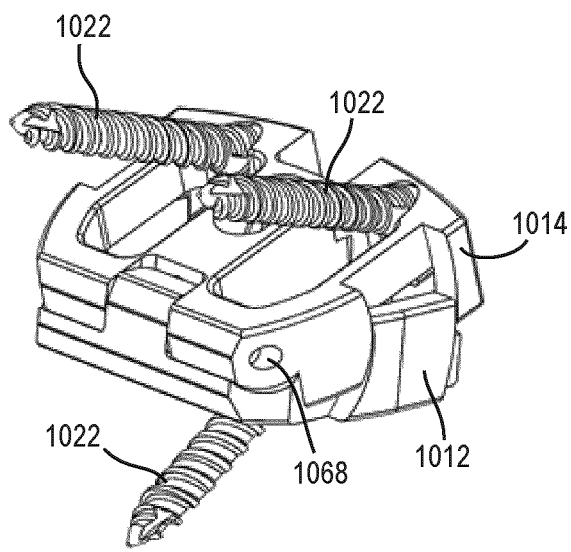
FIG. 40 is a rear perspective view of the implant of FIG. 35 in an expanded position with bone screws inserted according to another embodiment.

In use, implant 1010 is positioned within a desired space (e.g., between adjacent portions of bone) while in the first, collapsed position, as shown in FIG. 35. To position implant 1010, an appropriate tool may be used to engage tool recesses (similar to tool recesses 648) and manipulate implant 1010 into a desired position. Once in a desired position, a subsequent tool may be utilized to engage control shaft 1016 to pivot adjustable member 1014 to a desired degree of expansion. It should be noted that based on a particular application, the adjustable member 1014 may be utilized in a fully collapsed position, a fully expanded position, or any intermediate position therebetween. One or more bone screws 1022 may be screwed into adjacent portions of bone as shown in FIG. 39. Once implant 1010 is properly positioned and expanded to a desired height, bone graft material may be delivered by way of, for example, apertures 1064 or alternatively, by the space formed due to the expansion of adjustable member 1014. The various apertures in and through the base member 1012 and adjustable member 1014 may in some embodiments facilitate the growth of bone material in and around implant 1010 to further stabilize the device.

It should be noted that implant 1010 may share various features with the other implants described herein, and be made of the same, similar, or different materials. For example, various components of implant 1010 may be made of metal, plastic, composites, or other suitable bio-compatible materials. Further, implant 1010 may be usable in connection with the spine or other parts of the body.

Referring now to FIGS. 41-44, an expandable implant 1110 is shown according to an exemplary embodiment. Implant 1110 may include many of the features of the other inter/intra-body implants discussed elsewhere herein, particularly those features of implant 210 shown and described with respect to FIGS. 10-15. All such combinations of features are to be understood to be within the scope of the present disclosure. Implant 1110 is generally similar to implant 210 in structure and function except that implant 1110 includes extensions to receive bone screws.

Figure 41:
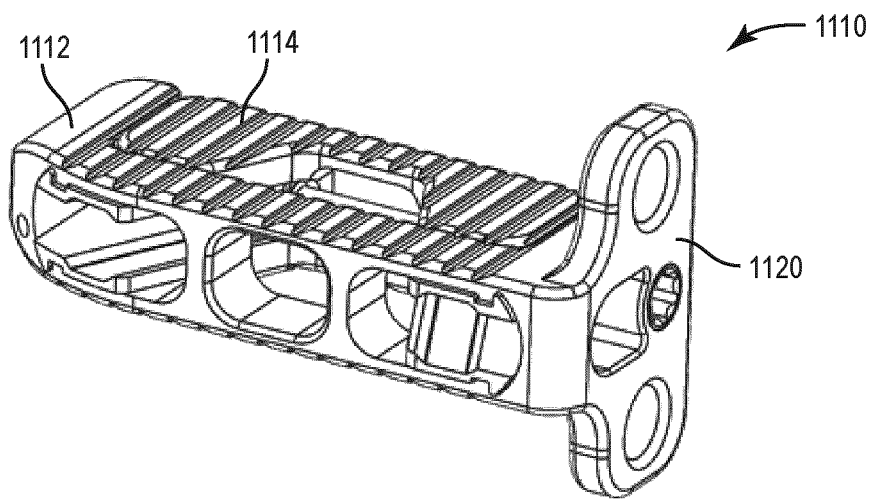
FIG. 41 is a perspective view of an expandable implant in a collapsed position according to one embodiment.
Figure 42:
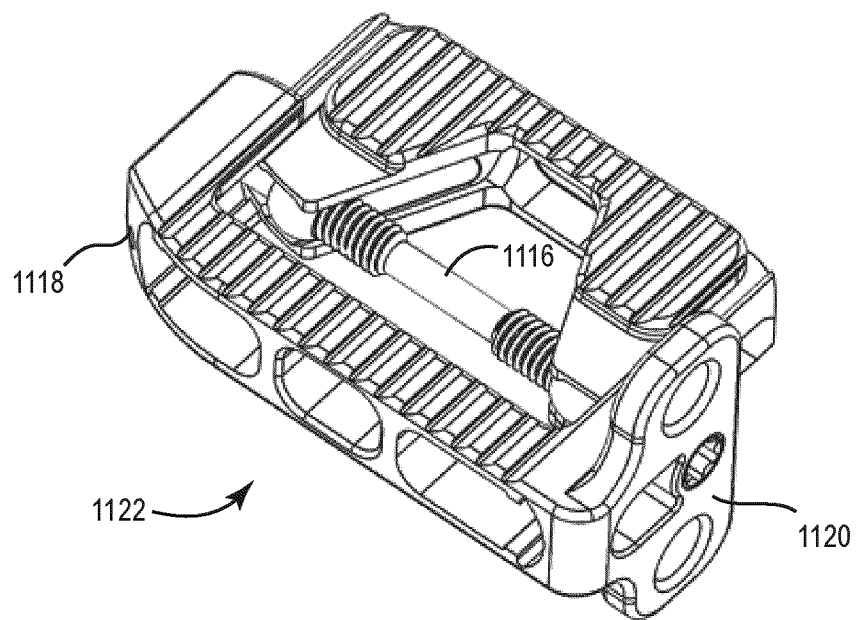
FIG. 42 is a perspective view of the implant of FIG. 41 in an expanded position according to one embodiment.

Implant 1110 includes a base member 1112 and an adjustable member 1114 adjustably coupled to the base member 1112. A control shaft 1116 is received by the base member 1112 and is retained by a retention pin 1118 passing through a portion of the base member 1112. A first control member and a second control member are received on the control shaft 1116 and are movable along the control shaft 1116 to adjust a position of the adjustable member 1114 between a collapsed position, as shown in FIG. 41, and an expanded position, as shown in FIG. 42.

In addition to those features discussed with respect to implant 210, any of which may be included as part of implant 1110, implant 1110 further includes a flange portion or extension 1120. Extension 1120 extends from a main body portion 1122 of base member 1112 and includes an upper extension 1124 and a lower extension 1126. Upper extension 1124 includes a first bone screw bore 1128, and lower extension 1126 includes a second bone screw bore 1130. Extension 1120 further includes an aperture 1133 and a control bore 1134.

Implant 1110 is adjustable in a similar manner to implant 10. However, while adjustment of implant 10 causes a change in height of the implant 10, adjustment of the implant 1110 causes a change in width of the implant 1110 (while maintaining a constant height). As such, while during adjustment of the implant 10, the top surface of the adjustable member 14 may be offset from the top surface of the base member 12, during adjustment of implant 1110, the top surface of the adjustable member 1114 stays generally aligned with the top surface of the base member 1112. The implant 1110 may be used to provide, for example, a more stable implant by increasing the footprint of the implant and engagement areas with adjacent portions of bone. The implantation of the implant 1110 is otherwise similar to that of the implant 10 and the other implants noted herein.

In some embodiments, extensions 1124, 1126 extend in generally opposite directions relative to main portion 1122 of the base member 1112 (e.g., in a perpendicular fashion, in an angled fashion, etc.). As such, extensions 1124, 1126 may act as to limit the insertion of implant 1110 into a vertebral or other space by way of extensions 1124, 1126 interfacing or interfering with adjacent portions of bone. Furthermore, extensions 1124, 1126 and bone screw bores 1128, 1130 may be configured such that bone screws 1132 extend in a generally parallel manner to the longitudinal axis of implant 1110 (see FIG. 44). This configuration may facilitate fastening bone screws 1132 into adjacent portions of bone due to the alignment of the screws with an incision and/or the implant.

It should be noted that the implant 1110 may share various features with the other implants described herein, and be made of the same, similar, or different materials. For example, various components of implant 1110 may be made of metal, plastic, composites, or other suitable bio-compatible materials. Further, implant 1110 may be usable in connection with the spine or other parts of the body.

Referring now to FIGS. 45-53, an expandable implant 1210 is shown according to an exemplary embodiment. The implant 1210 is usable, for example, between and/or within vertebral bodies of the spine, and may include any or all of the features of the other inter/intra-body implants discussed elsewhere herein. All such combinations of features are to be understood to be within the scope of the present disclosure. It should be understood that the implant 1210 may in some embodiments be usable in other portions of the body in addition to the spine, and all such applications are to be understood to be within the scope of the present disclosure. The implant 1210 is in many ways similar to implant 510, and may include any of the features of implant 510 or the other implants disclosed herein.

Figure 45:
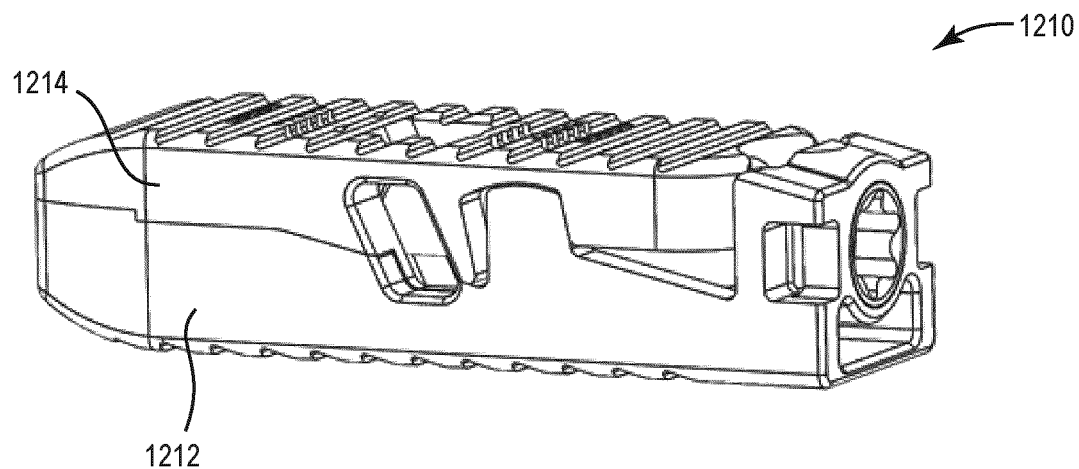
FIG. 45 is a side perspective view of an expandable implant in a collapsed position according to one embodiment.
Figure 46:
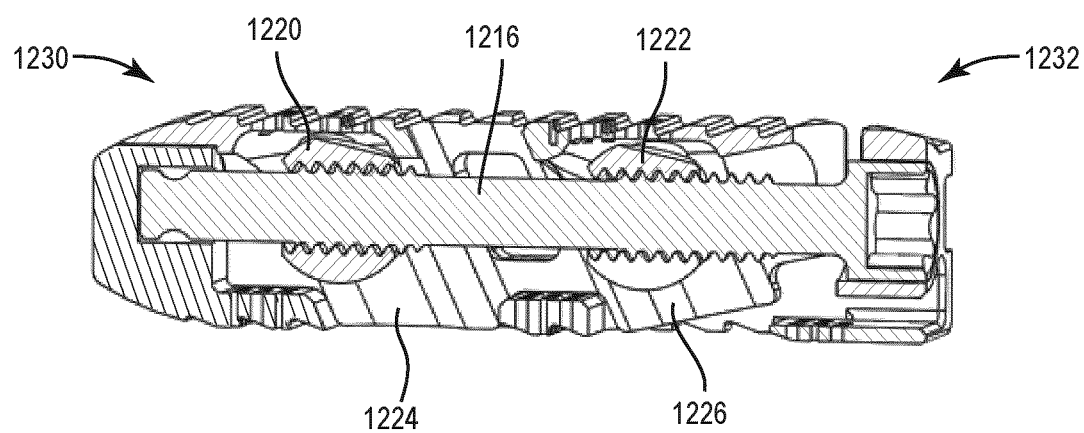
FIG. 46 is a cross section view of the implant of FIG. 45 is a collapsed position according to one embodiment.
Figure 49:
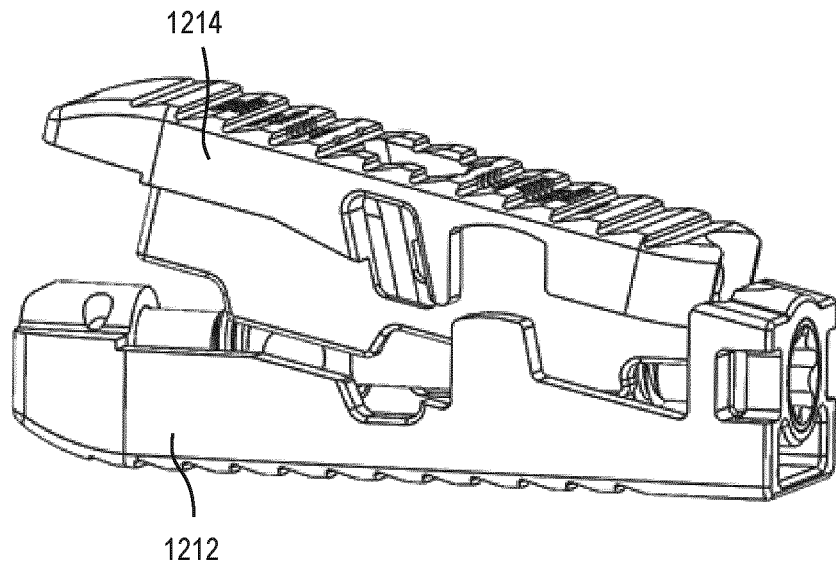
FIG. 49 is side perspective view of the implant of FIG. 45 in an expanded position according to one embodiment.
Figure 50:
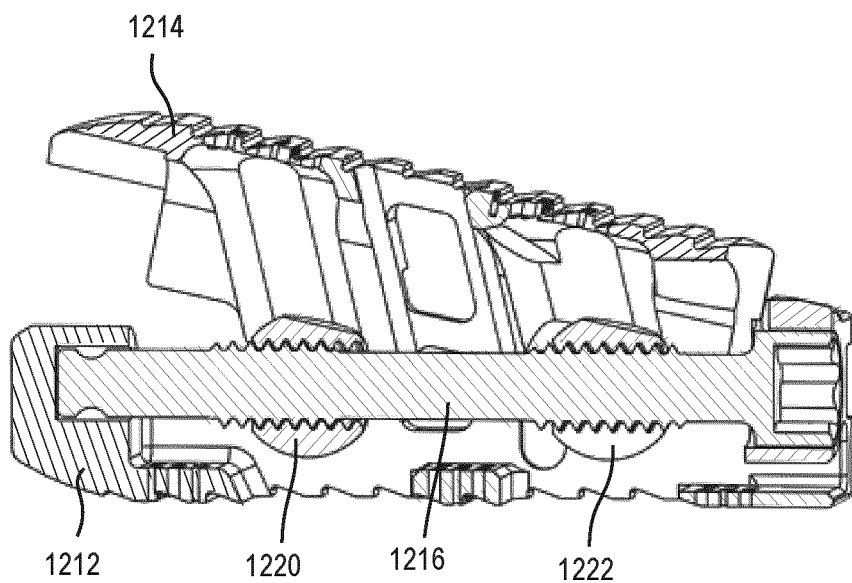
FIG. 50 is a cross section view of the implant of FIG. 45 in an expanded position according to one embodiment.
Figure 51:
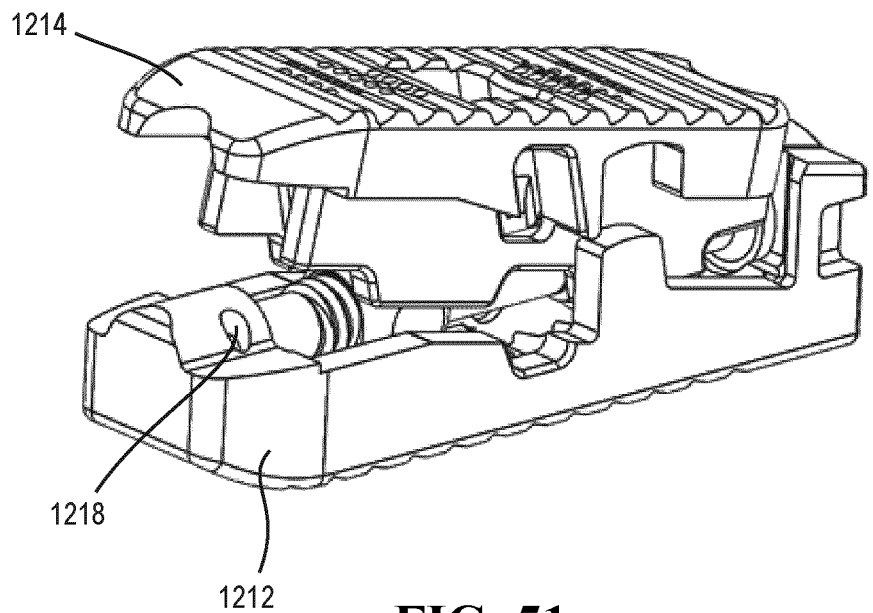
FIG. 51 is another perspective view of the implant of FIG. 45 in an expanded position according to one embodiment.

According to an exemplary embodiment, the implant 1210 includes a base member 1212 and an adjustable member 1214 adjustably coupled to the base member 1212. A control shaft 1216 is received by the base member 1212 and is retained by a retention pin 1218 passing through a portion of the base member 1212. A first control member 1220 and a second control member 1222 are received on the control shaft 1216 and are movable along the control shaft 1216 to adjust a position of the adjustable member 1214 between a collapsed position, as shown in FIGS. 45-46, and an expanded position, as shown in FIGS. 49-50.

In one embodiment, the adjustable member 1214 includes a front or first end 1230, and a rear or second end 1232. The adjustable member 1214 further includes one or more control channels, such as a first control channel 1224 and a second control channel 1226. The first control channel 1224 receives the first control member 1220, and the second control channel 1226 receives the second control member 1222. In some embodiments, the control members 1220, 1222 are received in the control channels 1224, 1226 in a sliding manner such that the control members 1220, 1222 are able to translate within the control channels 1224, 1226. In further embodiments, each control channel has a shape such that the control channel surrounds the control member and at least partially corresponds in shape to the control member.

As shown in FIGS. 46-50, as the control members 1220, 1222 move along the control shaft 1216, the control members 1220, 1222 further move within the control channels 1224, 1226, thereby causing relative movement of the adjustable member 1214 and the base member 1212. As the control members 1220, 1222 translate along the control shaft 1216, the adjustable member 1214 is moved based on the shape of the first and second control channels 1224, 1226. The rate of movement of the control members 1220, 1222, and therefore the adjustable member 1214, can be adjusted by modifying the slope of the control channels 1224, 1226 relative to the control shaft 1216.

Figure 52:
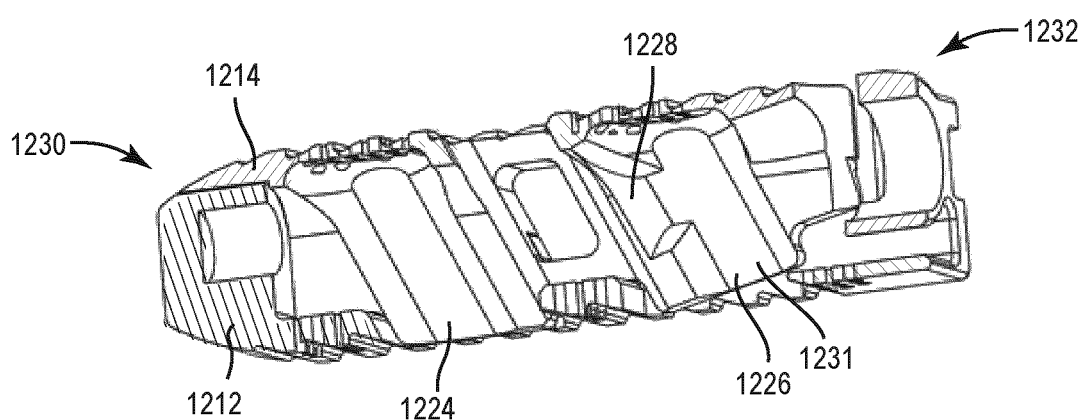
FIG. 52 is a partial cutaway view of the implant of FIG. 45 according to one embodiment.

For example, as shown in FIG. 52, the first control channel 1224 extends at an angle relative to the control shaft 1216, and has a substantially linear form and constant slope, thereby providing a generally constant corresponding rate of movement of the first end 1230 of the adjustable member 1214. The second control channel 1226 includes a first channel portion 1228 and a second channel portion 1231 which extend at different angles relative to the control shaft 1216. As shown in FIG. 52, the first channel portion 1228 is generally parallel to the control shaft 1216, and the second channel portion 1231 extends at an angle similar to that of first control channel 1224. As such, the second control channel 1226 provides a non-constant rate of movement of second end 1232 of the adjustable member 1214.

Figure 47:
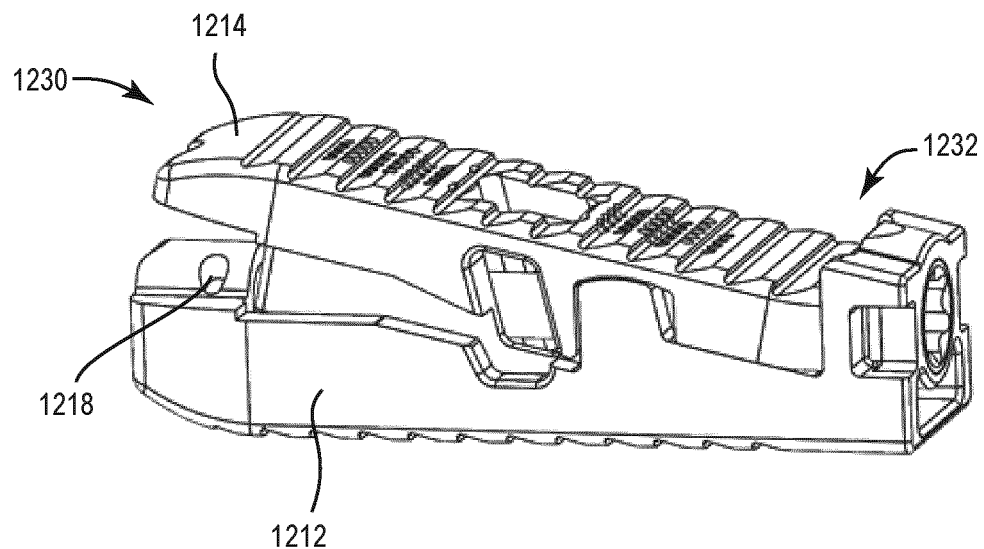
FIG. 47 is a side perspective view of the implant of FIG. 45 in an intermediate position according to one embodiment.
Figure 48:
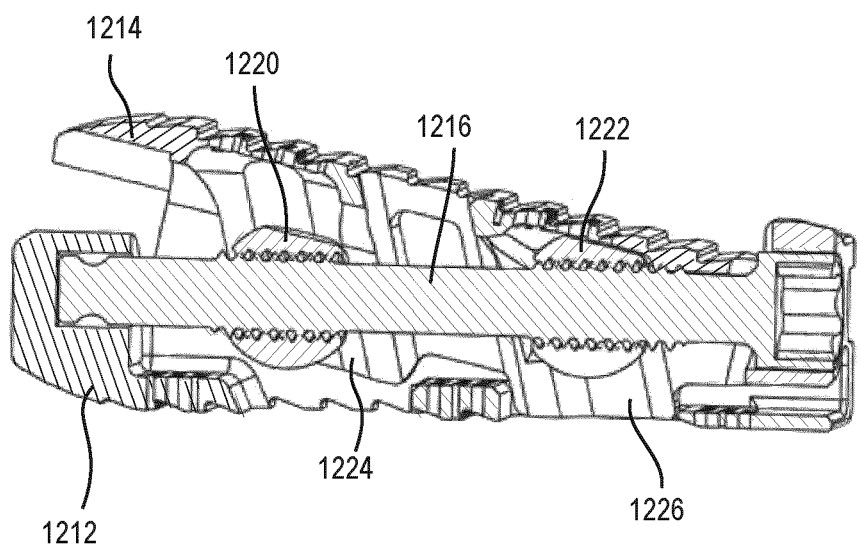
FIG. 48 is a cross section view of the implant of FIG. 45 in an intermediate position according to one embodiment.

FIGS. 45-50 illustrate the corresponding movement of the adjustable member 1214 resulting from the differing configurations of the first control channel 1224 and the second control channel 1226. In FIGS. 45 and 46, the implant 1210 is in a collapsed position, such that the control members 1220, 1222 reside in the upper positions within the first and second control channels 1224, 1226. FIGS. 47 and 48 illustrate implant 1210 in an intermediate expanded position, where second control member 1222 is positioned generally at the intersection of the first channel portion 1228 and the second channel portion 1231. Due to the orientation of the first channel portion 1228, the second end 1232 of adjustable member 1214 has moved downward relative to the height as that shown in FIGS. 45 and 46, while due to the configuration of first control channel 1224, the first end 1230 of the adjustable member 1214 has moved upward relative to the base member 1212. FIGS. 49 and 50 show the implant 1210 in a fully expanded position, where control members 1220, 1222 reside in the lower/outer—most positions within the first and second control channels 1224, 1226. Due to the angled configurations of both the first control channel 1224 and the second channel portion 1231 of the second control channel 1226, both the first end 1230 and the second end 1232 move relative to the base member 1212.

Figure 53:
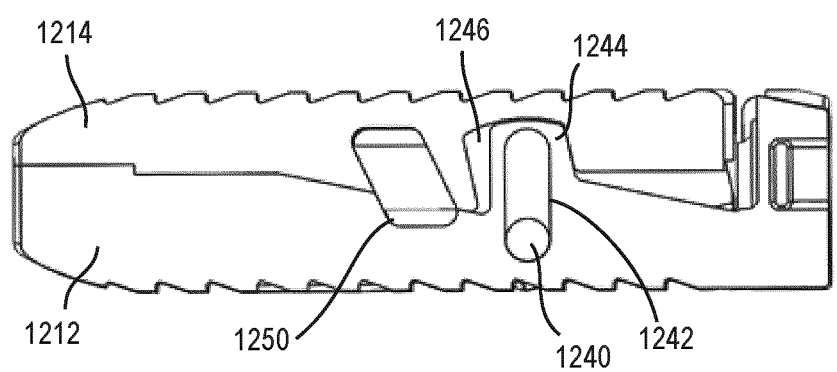
FIG. 53 is a side view of the implant of FIG. 45 according to another embodiment.

Referring to FIG. 53, in some embodiments, implant 1210 includes features intended to facilitate non-linear movement of adjustment member 1214 relative to base member 1212. For example, in one embodiment, a pin 1240 (e.g., a projection, etc.) provided on adjustment member 1214 resides within a slot 1242 (e.g., a recess, etc.) provided on base member 1212. The pin 1240 may rotate and/or translate within the slot 1242. Pin 1240 and a slot 1242 limit the range of relative motion between adjustable member 1214 and base member 1212. Further, base member 1212 may include an alignment guide 1244 (e.g., an upstanding wall portion, etc.) received within an alignment recess 1246 in adjustable member 1214. Alignment guide 1244 and alignment recess 1246 are configured such that in a first, collapsed position, a first side of alignment guide 1244 engages a first side of recess 1246 (see FIG. 45), and in an intermediate position a second side of alignment guide 1244 engages a second side of recess 1246 (see FIG. 47). In the fully expanded position, the alignment guide 1244 and recess 1246 may disengage due to the separation of the adjustable member 1214 and the base member 1212.

In one embodiment, implant 1210 includes one or more apertures intended to provide fluid communication (e.g., for the delivery of bone growth material, etc.) between an exterior and an interior of implant 1210. For example, in one embodiment, implant 1210 includes one or more apertures 1250 extending from an exterior of implant 1210 to an interior. Aperture 1250 may be formed in base member 1212, adjustable member 1214, or as shown in FIG. 53, collectively formed by members 1212, 1214.

Providing an implant with adjustment features such as those provided by implant 1210 may facilitate accommodating a desired spinal curvature or other anatomical features where non-parallel supporting surfaces are suitable for a particular application. It should be noted that the control channels and/or control rails herein may take any desired configuration to provide desired expansion and contraction characteristics for a particular implant.

Referring now to FIGS. 54-60, an expandable implant 1310 is shown according to an exemplary embodiment. The implant 1310 is usable, for example, between and/or within vertebral bodies of the spine, and may include any or all of the features of the other inter/intra-body implants discussed elsewhere herein. All such combinations of features are to be understood to be within the scope of the present disclosure. It should be understood that the implant 1310 may in some embodiments be usable in other portions of the body in addition to the spine, and all such applications are to be understood to be within the scope of the present disclosure. The implant 1310 is in many ways similar to implant 410, and may include any of the features of implant 410 or the other implants disclosed herein.

Figure 54:
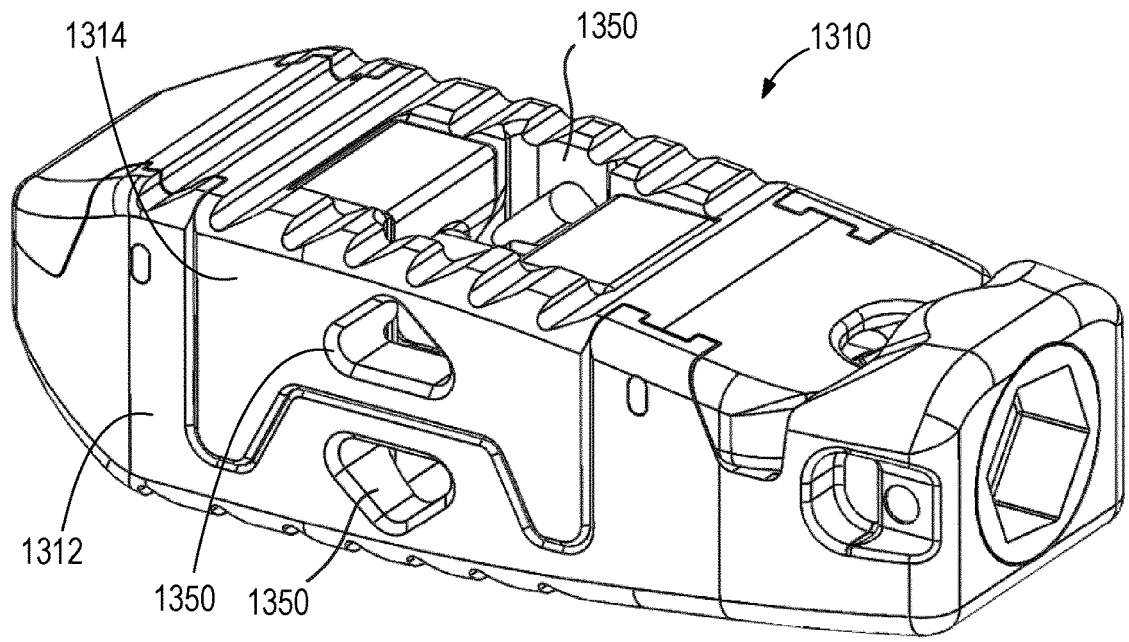
FIG. 54 is a side perspective view of an expandable implant in a collapsed position according to one embodiment.
Figure 55:
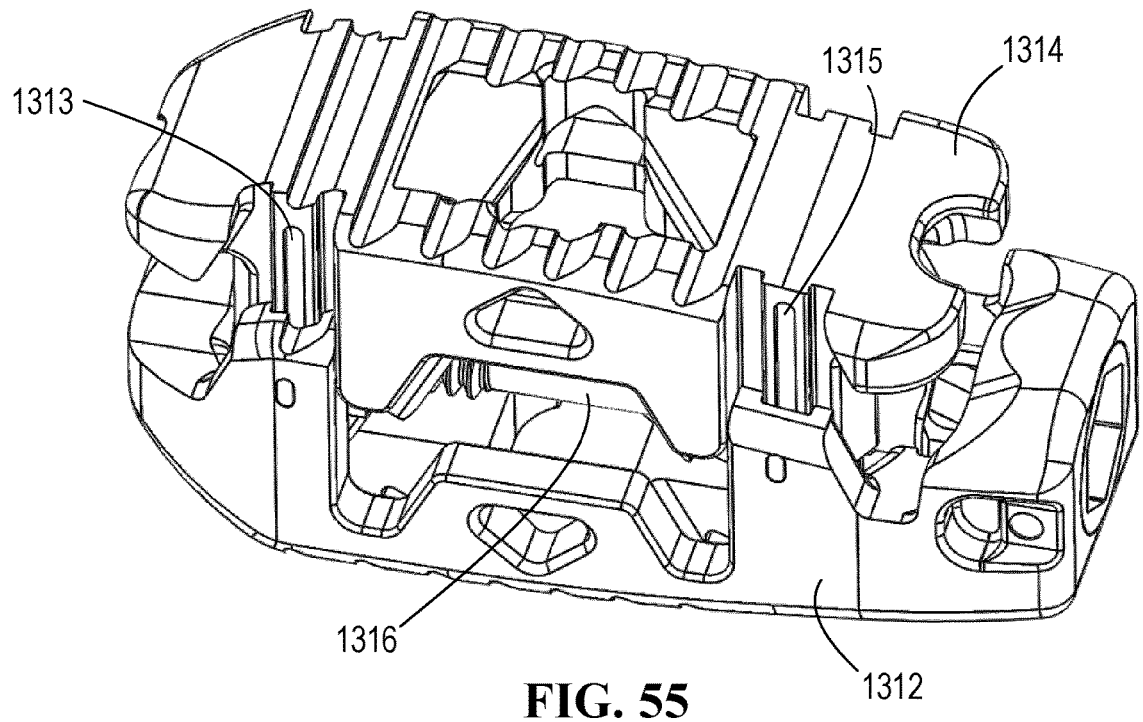
FIG. 55 is a side perspective view of the implant of FIG. 54 in an expanded position according to one embodiment.

According to an exemplary embodiment, the implant 1310 includes a base member 1312 and an adjustable member 1314 adjustably coupled to the base member 1312. A control shaft 1316 is received by the base member 1312 and is retained by a retention pin 1318 passing through a portion of the base member 1312 to be received by a groove 1321 on the control shaft 1316. The groove 1321 is configured to allow rotational motion of the control shaft 1316 while preventing lateral (e.g., side to side, in and out) translation of the control shaft 1316. A first control member 1320 and a second control member 1322 are received on the control shaft 1316 and are movable along the control shaft 1316 to adjust a position of the adjustable member 1314 between a collapsed position, as shown in FIG. 54, and an expanded position, as shown in FIG. 55.

Figure 56:
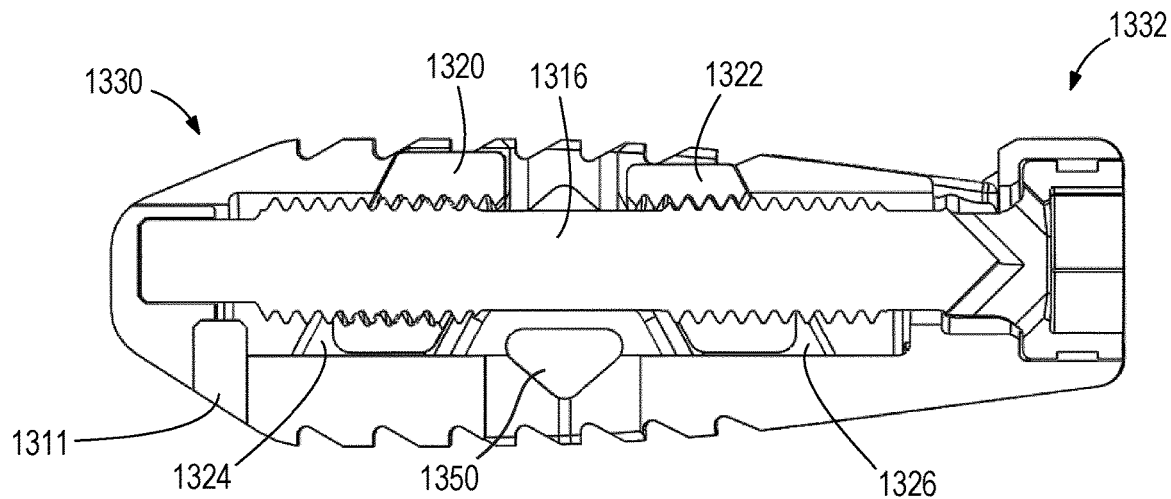
FIG. 56 is a cross section view of the implant of FIG. 54 in a collapsed position according to one embodiment.
Figure 59:
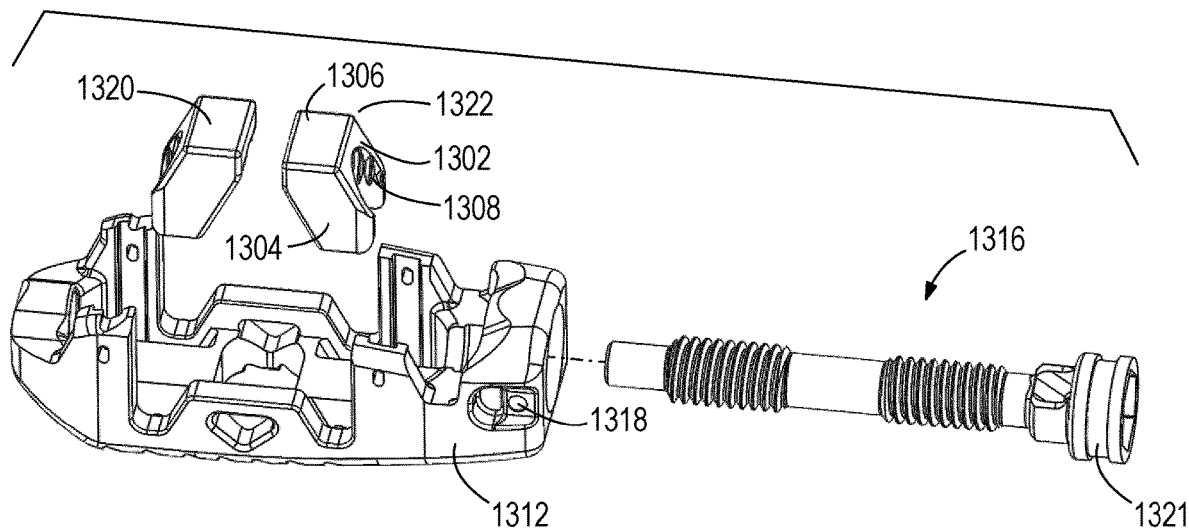
FIG. 59 is a partial exploded view of the implant of FIG. 54 according to one embodiment.
Figure 60:
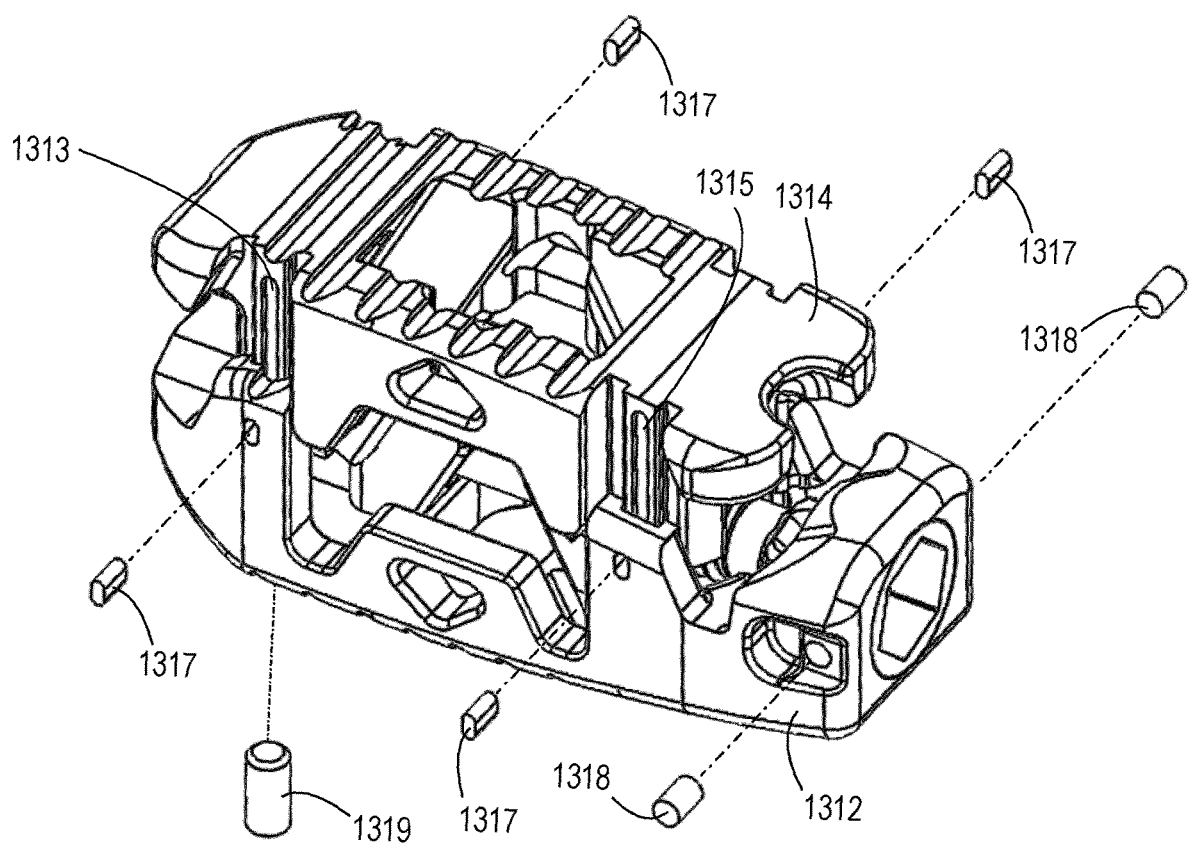
FIG. 60 is another partial exploded view of the implant of FIG. 54 according to one embodiment.

In one embodiment, the adjustable member 1314 includes a front or first end 1330, and a rear or second end 1332. The adjustable member 1314 further includes one or more control channels, such as first control channel 1324 and a second control channel 1326. The first control channel 1324 receives the first control member 1320, and the second control channel 1326 receives the second control member 1322. One or more retention pins 1317 may be received by the base member 1312 and prevent the adjustable member 1314 from becoming uncoupled from the base member 1312, as shown in FIG. 60. For example, the retention pins 1317 may contact channels 1313 and 1315 of the adjustable member 1314 to prevent the adjustable member 1314 from extending further. The channels 1313 and 1315 may align the adjustable member 1314 to the base member 1312 and further prevent the adjustable member 1314 from uncoupling from the base member 1312. Further, the channels 1313 and 1315 may define an amount of expansion allowable for the adjustable member 1314. Retention pin 1319 may be received by slot 1311 of the base member 1312 and limit translation of the first control member 1320, as shown in FIG. 56. Further, one or more retention pins 1318 may be received by the base member 1312 and contact the groove 1321 to secure the control shaft 1316, as shown in FIG. 59.

In some embodiments, the control members 1320, 1322 are received in the first control channels 1324, 1326 in a sliding manner such that the control members 1320, 1322 are able to translate within the control channels 1324, 1326. In further embodiments, each control channel has a shape such that the control channel surrounds the control member and at least partially corresponds in shape to the control member. In one embodiment, the control members 1320, 1322 are rhomboid prisms configured to engage the first and second control channels 1324, 1326. The control members 1320, 1322 include one or more flat portions 1302-1306, and an internal thread 1308. Relative to other shapes, rhomboidal control members may provide greater surface contact for the first and second control channels 1324, 1326 to increase the area over which an expanding force acts, thereby reducing part fatigue and increasing part lifetime.

Figure 57:
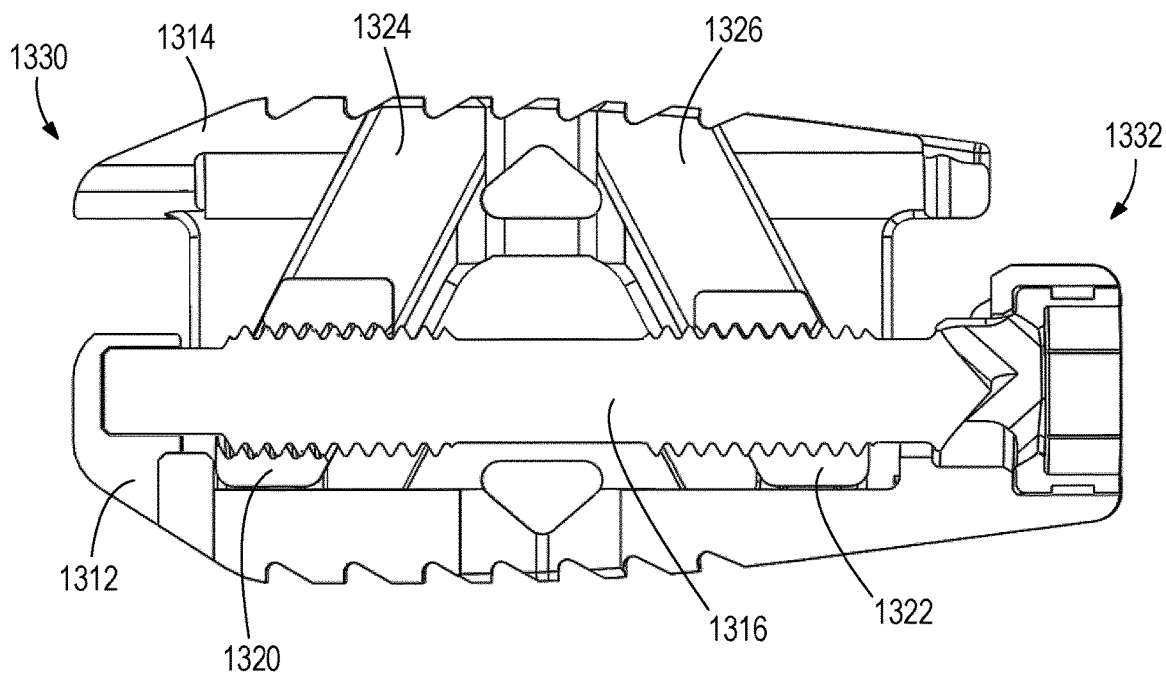
FIG. 57 is a cross section view of the implant of FIG. 54 in an expanded position according to one embodiment.
Figure 58:
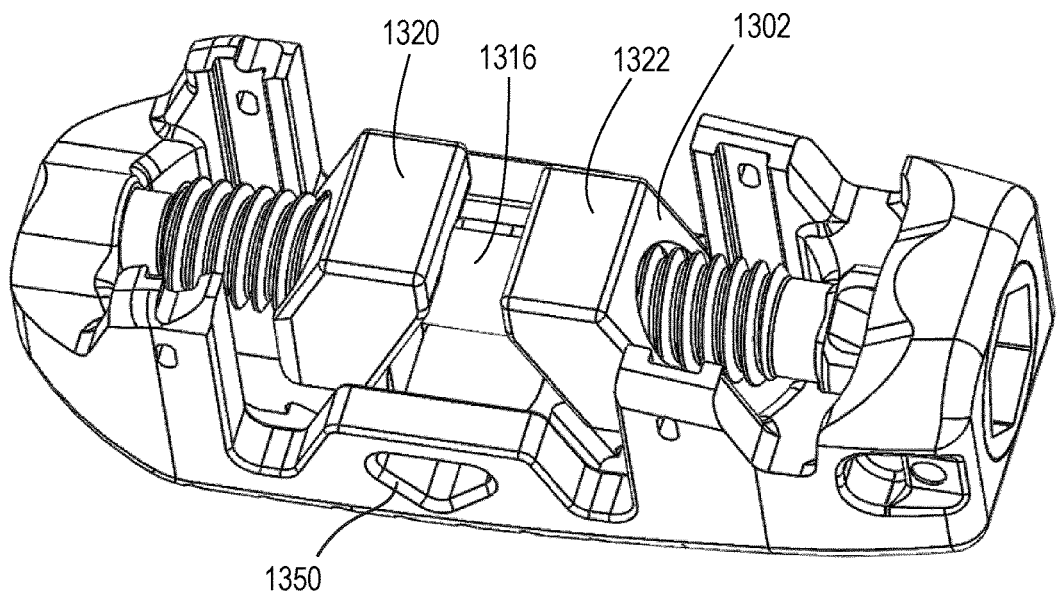
FIG. 58 is a partial cutaway view of the implant of FIG. 54 according to one embodiment.

As shown in FIGS. 56 and 57, as the control members 1320, 1322 move along the control shaft 1316, the control members 1320, 1322 further move within the control channels 1324, 1326, thereby causing relative movement of the adjustable member 1314 and the base member 1312. As the control members 1320, 1322 translate along the control shaft 1316, the adjustable member 1314 is moved based on the shape of the first and second control channels 1324, 1326. The rate of movement of the control members 1320, 1322, and therefore the adjustable member 1314, can be adjusted by modifying the slope of the control channels 1324, 1326 relative to the control shaft 1316 and/or by modifying the thread (e.g., lead, pitch, etc.) of the control shaft 1316 to cause greater or lesser translation of the control members 1320, 1322 for the same amount of rotation of the control shaft 1316.

In one embodiment, implant 1310 includes one or more apertures intended to provide fluid communication (e.g., for the delivery of bone growth material, etc.) between an exterior and an interior of implant 1310. For example, in one embodiment, implant 1310 includes one or more apertures 1350 extending from an exterior of implant 1310 to an interior. Aperture 1350 may be formed in base member 1312 or adjustable member 1314 and may extend through a top, bottom, side, or other surface.

Figure 61:
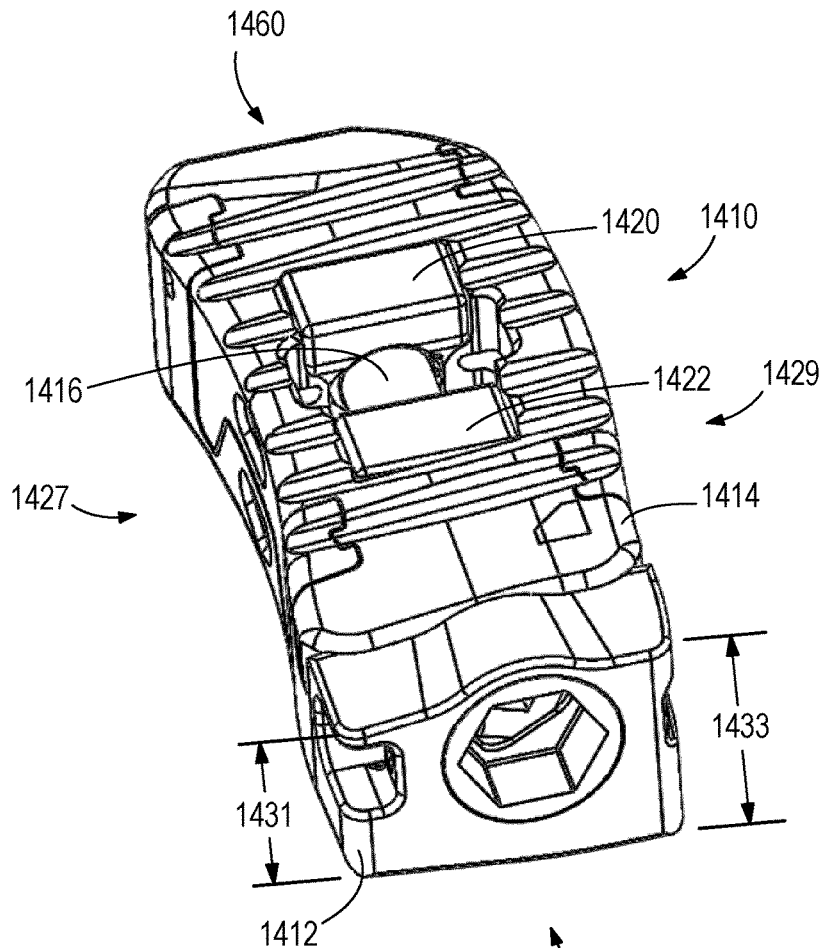
FIG. 61 is a front perspective view of an expandable implant in a collapsed position according to one embodiment.
Figure 62:
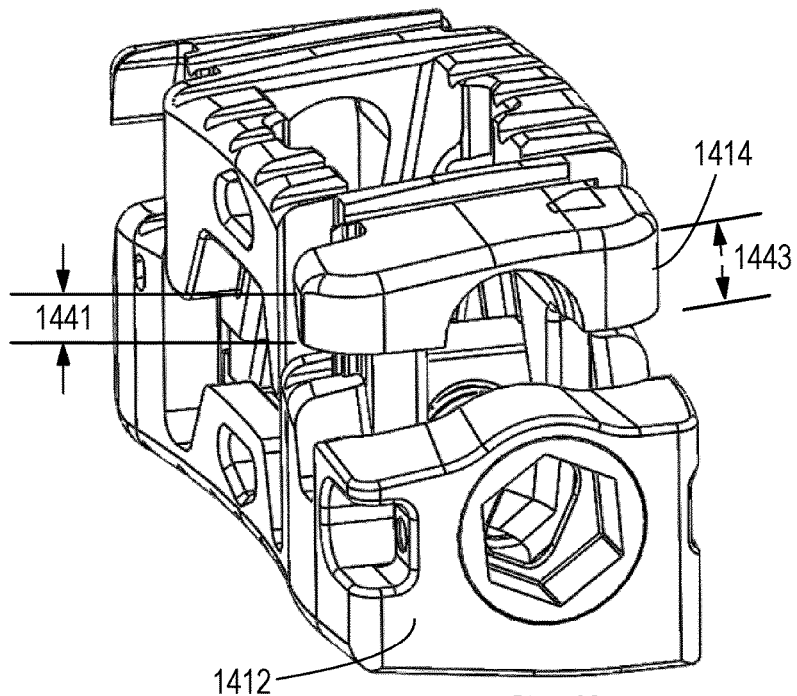
FIG. 62 is a front perspective view of the expandable implant of FIG. 61 in an expanded position according to one embodiment.

Referring now to FIGS. 61 and 62, an expandable implant 1410 is shown according to an exemplary embodiment. The implant 1410 is usable, for example, between and/or within vertebral bodies of the spine, and may include any or all of the features of the other inter/intra-body implants discussed elsewhere herein. All such combinations of features are to be understood to be within the scope of the present disclosure. It should be understood that the implant 1410 may in some embodiments be usable in other portions of the body in addition to the spine, and all such applications are to be understood to be within the scope of the present disclosure. The implant 1410 is in many ways similar to implant 1310, and may include any of the features of implant 1310 or the other implants disclosed herein.

According to an exemplary embodiment, the implant 1410 includes a base member 1412 and an adjustable member 1414 adjustably coupled to the base member 1412. A control shaft 1416 is received by the base member 1412. A first control member 1420 and a second control member 1422 are received on the control shaft 1416 and are movable along the control shaft 1416 to adjust a position of the adjustable member 1414 between a collapsed position, as shown in FIG. 61, and an expanded position, as shown in FIG. 62. The implant 1410 includes a front or first end 1460, and a back or second end 1462. According to an exemplary embodiment, the implant 1410 is substantially curved such that the sides 1427 and 1429 are curved between a first end 1460 and a second end 1462. In some embodiments, a curvature of the implant 1410 is "banana" shaped.

According to an exemplary embodiment, the implant 1410 includes a front or first side 1427, and a rear or second side 1429. The first side 1427 of the base member 1412 has a first height 1431 and the second side 1429 of the base member 1412 has a second height 1433. In some embodiments, the first height 1431 and the second height 1433 are different. For example, the second height 1433 may be greater than the first height 1431 such that the implant 1410 is substantially wedge shaped. Additionally or alternatively, the first side 1427 of the adjustable member 1414 has a first height 1441 and the second side 1429 of the adjustable member 1414 has a second height 1443.

Providing an implant with forms such as those provided by implant 1410 may facilitate accommodating a desired spinal curvature or other anatomical features where non-parallel supporting surfaces are suitable for a particular application. It should be noted that the sides (e.g., first and second side 1427 and 1429) of base member 1412 and/or adjustable member 1414 described herein may take any desired height to provide desired supporting slope for a particular implant. Furthermore, providing an implant with a curvature such as that of the implant 1410 may facilitate accommodating different shapes of bone members or other anatomical features that are substantially non-straight in form.

Referring now to FIGS. 63-75, various implants are shown that may provide elastic or compressibility features. For example, referring to FIGS. 63-66, an implant 1610 is shown. Implant 1610 may be substantially identical to implant 1310 disclosed herein except for the structure of the control members, in that implant 1610 provides control members having a higher modulus of elasticity relative to other portions of implant 1610 to more closely replicate the structure and function of certain parts of the human anatomy, such as portions of the spine. Further, while the various implants disclosed herein generally include a rotatable control shaft, other types of manipulation or actuation of the control shaft may be used to adjust the height of the implant, including longitudinal translation, lateral translation, irregular manipulations, combinations thereof, etc. All such types of manipulation or actuation of a control shaft are to be understood to be within the scope of the present disclosure.

Figure 63:
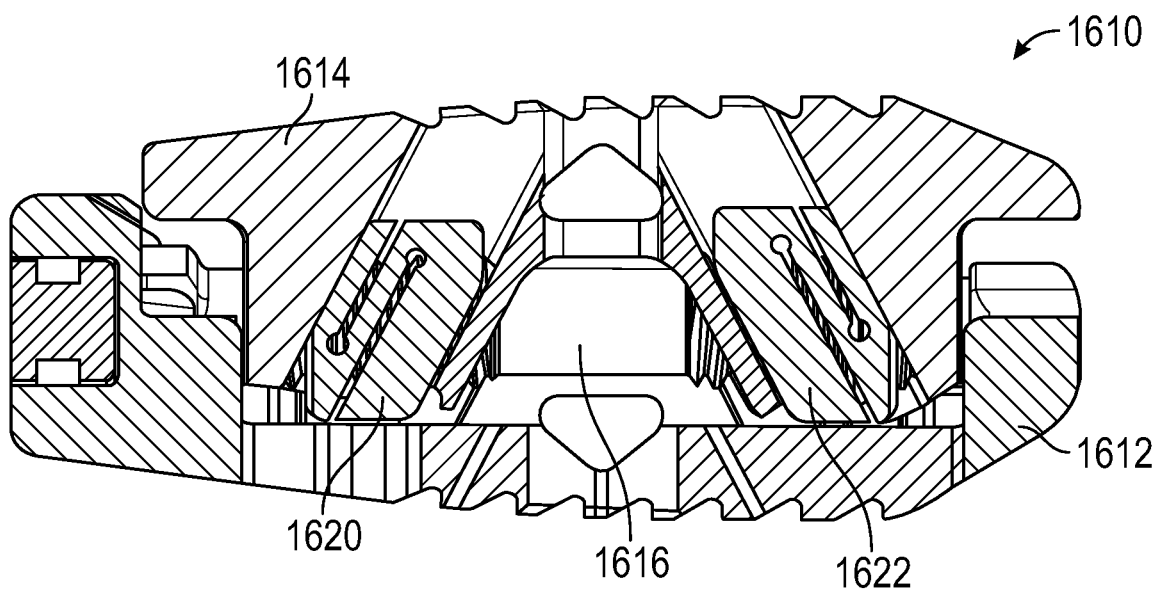
FIG. 63 is a cross-section view of an expandable implant according to another embodiment.
Figure 64:
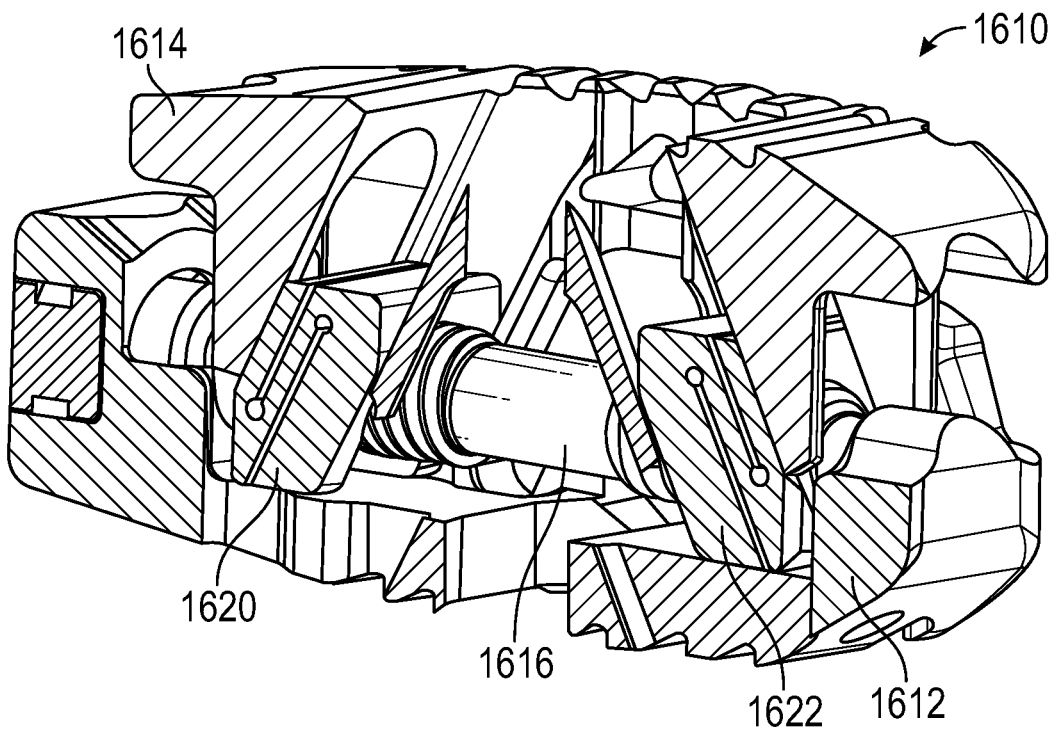
FIG. 64 is another cross-section view of the expandable implant of FIG. 63.

For example, referring to FIGS. 63 and 64, implant 1610 includes a base member 1612 and an adjustable member 1614. A control shaft 1616 and control members 1620, 1622 enable adjustment of adjustable member 1614 relative to base member 1612, as discussed in greater detail with respect to implant 1310 and the other embodiments disclosed herein. It should be noted that FIG. 64 is a cross-sectional view taken along a plane slightly offset from the axis of control member 1616 in order to provide more clarity with respect to the structure of control members 1620, 1622.

Figure 65:
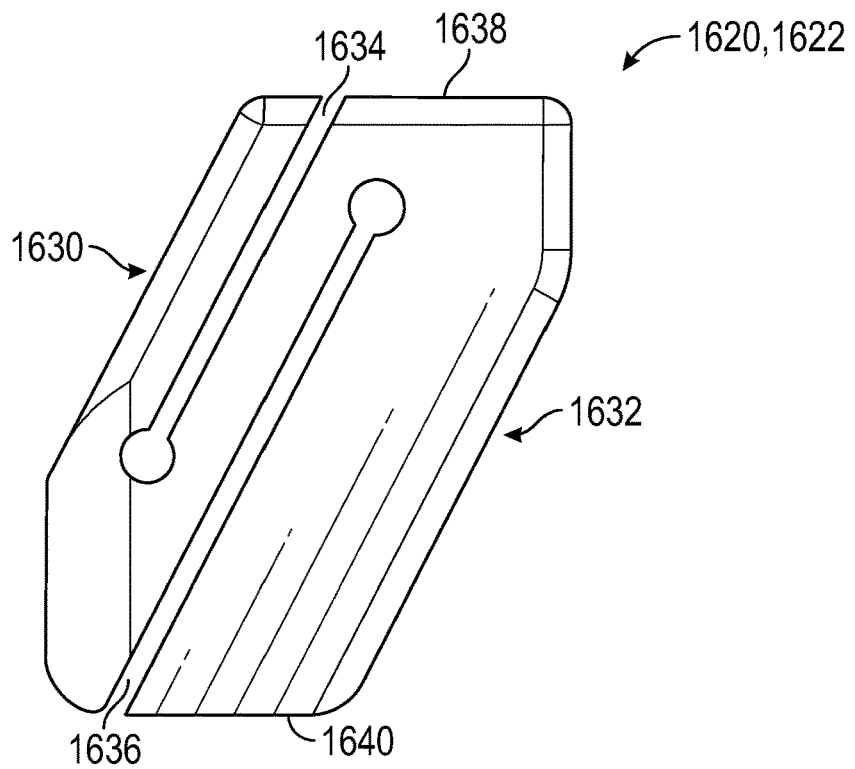
FIG. 65 is a side view of a control member of the expandable implant of FIG. 63.
Figure 66:
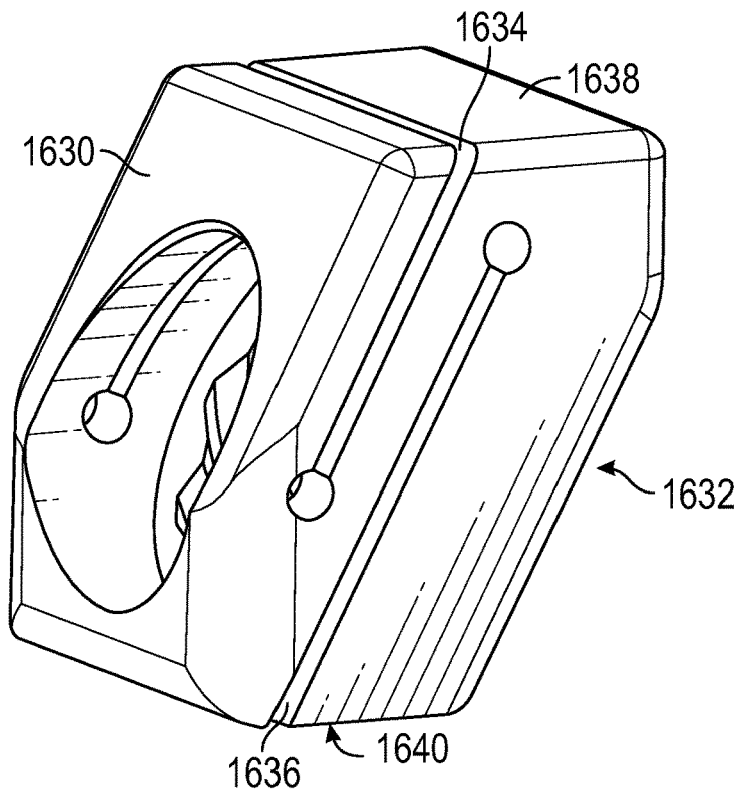
FIG. 66 is a perspective view of the control member of FIG. 65.
Figure 67:
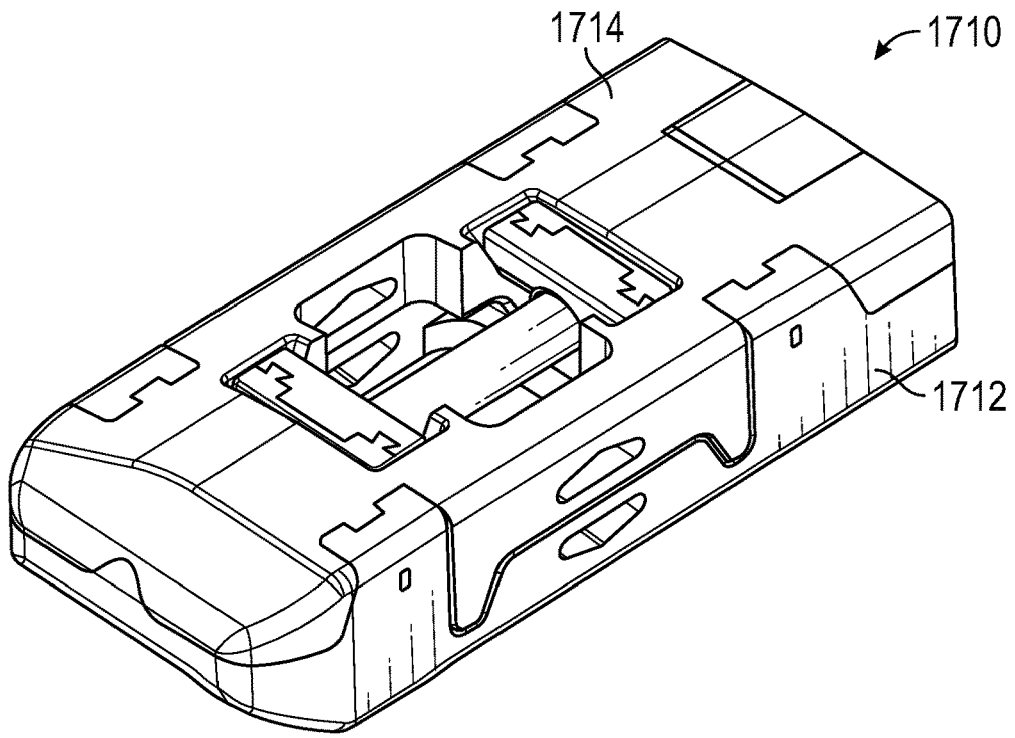
FIG. 67 is a perspective view of an expandable implant according to another embodiment.
Figure 68:
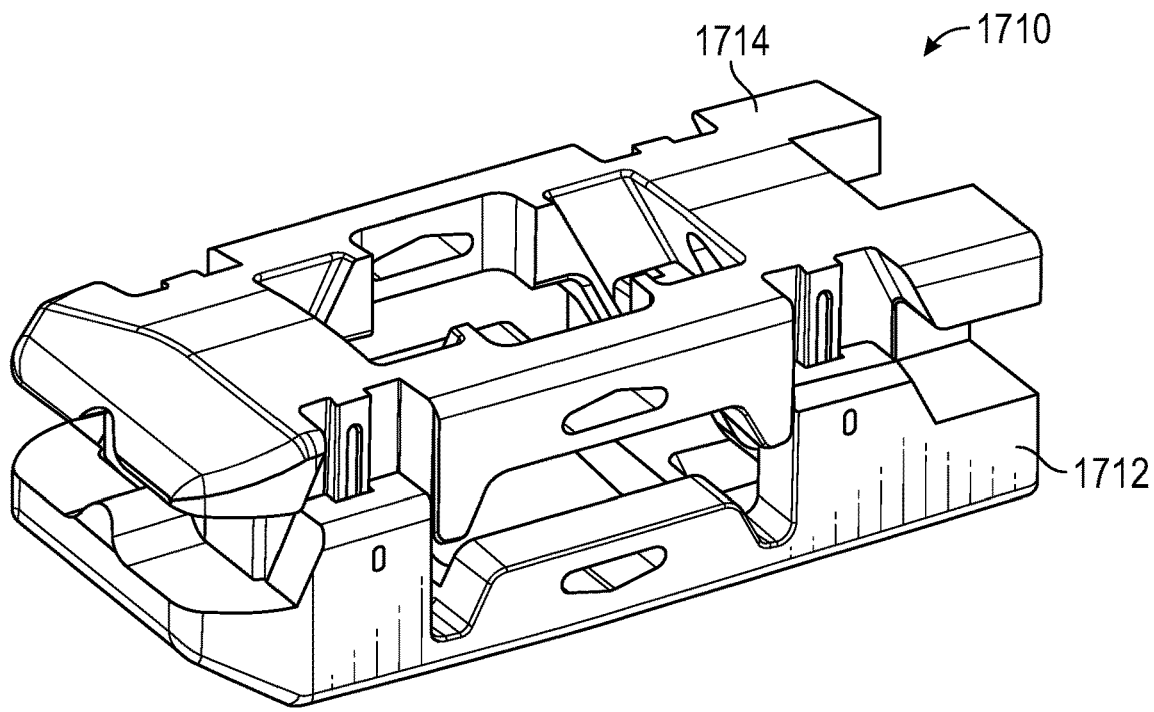
FIG. 68 is another perspective view of the expandable implant of FIG. 67.
Figure 69:
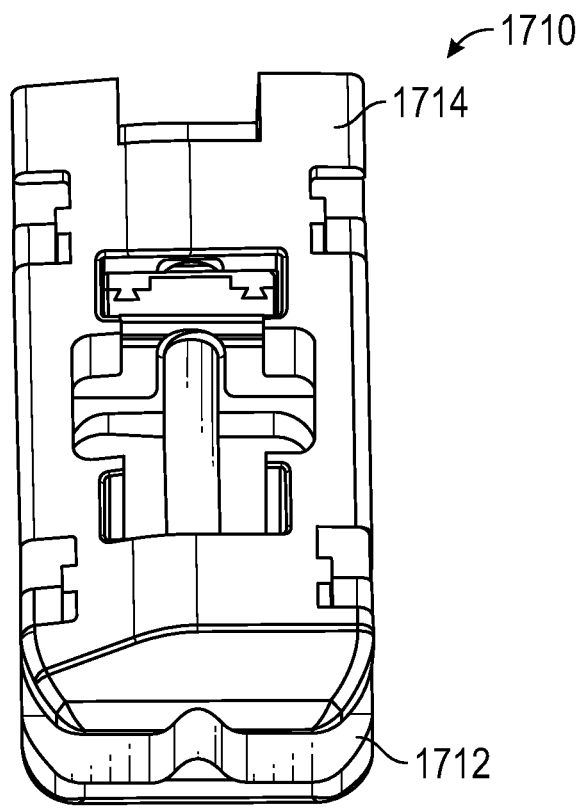
FIG. 69 is a top view of the expandable implant of FIG. 67.

Referring now to FIGS. 65 and 66, control member 1620 is shown in greater detail, it being understood that control member 1622 can share any and all features of control member 1620 disclosed herein. In one embodiment, control member 1620 includes a first generally flat face 1630 and a second generally flat face 1632. Faces 1630 and 1632 are generally parallel to one another and to the interior surfaces of the control channel of adjustable member 1614. First face 1630 extends from a top surface 1638, and second face 1632 extends upward from a bottom surface 1640. In certain embodiments, the control member includes a first, rigid portion and a second, deformable portion. In certain embodiments, the deformable portion defines a planar surface (e.g., face 1630) that is configured to slidably engage the adjustable member 1614.

In one embodiment, one or more slots (e.g., wired cuts, voids, etc.) are provided in control member 1620 (e.g., the second, deformable portion) to enable control member 1620 to be relatively more compressible (e.g., more compressible than a solid metal structure without such slots). In certain embodiments, the second, deformable portion (i.e., the compressible portion) is more compressible than the remainder of the implant. For example, as shown in FIGS. 65 and 66, control member 1620 includes a first slot 1634 and a second slot 1636. First slot 1634 extends through control member 1620 and down from top surface 1638. Second slot 1636 extends through control member 1620 and upward from bottom surface 1640. In one embodiment, slots 1634 and 1636 are parallel to each other and/or to first and second faces 1630, 1632. In other embodiments, slots 1634, 1636 are non-parallel to each other and/or to first and second faces 1630, 1632. Slots 1634, 1636 extend along less than the full height of control member so as to maintain the unitary structure of control member 1620.

FIGS. 63-66 generally disclose control members having two slots, with one slot extending upward from a top surface of the control member and a second slot extending upward from a bottom of the control member. In various alternative embodiments, more or fewer slots may be utilized, and the slots may extend from one or both of top surface 1638 and bottom surface 1640. Furthermore, the slots may have any appropriate thickness. The particular size, shape, number, and orientation of the slots may be varied to suit a particular application (e.g., to provide a desired modulus of elasticity for the implant).

In use, implant 1610 is installed in a desired position, such as between intervertebral bodies within the spine. When implant 1610 is subjected to compressive loads, control members 1620, 1622 may absorb some of the compressive forces by compressing due to the slotted structure of the control members. As such, the overall compressibility of implant 1610 may be selected to closely imitate that of the human anatomy.

In some embodiments, control members 1620, 1622 are made of a relatively more compressible material than the remainder of implant 1610. In other embodiments, control members 1620, 1622 are made of the same or a similar material than the remainder of implant 1610. For example, in one embodiment, control members 1620, 1622 are made of a polymer or composite, such as PEEK, while the remainder of implant 1610 is made of a metal, such as titanium. As discussed in further detail below, in further alternative embodiments, the control members 1620, 1622 may be made of a combination of polymers, composites, and metals.

Referring now to FIGS. 67-72, an implant 1710 is shown according to an exemplary embodiment. Implant 1710 may share any of the features of the other implants disclosed herein, including expansion mechanisms, alignment/guide members, and the like. All such combinations of features are to be understood to be within the scope of the present disclosure.

Figure 70:
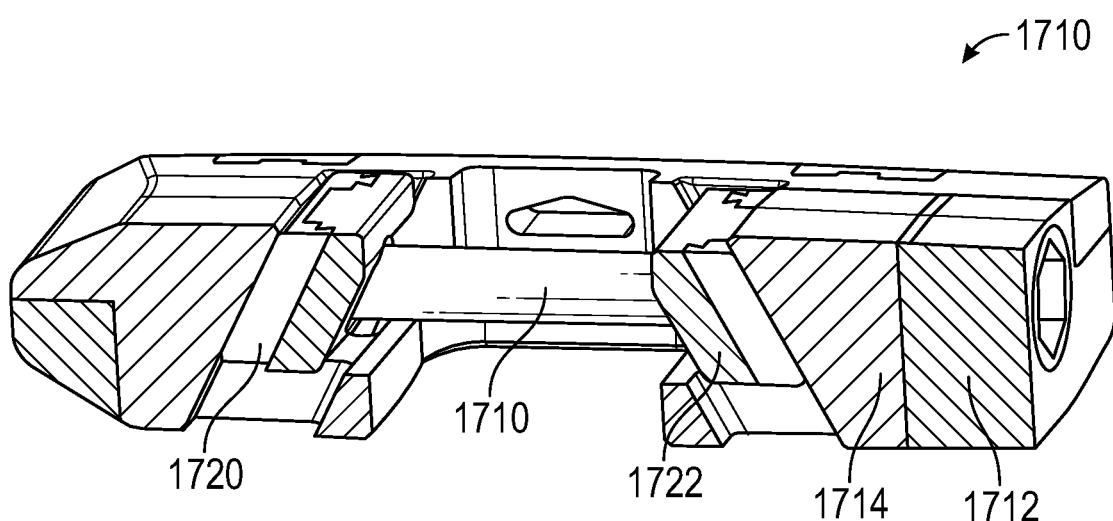
FIG. 70 is a cross-section view of the expandable implant of FIG. 67.

Referring to FIGS. 67-70, implant 1710 includes a base member 1712 and an adjustable member 1714. A control shaft 1716 and control members 1720, 1722 enable adjustment of adjustable member 1714 relative to base member 1712, as discussed in greater detail with respect to implant 1310 and the other embodiments disclosed herein. It should be noted that FIG. 70 is a cross-sectional view taken along a plane slightly offset from the axis of control member 1716 in order to provide more clarity with respect to the structure of control members 1720, 1722. As shown in FIGS. 67-70, implant 1710 has a lower profile and larger width relative to height than implant 1610, which may provide increased stability for implant 1710.

Figure 71:
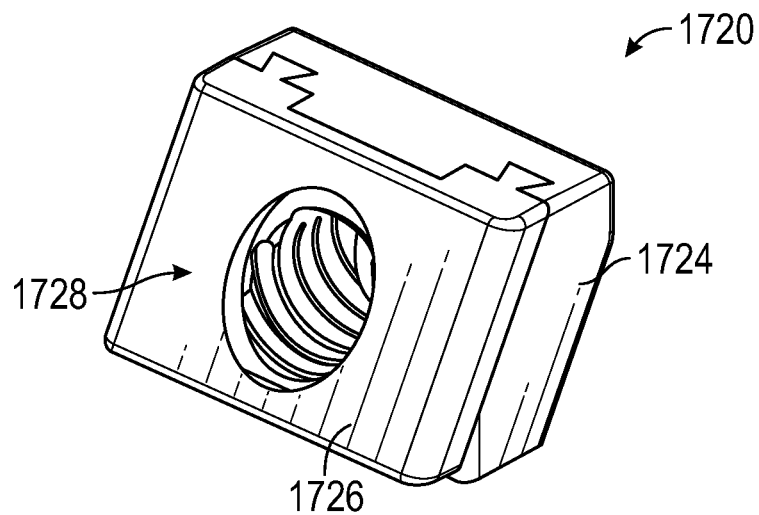
FIG. 71 is a perspective view of a control member of the expandable implant of FIG. 67.
Figure 72:
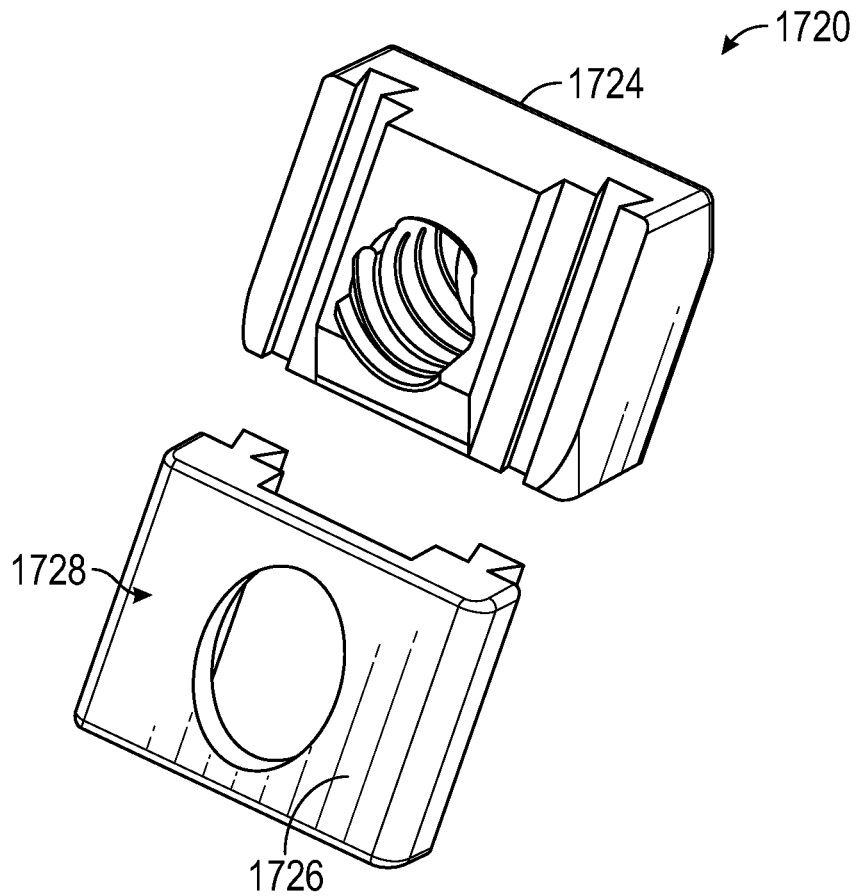
FIG. 72 is an exploded view of the control member of FIG. 71.

Referring now to FIGS. 71-72, control member 1720 is shown in greater detail, it being understood that control member 1722 can share any and all features of control member 1720 disclosed herein. In one embodiment, control member 1720 includes a base portion 1724 and an engagement portion 1726. Base portion 1724 is coupled to engagement portion 1726. As shown in FIGS. 71-72, base portion 1724 and engagement portion 1726 may include corresponding dovetail features enabling a secure coupling of components. In other embodiments, base portion 1724 and engagement portion 1726 may be coupled using other methods, including adhesives, welding, mechanical fasteners, and the like.

In one embodiment, base portion 1724 includes threads to threadingly engage control member 1716. Base portion 1724 may be made of a relatively non-compressible material, such as titanium or another metal. In other embodiments, base portion 1724 may be made of other materials. Engagement portion 1726 may or may not include threads to threadingly engage control member 1716. For example, if engagement portion 1726 is made of a relatively softer, or compressible material, it may be desirable to not utilize threads with engagement portion 1726. Engagement portion may be made of a relatively softer and/or more compressible material than base member 1724 and/or the remainder of the components of implant 1710. In some embodiments, engagement portion 1726 is made of PEEK. On other embodiments, engagement portion may be made of other materials.

Generally, engagement member 1726 includes a generally flat face 1728 configured to engage a corresponding surface of the control channels of adjustable member 1714. In this way, engagement portion 1726 may absorb a certain amount of compressive forces imparted to implant 1710. For example, in use, implant 1710 is installed in a desired position, such as between intervertebral bodies within the spine. When implant 1710 is subjected to compressive loads, control members 1720, 1722 may absorb some of the compressive forces by compressing due to the compressible nature of engagement portion 1726. As such, the overall compressibility of implant 1710 may be selected to closely imitate that of the human anatomy.

In some embodiments, engagement portion 1726 is made of a relatively more compressible material than the remainder of implant 1710. For example, in one embodiment, engagement portion 1726 is made of a polymer or composite, such as PEEK, while the remainder of implant 1710 is made of a metal, such as titanium.

In some embodiments, implants 1610, 1710 provide for increased compressibility in only a single direction (e.g., in a direction along the height of the implants). Compressive forces are transferred through the base members and/or the adjustable members to the control members, where all or a portion of the compressive force is absorbed by way of compression of the control members. As disclosed herein, the overall compressive characteristics of the implants may be similar to those of the human anatomy (e.g., spinal bone material, etc.).

It should be understood that the compression features disclosed in FIGS. 63-72 and elsewhere herein are applicable to a wide variety of implants in addition to those disclosed herein. In general, the compression features may apply to any expandable implant. In some embodiments, increased compressibility is provided at the interface of surfaces or components that provide expansion/adjustment features. For example, as discussed with respect to FIGS. 63-72, the compressibility is provided at the interface between the control members and the control channels. In other embodiments, the compressibility may be provided at the interface of wedging surfaces that interface to provide expansion features for an implant. In yet further embodiments, the compressibility may be provided by other components. The control members, control channels, wedging members all provide control portions for selective adjustment of the expandable implants herein. The control portions further provide for increased compressibility of the expandable implant (e.g., to mimic the compressibility of human bone, etc.).

Figure 73:
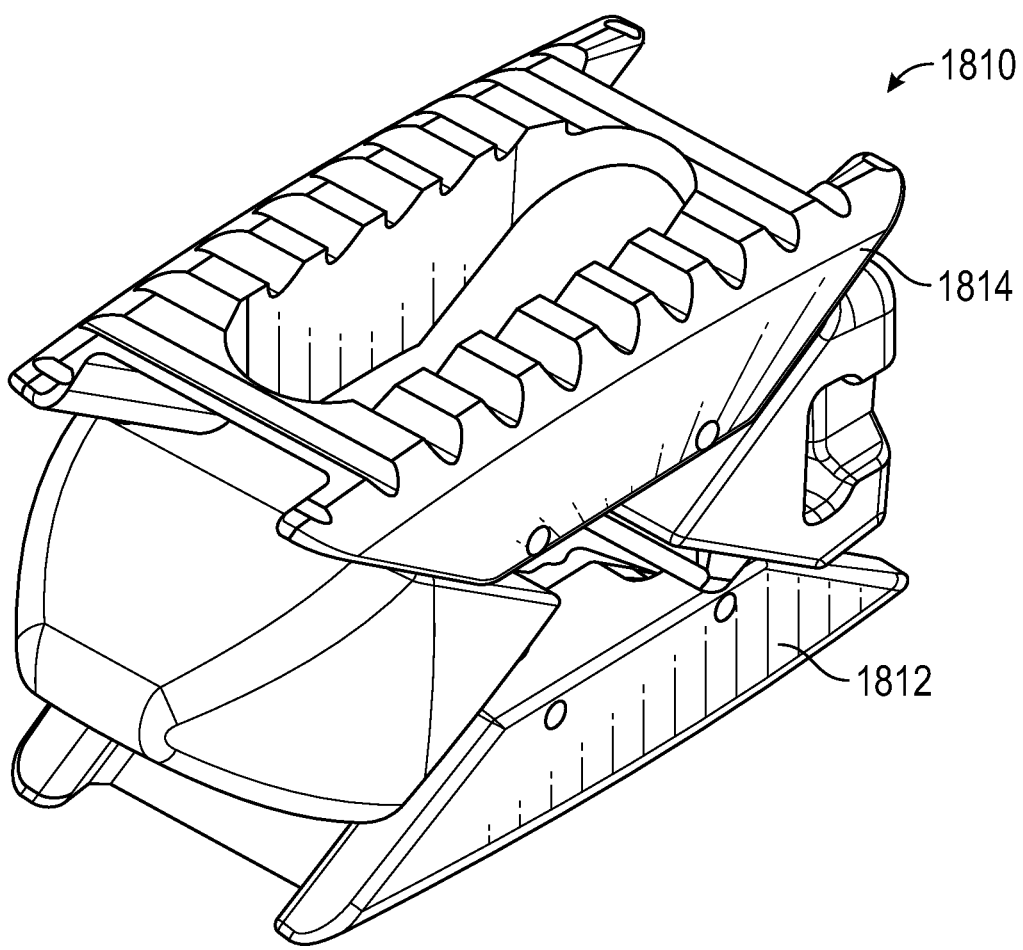
FIG. 73 is a perspective view of an expandable implant according to another embodiment.
Figure 74:
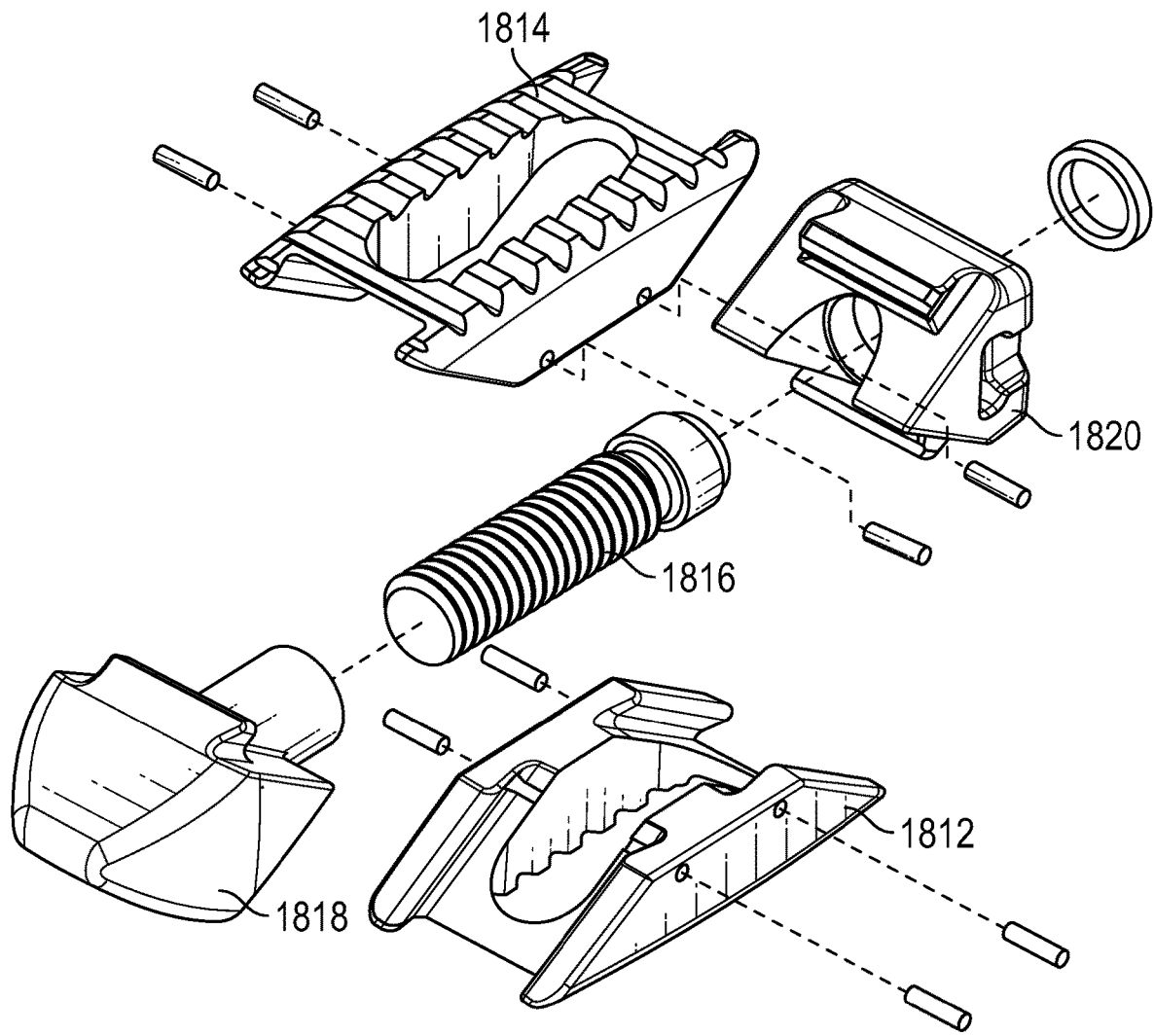
FIG. 74 is an exploded view of the expandable implant of FIG. 73.
Figure 75:
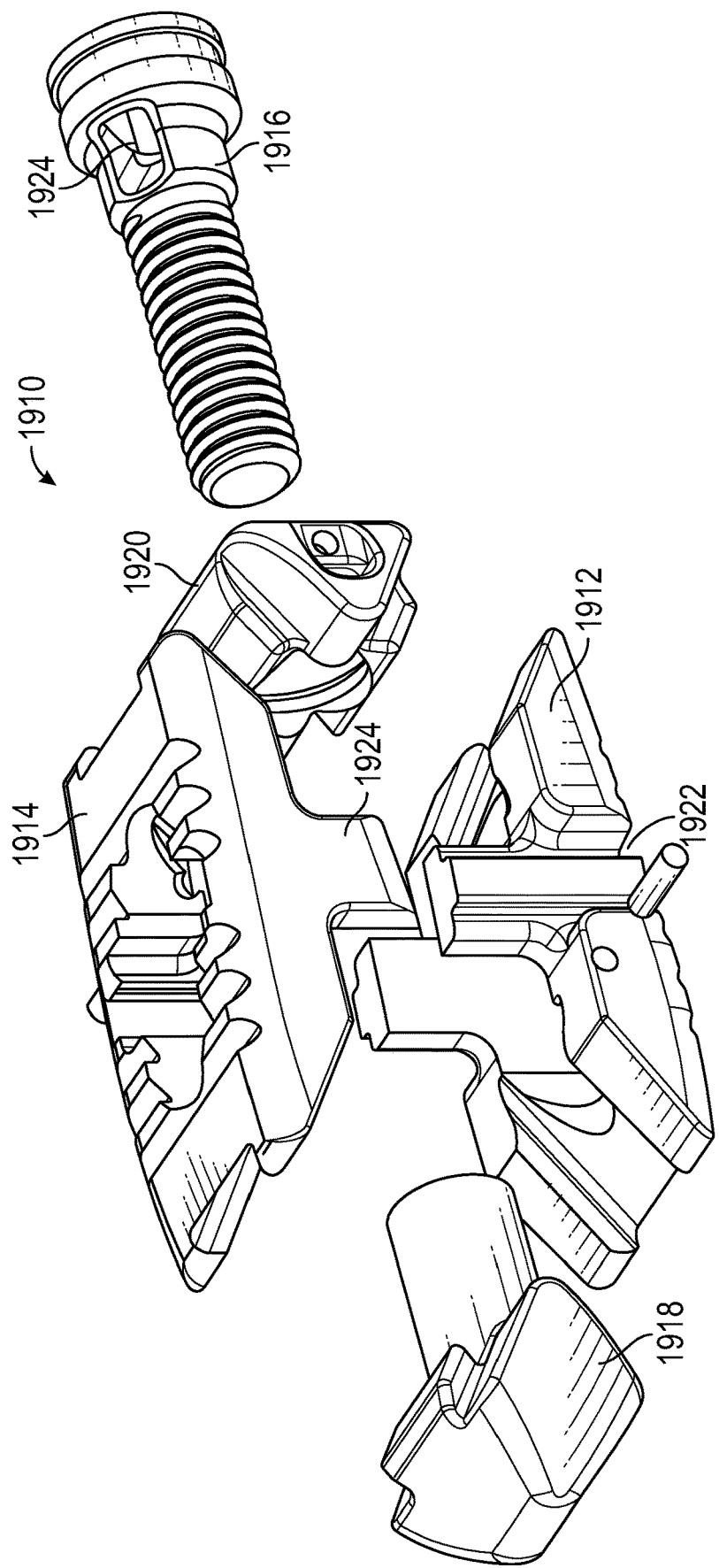
FIG. 75 is an exploded view of the expandable implant of FIG. 73 according to another embodiment.

For example, referring to FIGS. 73-75, expandable implants are shown according to alternative embodiments. As shown in FIGS. 73 and 74, an implant 1810 includes a first or bottom support 1812 and a second or top support 1814. First and second wedge members 1818, 1820 (e.g., control members, etc.) are received on a control shaft 1816. Rotation of control shaft 1811 causes relative movement between first and second wedge members 1818, 1820, which in turn causes relative movement between first and second supports 1812, 1814.

In some embodiments, increased compressibility (e.g., greater compressibility than a reminder of the implant) is provided at one or more of the interfacing portions of first and second supports 1812, 1814 and first and second wedge members 1818, 1820. In some embodiments, the interfacing surfaces may be made of a relatively more pliable material (e.g., PEEK), is a similar fashion to the embodiments of FIGS. 71 and 72. In other embodiments, structural modifications such as slits, etc., such as those shown in FIGS. 63-66, may provide increased compressibility. In further embodiments, all or a portion of the wedging members may be made of a relatively more compressible material. In yet further embodiments, increased compressibility may be provided in other ways.

FIG. 75 shows an implant 1910 similar to implant 1810, except that implant 1910 includes additional alignment features in the form of upstanding u-shaped channels/recesses 1922 and correspondingly shaped alignment guides 1924. Implant 1910 further includes control shaft 1916 having access port 1924 enabling delivery of fluid or other material such as bone growth material through the head of the control shaft 1916 and to the interior of implant 1910. Implant 1910 may share any of the features of 1810 including any of the compression features disclosed herein.

Referring now to the Figures generally, the various embodiments disclosed herein provide expandable implants including a base member, an adjustable member adjustably coupled to the base member and movable between a first, collapsed position, and a second, expanded position, and a control shaft rotatably received by the base member, where rotation or other manipulation of the control shaft cause relative movement of the adjustable member relative to the base member. At least one control member is received on the control shaft and by the control channel, and rotation of the control shaft causes the control member to translate along the control shaft and along the control channel.

In some embodiments, the adjustable member moves in a linear fashion relative to the base member. In other embodiments, the adjustable member moves in a non-linear fashion relative to the base member. In further embodiments, the adjustable member pivots about a pivot axis relative to the base member. The pivot axis may be provided by a pivot pin extending through one or both of the adjustable member and the base member.

In some embodiments, a single control member and control channel are utilized. In other embodiments, multiple (e.g., 2) control members and control channels are utilized. In some embodiments, the multiple control channels are parallel and straight. In other embodiments, the control channels are non-parallel and straight (e.g., angled toward each other). In further embodiments, the control channels are non-parallel and non-straight such that the adjustable member moves in a non-linear fashion relative to the base member.

In some embodiments, the control shaft includes a control thread corresponding to each control member. As such, while in some embodiments the control shaft includes a single control thread, in other embodiments the control shaft includes multiple (e.g., first and second) control threads. In some embodiments, the control threads are like-threaded. In other embodiments, the control threads have different threads. For example, in some embodiments, a first control thread is opposite-handed from a second control thread. In further embodiments, a first control thread has a different pitch from a second control thread. In yet further embodiments, a first control thread is different handed and has a different pitch from a second control thread.

In some embodiments, one or both of the adjustable member and the base member include projections/grooves to provide a gripping surface intended to facilitate gripping adjacent portions of bone. In further embodiments, one or both of the adjustable member and the base member include one or more apertures and/or cavities configured to promote bone growth in and around the adjustable member and the base member. In some embodiments, the apertures extend from a top, bottom, and/or side surface of the adjustment member or the base member and to a central cavity of the implant.

According to any of the embodiments disclosed herein, one or more bone screws may be included and positioned to extend through one or both of the adjustable member and the base member and into adjacent portions of bone. In some embodiments, multiple bone screws are used. A first bone screw may extend through the adjustable member and into a first portion of bone, and a second bone screw may extend through the base member and into a second portion of bone. In further embodiments, multiple bone screws are accessible and manipulatable by way of a front face of the implant defined by one or both of the adjustable member and the base member. A head and tool port of the control shaft may further be accessible by way of the front face of the implant.

In various embodiments, any suitable configuration of the control shaft/control member(s)/control channel(s) may be utilized. In some embodiments, an at least partially spherical control member threadingly engages a threaded control shaft and translates both along the control shaft and within the control channel. In other embodiments, the control member is non-spherical and is received at least partially on or in a control rail or control channel provided by the adjustable member, such that the control member translates along both the control shaft and the control channel or control rail.

An embodiment of the present disclosure is a method of positioning an expandable implant including receiving, by an adjustment member of the expandable implant, a manipulation tool at a first angle, wherein the adjustment member includes a channel that receives a portion of the manipulation tool. The method including securing the expandable implant to the manipulation tool by rotating the portion of the manipulation tool through the channel, the rotation orienting the expandable implant to a second angle. The method including receiving, by the adjustment member, a locking member of the manipulation tool, the locking member locking the expandable implant at the second angle. The method including positioning, by a user using the manipulation tool, the expandable implant, and receiving, by an expansion mechanism of the expandable implant, via the manipulation tool, an expansion force, the expansion force causing the expandable implant to expand.

In some embodiments, the channel is a dovetail recess and the portion of the manipulation tool is a dovetail projection. In some embodiments, the expansion force is a torque. In some embodiments, the locking member is a pin configured to fit within a slot of the adjustment member. In some embodiments, the adjustment member is coupled to a base member of the expandable implant, the base member including a bottom surface to contact an adjacent portion of bone. In some embodiments, the expandable implant including an adjustable member coupled to the base member, the adjustable member including a top surface to contact an adjacent portion of bone, the adjustable member configured to expand relative to the base member in response to the expansion force. In some embodiments, the expandable implant is perpendicular to the manipulation tool while at the first angle and is parallel to the manipulation tool while at the second angle.

Another embodiment of the present disclosure is an expandable implant including a base member including a bottom surface to contact an adjacent portion of bone, an adjustable member coupled to the base member and including a top surface to contact an adjacent portion of bone. The expandable implant further including an adjustment member including a channel and coupled to the adjustable member and configured to receive a portion of a manipulation tool at a first angle. The adjustment member further configured to secure the manipulation tool to the expandable implant by rotating the portion of the manipulation tool through the channel, wherein the rotation orients the expandable implant to a second angle, and receive a locking member of the manipulation tool, the locking member locking the expandable implant at the second angle. The expandable implant is positioned by a user using the manipulation tool and wherein the expandable implant is expanded via the manipulation tool.

In some embodiments, the channel is a dovetail recess and the portion of the manipulation tool is a dovetail projection. In some embodiments, the base member receives a screw drive to expand the expandable implant. In some embodiments, the screw drive is coupled co-axially within the manipulation tool. In some embodiments, the locking member is a pin configured to fit within a slot of the adjustment member. In some embodiments, the expandable implant is perpendicular to the manipulation tool while at the first angle and is parallel to the manipulation tool while at the second angle.

Another embodiment of the present disclosure is a manipulation tool for an expandable implant including a first portion including a first end and a second end, wherein the first end is configured to be a handle, the second end including a locking member. The manipulation tool including a second portion co-axially coupled within the second end of the first portion, the second portion configured to translate between a first position and a second position, the second portion including a coupling member configured to couple to an attachment member of the expandable implant at a first angle, wherein the coupling member secures the expandable implant to the manipulation tool by rotating through a channel of the attachment member to a second angle. Translating the second portion from the first position to the second position engages the locking member of the first portion and locks the expandable implant to the manipulation tool, locking the expandable implant at the second angle. The manipulation tool positions the expandable implant.

In some embodiments, the manipulation tool further including an adjustment mechanism co-axially coupled within the first and second portions and configured to engage the expandable implant to cause expansion. In some embodiments, the adjustment mechanism is a screw drive. In some embodiments, the channel is a dovetail recess and the coupling member is a dovetail projection. In some embodiments, the locking member is a pin configured to fit within a slot of the expandable implant. In some embodiments, the manipulation tool is perpendicular to the expandable implant at the first angle and is parallel to the expandable implant at the second angle. In some embodiments, the first and second portions are hollow.

It is important to note that the construction and arrangement of the elements of the various implants and implant components as shown in the exemplary embodiments are illustrative only. Although a few embodiments have been described in detail in this disclosure, those skilled in the art who review this disclosure will readily appreciate that many modifications are possible (e.g., variations in sizes, dimensions, structures, shapes and proportions of the various elements, values of parameters, mounting arrangements, materials, colors, orientations, etc.) without materially departing from the novel teachings and advantages of the subject matter recited in the various embodiments. Accordingly, all such modifications are intended to be included within the scope of the present disclosure as defined in the appended claims. The order or sequence of any process or method steps may be varied or re-sequenced according to alternative embodiments. Other substitutions, modifications, changes, and/or omissions may be made in the design, operating conditions, and arrangement of the exemplary embodiments without departing from the spirit of the present disclosure.

What is claimed is:

1. An expandable implant comprising:
a first support configured to engage a first portion of bone;
a second support configured to engage a second portion of bone, the second support adjustably coupled to the first support such that the expandable implant is movable between a collapsed position and an expanded position; and
a control assembly including a control shaft and a wedging member coupled to the control shaft, the wedging member including a body portion coupled to an elastically compressible portion, and wherein manipulation of the control shaft causes relative movement of the second support relative to the first support;
wherein the wedging member slidably engages the second support continuously at a wedging member interface during manipulation of the control shaft to move the second support relative to the first support from the collapsed position to the expanded position, wherein the wedging member interface comprises the elastically compressible portion defining a planar surface, and wherein the body portion is less compressible than the elastically compressible portion.

2. The expandable implant of claim 1, wherein the wedging member comprises the wedging member interface.

3. The expandable implant of claim 1, wherein the planar surface is angled relative to a direction of movement of the second support relative to the first support.

4. The expandable implant of claim 1, wherein the elastically compressible portion is configured to compress when the expandable implant is subjected to compressive loads via the first and second supports.

5. The expandable implant of claim 1, wherein the elastically compressible portion is made of PEEK.

6. The expandable implant of claim 1, wherein the wedging member interface is a first wedging member interface and the elastically compressible portion is a first elastically compressible portion configured to engage a first portion of the second support,
further comprising a second wedging member interface comprising a second elastically compressible portion defining a second planar surface configured to slidingly engage a second portion of the second support.

7. The expandable implant of claim 1, wherein the body portion is made of metal.

8. The expandable implant of claim 1, wherein the wedging member interface is configured such that an overall compressibility of the expandable implant imitates the compressibility of the human anatomy.

9. An expandable implant, comprising:
a lower support;
an upper support adjustably coupled to the lower support such that the expandable implant is movable between a collapsed position and an expanded position; and
a control assembly including a control shaft, a first control member coupled to the control shaft, and a second control member coupled to the control shaft, wherein manipulation of the control shaft causes relative movement of the upper support relative to the lower support;
wherein the first control member having compressible properties, the first control member comprising a (i) a body made of non-compressible material, (ii) a first slot extending from a first surface of the body and into the body, and (iii) a second surface configured to slidingly engage a first portion of the upper support continuously during manipulation of the control shaft to move the upper support relative to the lower support from the collapsed position to the expanded position, wherein the first slot and the second surface are parallel, and wherein the first slot enables the first control member to be compressible when a force is applied to the second surface, and
wherein the second control member comprises compressible properties and is configured to slidingly engage a second portion of the upper support.

10. The expandable implant of claim 9, wherein the body comprises a first rigid portion coupled to the second surface, the first rigid portion being relatively less compressible than the second surface.

11. The expandable implant of claim 9, wherein the second surface is configured to slidingly engage the first portion of the upper support upon rotation of the control shaft.

12. The expandable implant of claim 9, wherein the second surface is more compressible than a remainder of the expandable implant.

13. The expandable implant of claim 9, wherein the second control member comprises a third surface configured to slidingly engage the second portion of the upper support.

14. The expandable implant of claim 13, wherein the second and third surfaces are angled relative to a direction of movement of the upper support relative to the lower support.

15. An expandable implant, comprising:
a first support member;
a second support member coupled to the first support member and movable relative to the first support member along a first direction; and
a control assembly comprising a control shaft, a first control member coupled to the control shaft, and a second control member coupled to the control shaft, wherein the first control member comprises a first body portion and a first elastically compressible portion coupled to the first body portion, the first elastically compressible portion to slidingly engage a first portion of the second support member along a first interface during manipulation of the control shaft to move the upper support relative to the lower support from the collapsed position to the expanded position, wherein the first interface is angled relative to the first direction, and wherein the body portion is less compressible than the first elastically compressible portion, and
wherein the second control member comprises a second body portion and a second elastically compressible portion coupled to the second body portion, the second elastically compressible portion configured to slidingly engage a second portion of the second support member along a second interface angled relative to the first direction, and wherein the second body portion is less compressible than the second elastically compressible portion.

16. The expandable implant of claim 15, wherein the first body portion comprises a first rigid portion coupled to the first elastically compressible portion; and
wherein the second body portion comprises a second rigid portion coupled to the second elastically compressible portion.

17. The expandable implant of claim 16, wherein the first elastically compressible portion and the second elastically compressible portion are made of PEEK.

18. The expandable implant of claim 15, wherein the first support member comprises a first alignment portion and the second support member comprises a second alignment portion configured to engage the first alignment portion and maintain alignment between the first support member and the second support member during movement of the first support member relative to the second support member.

19. The expandable implant of claim 15, wherein the first elastically compressible portion defines a first planar surface configured to slidingly engage the first portion of the second support member and the second elastically compressible portion defines a second planar surface configured to engage the second portion of the second support member.

* * * * *